US005650553A

United States Patent [19]

Ecker et al.

[11] Patent Number: 5,650,553
[45] Date of Patent: Jul. 22, 1997

[54] PLANT GENES FOR SENSITIVITY TO ETHYLENE AND PATHOGENS

[75] Inventors: Joseph Ecker, Erial, N.J.; Madge Rothenberg, Haverford, Pa.; Anne Lehman, Philadelphia, Pa.; Gregg Roman, North Wales, Pa.

[73] Assignee: The Trustees of the University of Pennsylvania, Philadelphia, Pa.

[21] Appl. No.: 261,822

[22] Filed: Jun. 17, 1994

Related U.S. Application Data

[63] Continuation-in-part of Ser. No. 3,311, Jan. 12, 1993, Pat. No. 5,444,166, and Ser. No. 171,207, Dec. 21, 1993, which is a continuation of Ser. No. 899,262, Jun. 16, 1992, abandoned, said Ser. No. 3,311, is a continuation-in-part of Ser. No. 928,464, Aug. 10, 1992, Pat. No. 5,367,065.

[51] Int. Cl.$^6$ .......................... A01H 4/00; C07K 14/415; C12N 5/14; C12N 15/28

[52] U.S. Cl. .......................... 800/205; 435/419; 435/418; 514/12; 530/370; 536/23.6

[58] Field of Search .......................... 800/205; 435/240.4; 514/12; 530/370; 536/23.6

[56] References Cited

PUBLICATIONS

Harpham et al. The Effect of Ethylene on the Growth and Development of Wild–type and Mutant Arabidopsis Tahliana Heynh *Annals of Botany* 1991 68:55.

Boller T. The Plant Hormone Ethylene A.K. Mattoo and J.C. Suttle eds. CRC Press, Inc. Boca Raton 1991 293–314.

Yu et al. Regulation of Auxin–induced Ethylene Production in Mung Bean Hypocotyls *Plant Physiol.* 1979 63:589–590.

Guzman and Ecker, Exploiting the Triple Response of Arabidopsis to Identify Ethylene–Related Mutants *The Plant Cell* 1990 2:513–523.

Sato and Theologis Cloning the mRNA encoding 1–aminocyclopropan–1–carboxylate syntase the key enzyme for ethylene biosynthesis in plants *Proc. National Acad. Sci* 1989 86:6621–6625.

Van Der Straeten et al. Cloning and sequence of two different cDNAs encoding 1–aminocyclopropane–1–carboxylate synthase in tomato *Proc. National Sci* 1990 87:4859–4863.

Nakajima et al. Molecular Cloning and Sequence of a Complementary DNA Encoding 1–Aminocyclopropane–1–carboxylate Synthase Induced by Tissue Wounding *Plant Cell Physiol.* 1990 31(7):1021–1029.

Spanu et al. Analysis and Cloning of the Ethylene–forming enzyme from tomato by fucntional expression of its mRNA in Xenopus Laevis oocytes *The EMBO Journal* 1991 10:2007–2013.

Blinder et al. Constitutive Mutants in the Yeast Pheromone Response: Ordered Function of the Gene Products *Cell* 1989 56:479–486.

Kende H. Enzymes of Ethylene Biosynthesis *Plant Physiol* 1989 91:1–4.

Neljubow, D., *Pflanzen Beih. Bot. Zentralb.*, 1901, 10: 128.

Gray et al. *Plant Mol Biol.* 1992 19, 69.

Nakajima et al., Molecular Cloning and Sequence of a Complementary DNA Encoding 1–Aminocyclopropane–1–carboxylate Synthase Induced by Tissue Wounding *Plant Cell Physiol.* 1990, 29:989.

Whalen et al., "Identification of *Pseudomonas syringae* Pathogens of Arabidopsis and a Bacterial Locus Determining Avirulence on Both Arabidopsis and Soybean"..

Theologis, A., One Rotten Apple Spoils the Whole Bushel: The Role of Ethylene in Fruit Ripening *Cell* 1992 70:181.

Yang et al., Ethylene Biosynthesis and its Regulation in Higher Plants *Ann. Rev. Plant Physiol.* 1984 35:155.

McGarvey et al., Ripening–Related Gene from Avocado Fruit *Plant Physiol.* 1992 98:554.

Dong et al., "Induction of Arabidopsis Defense Genes by Virulent and Avirulent *Pseudomonas syringae* Strains and by a Cloned Avirulence Gene", *The Plant Cell* 1991 3:61.

Debener et al., "Identification and Molecular Mapping of a Single *Arabidopsis thaliana* Locus Determining Resistance to a Phytopathogenic *Pseudomonas syringae* Isolate", *The Plant Journal* 1991, 1, 289.

Bent, A.F., et al., "Disease Development in Ethylene–Insensitive *Arabidopsis thaliana* Infected with Virulent and Avirulent Pseudomonas and Xanthomonas Pathogens", *Molecular Plant–Microbe Interactions* 1992, 5, 372.

Agrios, G.N., *Plant Pathology* 1988, 126, Academic Press, San Diego.

Mussel, H., "Tolerance to Disease", p. 40, in *Plant Disease: An Advanced Treatise*, vol. 5, Horsfall, J.G. and Cowling, E.B., eds., 1980, Academic Press, New York.

Chang et al. Restriction fragment length polymorphism linkage map for *Arabiopsis thaliana Proc. Natl. Acad. Sci USA* 1988 85:6857.

Sambrook et al., *Molecular Cloning: A Laboratory Manual*, 2nd ed., 1989, Cold Spring Harbor Laboratory Press, Cold Spring Harbor, NY.

Tercero, J.C., Localized Mutagenesis and Evidence for Post–transcriptional Regulation of *MAK3 JBC* 1992 267:20270.

Kieber et al., CTR1, a Negative Regulator of the Ethylene Response Pathway in Arabidopsis, Encodes a member of the Raf Family of Protein Kinases *Cell*, 1993 72:427–441.

Feinberg and Vogelstein, A Technique for Radiolabeling DNA Restrictionn Endonuclease Fragments to High Specific Activity *Anal. Biochem.* 1984 177:266–267.

(List continued on next page.)

*Primary Examiner*—Che S. Chereskin
*Attorney, Agent, or Firm*—Woodcock Washburn Kurtz MacKiewicz & Norris

[57] ABSTRACT

The present invention is directed to nucleic acid sequences for ethylene insensitive, EIN loci and corresponding amino acid sequences. The present invention is also directed to nucleic acid sequences for hookless1, HLS1, alleles and amino acid sequences.

17 Claims, 35 Drawing Sheets

OTHER PUBLICATIONS

Bleecker et al. in "Insensitivity to Ethylene Conferred by a Dominant Mutation in *Arabidopsis thaliana*", *Science* 1990 241:1086.

Koorneef and Stamm, *Methods in Arabidopsis Research*, eds. C. Koncz, N-H Chua, and J. Schell, 1992, World Scientific Publishing Co., Singapore.

Nam et al., Restriction Fragment Length Polymorphism Linkage Map of *Arabidopsis thaliana Plant Cell* 1990 1:699.

Matallana, et al., *Methods in Arabidopsis Research*, eds C. Koncz, N-H Chua, and J Schell, 1992, World Scientific Publishing Co., Singapore.

Grill and Somerville, *Mol. Gen, Genet.* 1991, 226, 484.

Klee and Estelle, Molecular Genetic Approaches to Plant Hormone Biology *Annual Review of Plant Physiology* 1991 42:529–551.

Rubenstein, Characteristics of Hook Formation by Bean Seedlings *Plant Physiology* 1972 49:640–643.

Clark, et al., On the Identification of the Rosy Locus DNA in Drosophila Melanogaster: Intragenic Recombination Mapping of Mutations Associated with Insertions and Deletions *Genetics* 1986 112:755.

Reardon et al., Molecular Analysis of Diepoxybutane–Induced Mutations at the Rosy Locus of Drosophila melanogaster *Genetics* 1987 115:323.

Feldmann and Marks, Agrobacterium–mediated transformation of germinating seeds of *Arabidopsis thaliana*: A non–tissue culture approach *Mol. Gen. Genet.* 1987 208:1–9.

Jefferson et al., GUS fusions: β–Glucuronidase as a sensitive and versatile gene fusion marker in higher plants *EMBO Journal* 1987 6:3901–3907.

Velvekins et al., *Agrobacterium tumefaciens*–mediated transformation of *Arabidopsis taliana* root explants by using kanamycin selection *PNAS* 1988 85:5536–5540.

Restrepo et al., *Plant Cell* 1990, 2, 987–998.

Abel and Theologis, *Plant J.* 1994, 5, 421–427.

Abeles et al. Ethylene In Plant Biology Second Edition 1992.

```
                          1                                                       50
pileup.msf(ei11)    ..hhhmMMFM  EMGMYGNMDF  FSSs..TalD  vCPIPQaEqE  pVVeDVDYtD
pileup.msf(ei13)    iiitttMMFN  EMGMCGNMDF  FSSgSLgEVD  fCPvPQaEpD  alVED.DYtD
pileup.msf(ei12)    ..dsmdMynN  niGMFrsLvc  sSappFTEgh  MCs...dsht  alcDDls.sD
pileup.msf(ei13)    ........mg  DLaM......  ....SvaDlr  MenePddlas  dnVaEIDvaD
Consensus           ----------  ---M------  ----------  ----------  ---------D 51                                                      100
pileup.msf(ei11)    DEmDVDELEk  RMWRDKMRLK  RLKEQQsKcK  EGVDgsKQRQ  SW..EQARRK
pileup.msf(ei13)    DEiDVDELEr  RMWRDKMRLK  RLKEQd.KGK  EGVDaaKQRQ  SQ..EQARRK
pileup.msf(ei12)    EEmEIEELEk  kiWRDKqRLK  RLKEmaKnGl  gtrlllKQqh  ddfpEhsskr
pileup.msf(ei13)    EEiDaDDLEr  RMWkDrvRLK  RiKErQKaGs  qGaqt.Ketp  kkisDQAqRK
Consensus           -E-----LE-  --W-D--RLK  R-KE------  ------K---  ----------

101                                                     150
pileup.msf(ei11)    KMSRAQDGIL  KYMLKMMEVC  KAQGFVYGII  PEkGKPVTGa  SDNLREWWKD
pileup.msf(ei13)    KMSRAQDGIL  KYMLKMMEVC  KAQGFVYGII  PEnGKPVTGa  SDNLREWWKD
pileup.msf(ei12)    tMykaQDGIL  KYMsKtMErY  KAQGRVYGIV  lEnGKtVaGs  SDNLREWWKD
pileup.msf(ei13)    KMSRAQDGIL  KYMLKLMEVC  KvrGFVYGII  PEkGKPVaGs  SDNiRaWWKE
Consensus           -M--AQDGIL  KYM-K-ME--  K--GFVYGI-  -E-GK-V-G-  SDN-R-WWK- 151                                                     200
pileup.msf(ei11)    KVRFDRNGPA  AIAKYQsENN  ISGGSnDcNs  IVGPTPHTLQ  ELQDTTLGSL
pileup.msf(ei13)    KVRFDRNGPA  AltKYQaENN  Ip.GihEGNN  plGPTPHTLQ  ELQDTTLGSL
pileup.msf(ei12)    KVRFDRNGPA  AlikHQrDiN  ISdGSDsGse  vgdsTaqkLl  ELQDTTLGaL
pileup.msf(ei13)    KVkFDkNGPA  AIAKYeeEcl  afGkSDgnrN  ....sqfvLQ  DLQDaTLGSL
Consensus           KV-FD-NGPA  AI-K------  ----------  --------L-  -LQD-TLG-L 201                                                     250
pileup.msf(ei11)    LSALMQHCDP  PQRRFPLEKG  VsPPWWPnGn  EEWWPQLGLP  nE..QGPPPY
pileup.msf(ei13)    LSALMQHCDP  PQRRFPLEKG  VPPPWWPnGk  EDWWPQLGLP  KD..QGPaPY
pileup.msf(ei12)    LSALfpHCnP  PQRRFPLEKG  VtPPWWPtGk  EDWWdQLsLP  vDfrgvPPPY
pileup.msf(ei13)    LSsLMQHCDP  PQRkYPLEKG  tPPPWWPtGn  EEWWvkLGLP  Ks...qsPPY
Consensus           LS-L--HC-P  PQR--PLEKG  --PPWWp-G-  E-WW--L-LP  --------PY 251                                                     300
pileup.msf(ei11)    KKPHDLKKaW  KVGVLTAVIK  HMsPDIAKIR  KLVRQSKCLQ  DKMTAKESAT
pileup.msf(ei13)    KKPHDLKKaW  KVGVLTAVIK  HMFPDIAKIR  KLVRQSKCLQ  DKMTAKESAT
pileup.msf(ei12)    KKPHDLKKIW  KIGVLigVIr  HMasDIsnlp  nLVRrSrslQ  EKMTsrEgAl
pileup.msf(ei13)    rKPHDLKKmW  KVGVLTAVIn  HMLPDIAKIk  rhVRWSKCLQ  DKMTAKESAi
Consensus           -KPHDLKK-W  K-GVL--VI-  HM--DI--I-  --VR-S--LQ  -KMT--E-A-

301                                                     350
pileup.msf(ei11)    WLAIiNQEEv  vaReLYPES.  ....CPPLSs  SsslGSgSLL  iNDCSEYDVE
pileup.msf(ei13)    WLAIiNQEES  laReLYPES.  ....CPPLSL  Sg..GScSLL  mNDCSqYDVE
pileup.msf(ei12)    WLAalyrEka  ivdq......  .......iaM  SrennntSnF  lvpatggDpD
pileup.msf(ei13)    WLAVINQEES  liqqpssDng  nsnvtethrr  gnnadrrkpv  vNsdSDYDVD
Consensus           WLA----E--  ----------  ----------  ----------  -------D--
```

```
                    351                                                        400
pileup.msf(ei l1)   GFEKEqHgFD VEErKPEiVM mhpLasfgVA KMQhFPIKEE VattvNIEFT
pileup.msf(ei l3)   GFEKESH.YE VEEIKPEkVM nssnfGm.VA KMhdFPVKEE Vpag.NsEFm
pileup.msf(ei l2)   vLfpEstdYD VE........ ...LiGgthr tnQqYP...E fennyNcvYk
pileup.msf(ei l3)   GtEeaSgsvs skDsrrnql. .........q KeQptalshs VrdqdkaEkh
        Consensus   ---------- ---------- ---------- ---------- ----------

401                                                        450
pileup.msf(ei l1)   RKRKqNnDMN vmVMDRSagY TCENgqCPHS kmnLGFqDRs SRDNHQMvCP
pileup.msf(ei l3)   RKRKpNRDLN t.IMDR.TvF TCENIgCaHS eisrGFLDRN SRDNHQLaCP
pileup.msf(ei l2)   RKfeedfgMp m....hpTIL TCENsICPyS QphMGFLDRN IRENHQMtCP
pileup.msf(ei l3)   RrRKrpR... ....iRSgtv nrqeeeqPea QqrniLpDmN hvDaplLeYn
        Consensus   R--------- ---------- ---------- -------D-- ----------

451                                                        500
pileup.msf(ei l1)   YRDnRLaYGA ..SkFHMGgm KIVV...pqq PV.....QPI DLsGVgVPEn
pileup.msf(ei l3)   hRDsRLpYGA apSrFHvnev KpVVgFpqPr PVNsva.QPI DLTGI.VPED
pileup.msf(ei l2)   YkvTsF.... .......... .......... ..yqpT.kPy gMTGIMVP..
pileup.msf(ei l3)   ingThqeddv vdpnialGpe dngleLvvPe fnNnyTylPl vneqtMmPvD
        Consensus   ---------- ---------- ---------- -------P- -------P--

501                                                        550
pileup.msf(ei l1)   GQKMItELma MYDRnVQS.. ..nQTpptLM ENQSmvidak aaqNqQlnFn
pileup.msf(ei l3)   GQKMIsELms MYDRnVQS.. ..nQT.amvM ENQSvslLqP tvhNhQehLq
pileup.msf(ei l2)   ....cpDyng M.qqqVQS.. ..fQdqf... .NhpnDlyrP kapqr.....
pileup.msf(ei l3)   erpMlygpnp nqElqfgSgy nfynpsavFv hNQedDiLht qie.......
        Consensus   ---------- -------S-- ---------- -N-------- ----------

551                                                        600
pileup.msf(ei l1)   .......... .......... ......SGNQm Fmq....... ..........
pileup.msf(ei l3)   fpgnmvegsf fedlnipnra NnnnsSnNQt Ffqgnnnnnn vFkFdtaDhn
pileup.msf(ei l2)   .......... .......... ......GNdd Lved...... ..........
pileup.msf(ei l3)   .......... .........m NtqapphNag Feeapggvlq pLgLIgnEdg
        Consensus   ---------- ---------- -------N-- ---------- ----------

601                                                        650
pileup.msf(ei l1)   ......qgtN nGVNNRFQMV FDSTpFDMAa FDYRDDWqtG amEgmGkqqq
pileup.msf(ei l3)   nfeaahNnnN nssgNRFQLV FDSTpFDMAs FDYRDDmSmp Gv..VGTmdg
pileup.msf(ei l2)   .....LNpsp stlNqnLgLV L.pTdFn... .........G GeEtVGTenn
pileup.msf(ei l3)   vtgseLpqyq sGIIspL... ...TdLDfdy ggFgDDFSwf Ga........
        Consensus   ---------- ---------- ---T------ ---------- ----------

651        664
pileup.msf(ei l1)   qQQQQQDVSI W...
pileup.msf(ei l3)   MQQkQQDVSI W...
pileup.msf(ei l2)   LhnQgQElpt swiq
pileup.msf(ei l3)   .......... ....
        Consensus   ---------- ----
```

*FIG. 8B*

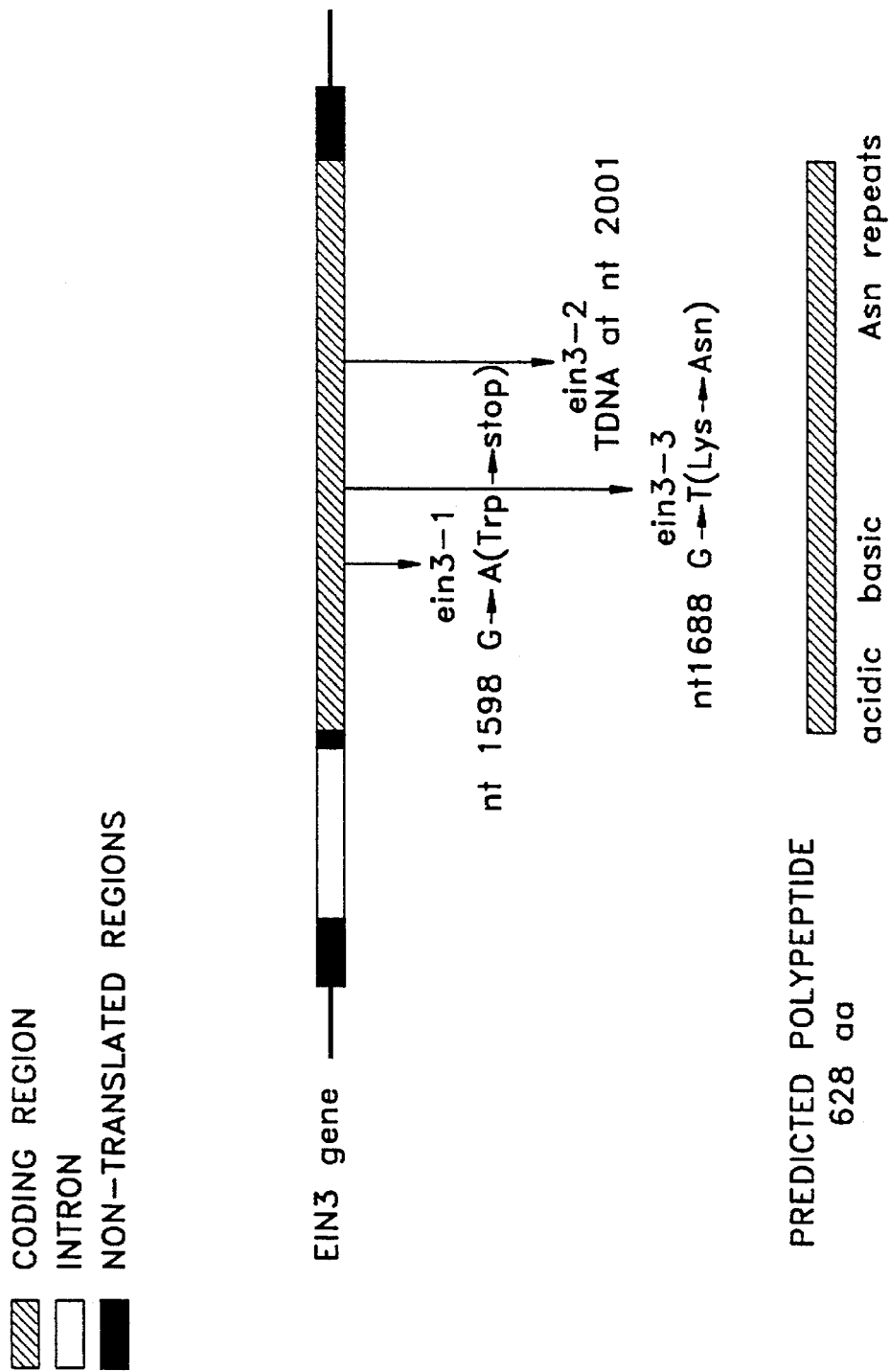

```
                                                                                    80
{rimJ: E.coli}       ............. ............. ...mfg yrsnvpkvrl ttdrlvVrLv hDrdaWrlad YyaenrhFlk pwepvrDEsh cypsgwqarl
{rimI: E.coli}       ............. ............. ............. ....mtetik vseslehav aEnhvkplyq LicknktWlq qsInwpqfvq seedtrktvq
{N3nat: Pseudomonas} ............. ............. ...mlw ssndvtqqgs rpktklggs. msiiatVkig pDeisamrav LdIFgkEFed iptysdrqpt neylanllhs
{Nnat: E.coli}       ............. ............. ...mlr ssndvtqqgs rpktklgsss mgiirtcrLg pDqvksmraa LdIFgrEFgd vatysqhqpd sdylgnllrs
{nat1: Streptomyces} mtlddtayr yrtsvpgdae aiealdgsft tdtvfrVtat gDgftlrevp vdppltkv.. FpddesDDes ddgedgdpds
{sat: Streptomyces}  mtthgstye frsarpgdae aiegldgsft tstvfeVdvt gDgfalrevp adpplvkv.. fpddggsDge dgaegedads
{sat: E.coli}        ...mk isvipeqvae tlda.enhfi vrevfdVhLs dqgfelstrs vspYrkDY.. isdddsDE.. .......ds
{ssat: Mouse}        ......makfk irpatasdcs ....dilrLi kELakYeyme dqviltEkdl qedgfgEhpf yhclvaevpk
{ssat: Human}        ......makfv irpataadcs ....dilrLi kELakYeyme eqviltEkdl ledgfgEhpf yhclvaevpk
{tab: Pseudomonas}   ......mnhaq lrrvtaesfa hyrhglaqLl fEtvhgg..a svgFmaDLdm qqayawcDgl kadiaagsll
{lat: Azospirillum}  ...... ......mpnvtiares plqdavVqLi eEldr..... ...YIgDLyp aesnhl...l dlqtlakpdi
{ard1: Yeast}        ...mpini rrat.indii cmqnanlhnl penymmkyYm yhtlsWpeas FvatttLdc edsdeqDEnd klEltldgtn
{MAK3: Yeast}        meivykpldi rneeqfasik kliddadlsep ysiyvyryFl nq...WpeIt Yia...... .......... ....vdnks
{HLS1: Arabidopsis}  mtvvreydpt rdlvgvedve rrcevgpsgk lslftdllgd picriRhsps YlmLvaEmgt e...kkEivg mirgciktvt
{aac(6?):Citrobacter} ............. ............. ...mnyqlvni aEcsnYqlea aniLteaFnd lgnnswpDmt satkevkeci
Consensus            ------------ ------------ ------------ -----V-L--- ---E------ ---F------ ---DD----- ---------

81
{rimJ: E.coli}       gminefhkqg safyfglFdp dekeiigvan fsnvvrgsfh aCylgYsIgq kwqGkGlmfe aLtaairymq rtqhihrima
{rimI: E.coli}       gnv.mlhqrg yakmfmiF.. kedeLigvis f.nrieplnk taeigYwlde shQqGqGlisq aLqaLihhyA qsgeIrrfvi
{N3nat: Pseudomonas} etFiAlaafd rgtaiggLA. ......... ......... iYlydLaVas sHRrlGVata LishLkr.vA veIGayviyv
{Nnat: E.coli}       ktFiAlaafd qeavgaLA.. .aYVLpkfeq arse..... ......... iYlydLaVsg eHRrqGlata LinlLkh.eA nalGayviyv
{nat1: Streptomyces} rtFvAygd.. ....dgdLA. .aYVLpkfeq arse..... ......... ItVedieVap LMglate.fA gerGaghlwL
{sat: Streptomyces}  rtFvAvga.. ....dgdLA. .GFVvisysa wnrr..... ......... ItledieVap LMrhaad.fA rerGaghlwL
{sat: E.coli}        acYgAf.i.. ....dqeLv. .GFaavsysa wnqr..... ......... ItlediaVsh Liefakk.wA lsrqllgirL
{ssat: Mouse}        ehWtp..... eghsivgFA. .Gkleln.st wndl..... ......... aslehivVsh tHRqKGVahs Liefakk.wA lsrqllgirL
{ssat: Human}        ehWtp..... eghsivgFA. .mYFtydpw igkl..... ......... lYledFFVms dyRGFGlGse iLknLsq.vA mkcrcssmhF
```

FIG. 15A

| FIG. 15 |
|---------|
| FIG. 15A |
| FIG. 15B |

```
{ssat: Human}            ehWtp...... eghsivgFA.. .mYyFtydpw igkl........ lYledFfVms dyRGfGlGse iLknLsq.vA mrcrcssmhF
{tab: Pseudomonas}       lwvA...... eddnvlasA.. .qsLcqkpn glnr........ oeVqkLmVlp saRgRrGlGrq LMdeveq.vA vkhkrgllhL
{lat: Azospirillum}      rfLvA...... rrsgtvvgc.. .Galaidteg gy......... geVkrmfVqp taRGgqlGrr LLeried.eA raaGlsallL
{ard1: Yeast}            dgrtikldpt ylapgekLv.. .GYVLvkmnd dpdqneppn ghltsLsVmr tyRrmGlaen LMrqalfalr evhqaeyvsL
{MAK3: Yeast}            gtpnip..... ........i. .Gclvckmd. ..phrnvrlr gYlgmLaVes tyRGhGlakk Lveiaidkmq rehcde.imL
{HLS1: Arabidopsis}      cggkldlnhk ...sqndv.. .kplYtkl.. ............ aYVlgLrVsp fHRrqGlGfk LvkmMeewfr q.nGaeysyi
{aac(6'): Citrobacter}   espnlcfgll innslvgWi.. .GLrpmyket we......... ..hpLvVrp dyqnkGlGki LLkeLenr.A reqGiigiaL
Consensus                --F-A----  ------- -- -GYVL----- ---------- -YL--L-V-- -HRG-GlG-- LL--L----A ---G----L 161                                                                                         240
{rimJ: E.coli}           nymph.....N krsgdLLarl GFekeGyakd yllidgqWrd hvltaLttpd wtpgr............ fthrrlke neekleddle
{riml: E.coli}           kcrvd.....N pqsnqvalrn GFileGclkq aefIndaYdd vnlYariids q.................lyirfst teff......
{N3nat: Pseudomomas}     qadyg.....d dPAVaLYtkl Gvredvmhfd idprtat... ..................
{Nnat: E.coli}           qadyg.....d dPAVaLYtkl Gireevmhfd idpstat... ..................
{nat1: Streptomyces}     evtnv.....N aPAlhaYrrm GFtlcGldta lydgtasdge rqaLYMsmpc p.................
{sat: Streptomyces}      evtnv.....N aPAlhaYrrm GFafcGldsa lyqgtasege .haLYMsmpc p.................
{etqtn: E.coli}          etqtn.....N vPAcnlYakc GFtlgGidlf tyktrpqvsn etamYwywfs gaqdda............
{lvaew: Mouse}           lvaew.....N ePslnFYkrr Gasdlsseeg w......rLfk idkeYLlkma aee...............
{ssat: Human}            lvaew.....N ePslnFYkrr Gasdlsseeg w......rLfk idkeYLlkma tee...............
{tab: Pseudomonas}       dtea......g svAeaFYsal aYtrvGelpg ycatpdgrlh ptaiYFktlg qpt...............
{lat: Azospirillum}      etgvy.....q atrlaLYrkq GFadrGpfgp ygpdplsLfm ekpL.............
{ard1: Yeast}            hvrqs.....N raAlhLYrdt lafevls... .ieksyyqdg edaYaMkkvl kleelqisn. .pltesksctrs tflmhgrlat
{MAK3: Yeast}            eteve.....N saAlnLY.eg mgfirmk... .rmfryyLne gdaFkL..il ..............klepvdaet. ..lyirfst teff
{HLS1: Arabidopsis}      atend.....N qasVnLFtgk cgysefrtps ilvnpvyahr vnvsrrvtvi klepvdaet. iwmwkslike ............
{aac(6'): Citrobacter}   gtddeyyrts lslltitedn iFdsiknikn inkhpyeFyq kngYYivgii pnangknkpd iwmwkslike ............
Consensus                ----------N -PAI-LY--- GF-----G-- ---------- -------L-- -----YL---
```

FIG. 15B

EIN3 cDNA

```
TCTTCTTCTTCTTCCTCTTCCTCATCTCGTATCTCTAACTTTTGTCGAAGTTCT
TTTGATGAAACTAGGGTTTATTATCTTCTCCTTCTTTTTCCCATCACCATAGAA
AAGGCAGAGACCTTTTTCTTCATCATTTTTATTCTCCTTCTTCTTCTGCTGT
TCATTTCTCCAGGTTACAATGATGTTTAATGAGATGGGAATGTGTGGAAACAT
GGATTTCTTCTCTTCTGGATCACTTGGTGAAGTTGATTTCTGTCCTGTTCCACA
AGCTGAGCCTGATTCCATTGTTGAAGATGACTATACTGATGATGAGATTGATG
TTGATGAATTGGAGAGGAGGATGTGGAGAGACAAAATGCGGCTTAAACGTCT
CAAGGAGCAGGATAAGGGTAAAGAAGGTGTTGATGCTGCTAAACAGAGGCA
GTCTCAAGAGCAAGCTAGGAGGAAGAAAATGTCTAGAGCTCAAGATGGGATC
TTGAAGTATATGTTGAAGATGATGGAAGTTTGTAAAGCTCAAGGCTTTGTTTAT
GGGATTATTCCGGAGAATGGGAAGCCTGTGACTGGTGCTTCTGATAATTTAAG
GGAGTGGTGGAAAGATAAGGTTAGGTTTGATCGTAATGGTCCTGCGGCTATTA
CCAAGTATCAAGCGGAGAATAATATCCCGGGGATTCATGAAGGTAATAACCC
GATTGGACCGACTCCTCATACCTTGCAAGAGCTTCAAGACACGACTCTTGGA
TCGCTTTTGTCTGCGTTGATGCAACACTGTGATCCTCCTCAGAGACGTTTTCC
TTTGGAGAAAGGAGTTCCTCCTCCGCGGTGGCCTAATGGGAAAGAGGATTGG
TGGCCTCAACTTGGTTTGCCTAAAGATCAAGGTCCTGCACCTTACAAGAAGC
CTCATGATTTGAAGAAGGCGTGGAAAGTCGGCGTTTTGACTGCGGTTATCAA
GCATATGTTTCCTGATATTGCTAAGATCCGTAAGCTCGTGAGGCAATCTAAAT
GTTTGCAGGATAAGATGACTGCTAAAGAGAGTGCTACCTGGCTTGCTATTATT
AACCAAGAAGAGTCCTTGGCTAGAGAGCTTTATCCCGAGTCATGTCCACCTC
TTTCTCTGTCTGGTGGAAGTTGCTCGCTTCTGATGAATGATTGCAGTCAATAC
GATGTTGAAGGTTTCGAGAAGGAGTCTCACTATGAAGTGGAAGAGCTCAAGC
CAGAAAAAGTTATGAATTCTTCAAACTTTGGGATGGTTGCTAAAATGCATGAC
TTTCCTGTCAAAGAAGAAGTCCCAGCAGGAAACTCGGAATTCATGAGAAAGA
GAAAGCCAAACAGAGATCTGAACACTATTATGGACAGAACCGTTTTCACCTG
CGAGAATCTTGGGTGTGCGCACAGCGAAATCAGCCGGGGATTTCTGGATAG
GAATTCGAGAGACAACCATCAACTGGCATGTCCACATCGAGACAGTCGCTTA
CCGTATGGAGCAGCACCATCCAGGTTTCATGTCAATGAAGTTAAGCCTG
TAGTTGGATTTCCTCAGCCAAGGCCAGTGAACTCAGTAGCCCAACCAATTGA
CTTAACGGGTATAGTTCCTGAAGATGGACAGAAGATGATCTCAGAGCTCATG
TCCATGTACGACAGAAATGTCCAGAGCAACCAAACCTCTATGGTCATGGAAA
ATCAAAGCGTGTCACTGCTTCAACCCACAGTCCATAACCATCAAGAACATCT
CCAGTTCCCAGGAAACATGGTGGAAGGAAGTTTCTTTGAAGACTTGAACATC
CCAAACAGAGCAAACAACAACAACAGCAGCAACAATCAAACGTTTTTTCAAG
GGAACAACAACAACAACAATGTGTTTAAGTTCGACACTGCAGATCACAACAA
CTTTGAAGCTGCACATAACAACAACAATAACAGTAGCGGCAACAGGTTCCAG
CTTGTGTTTGATTCCACACCGTTCGACATGGCGTCATTCGATTACAGAGATGA
TATGTCGATGCCAGGAGTAGTAGGAACGATGGATGGAATGCAGCAGAAGCA
GC.AAGATGTATCCATATGGTTCTAAAGTCTTGGTAGTAGATTTCATCTTCTCTT
ATTTTTATCTTTTGTGTTCTTACATTCACTCAACCATGTAATATTTTTCCTGGG
TCTCTCTGTCTCTATCGCTTGTTATGATGTGTCTGTAAGAGTCTCTAAAAACTC
TCTGTTACTGTGTGTCTTTGTCTCGGCTTGGTGAATCTCTCTGTCATCATCAG
CTTTTAGTTACACACCCGACTTGGGGATGAACGAACACTAAATGTAAGTTTTC
A
```

FIG. 19A

EIN3 genomic

```
AGAGCAGTGAGTATTNCCACNAGCCGCTTTGTTAATTACATATTAATTGTGTA
ATAATAATAATAAATGATGTCTTAAATTTTATGTGTAAGAAATGAAATTAAAATG
ATATATATGTATATTATATATCTANACATATATATATATATATAAATAGAGTATAT
ATACTATGATCTATCTTCCTGATCTACAGAGAGACTCCACAAAGAAACGCAAA
TAAACAAAAGTCGCTTTCTAGCCACGTGATCTTTCGTCGACTTTTCTTCTTCTT
CTTCTTCTTCCTCTTCCTCATCTCGTATCTCTAACTTTTGTCGAAGTTCTTTTG
ATGAAACTAGGGTTTATTATCTTCTCCTTCTTTTTCCCATCACCATAGAAAAGG
CAGAGACCTTTTTCTTCATCATTTTTATTCTCCTTCTTCTTCTGCTGTTCATTTC
TCCAGGTACTATACGCTTCTTCTTCTATTGATTTTTTAGGGTTATTATTGATACT
GAAGATGATGATAGGTTTATTCATAGGGTTTTACTAGATCGATGGTTTTACTTT
AGTTTACTAGTGTTTACACGATCTAATTTCATGAGTTTATNCTACTTTTAGTTTT
TTNTTTGGGTGAAGTTTTGTTTATTGTTTATAAATCGTTGATCTATTTGAAAATG
TTTTCTCTTTCTTATTCATATATGATCCTTTCTATATTTGGTTCCTATGTTGAAG
ATCTCATCCTTTTTTTGGAAATTGAATCTGTTGATAATTTTTATTATCCGATTGA
TTATTTAGTTTAGGAGTGATTAAAATACGATCTGATTATGTGTTTATTACTTAAA
ACTTTGATTGAATTCGAAAAGCCCCTTTTTTATAATTTAGGGTTTGATGATTTTT
TTTAGTAAGTTGTTTGATTCAGAAGAAATATAATTGTACTGATTAGTTTTGTTTG
TGTATTTGATTTGTTACAGGTTACAATGATGTTTAATGAGATGGGAATGTGTGG
AAACATGGATTTCTTCTCTTCTGGATCACTTGGTGAAGTTGATTTCTGTCCTGT
TCCACAAGCTGAGCCTGATTCCATTGTTGAAGATGACTATACTGATGATGAGA
TTGATGTTGATGAATTGGAGAGGAGGATGTGGAGAGACAAAATGCGGCTTAA
ACGTCTCAAGGAGCAGGATAAGGGTAAAGAAGGTGTTGATGCTGCTAAACAG
AGGCAGTCTCAAGAGCAAGCTAGGAGGAAGAAAATGTCTAGAGCTCAAGATG
GGATCTTGAAGTATATGTTGAAGATGATGGAAGTTTGTAAAGCTCAAGGCTTT
GTTTATGGGATTATTCCGGAGAATGGGAAGCCTGTGACTGGTGCTTCTGATAA
TTTAAGGGAGTGGTGGAAAGATAAGGTTAGGTTTGATCGTAATGGTCCTGCGG
CTATTACCAAGTATCAAGCGGAGAATAATATCCCGGGGATTCATGAAGGTAAT
AACCCGATTGGACCGACTCCTCATACCTTGCAAGAGCTTCAAGACACGACT
CTTGGATCGCTTTTGTCTGCGTTGATGCAACACTGTGATCCTCCTCAGAGAC
GTTTTCCTTTGGAGAAAGGAGTTCCTCCTCCGTGGTGGCCTAATGGGAAAGA
GGATTGGTGGCCTCAACTTGGTTTGCCTAAAGATCAAGGTCCTGCACCTTAC
AAGAAGCCTCATGATTTGAAGAAGGCGTGGAAAGTCGGCGTTTTGACTGCGG
TTATCAAGCATATGTTTCCTGATATTGCTAAGATCCGTAAGCTCGTGAGGCAA
TCTAAATGTTTGCAGGATAAGATGACTGCTAAAGAGAGTGCTACCTGGCTTGC
TATTATTAACCAAGAAGAGTCCTTGGCTAGAGAGCTTTATCCCGAGTCATGTC
```

*FIG. 19B*

```
CACCTCTTTCTCTGTCTGGTGGAAGTTGCTCGCTTCTGATGAATGATTGCAGT
CAATACGATGTTGAAGGTTTCGAGAAGGAGTCTCACTATGAAGTGGAAGAGC
TCAAGCCAGAAAAAGTTATGAATTCTTCAAACTTTGGGATGGTTGCTAAAATG
CATGACTTTCCTGTCAAAGAAGAAGTCCCAGCAGGAAACTCGGAATTCATGA
GAAAGAGAAAGCCAAACAGAGATCTGAACACTATTATGGACAGAACCGTTTT
CACCTGCGAGAATCTTGGGTGTGCGCACAGCGAAATCAGCCGGGGATTTCT
GGATAGGAATTCGAGAGACAACCATCAACTGGCATGTCCACATCGAGACAGT
CGCTTACCGTATGGAGCAGCACCATCCAGGTTTCATGTCAATGAAGTTAAGC
CTGTAGTTGGATTTCCTCAGCCAAGGCCAGTGAACTCAGTAGCCCAACCAAT
TGACTTAACGGGTATAGTTCCTGAAGATGGACAGAAGATGATCTCAGAGCTC
ATGTCCATGTACGACAGAAATGTCCAGAGCAACCAAACCTCTATGGTCATGG
AAAATCAAAGCGTGTCACTGCTTCAACCCACAGTCCATAACCATCAAGAACA
TCTCCAGTTCCCAGGAAACATGGTGGAAGGAAGTTTCTTTGAAGACTTGAAC
ATCCCAAACAGAGCAAACAACAACAACAGCAGCAACAATCAAACGTTTTTTC
AAGGGAACAACAACAACAACAATGTGTTTAAGTTCGACACTGCAGATCACAA
CAACTTTGAAGCTGCACATAACAACAACAATAACAGTAGCGGCAACAGGTTC
CAGCTTGTGTTTGATTCCACACCGTTCGACATGGCGTCATTCGATTACAGAG
ATGATATGTCGATGCCAGGAGTAGTAGGAACGATGGATGGAATGCAGCAGAA
GCAGCAAGATGTATCCATATGGTTCTAAAGTCTTGGTAGTAGATTTCATCTTCT
CTTATTTTTATCTTTTGTGTTCTTACATTCACTCAACCATGTAATATTTTTTCCT
GGGTCTCTCTGTCTCTATCGCTTGTTATGATGTGTCTGTAAGAGTCTCTAAAA
ACTCTCTGTTACTGTGTGTCTTTGTCTCGGCTTGGTGAATCTCTCTGTCATCAT
CAGCTTTTAGTTACACACCCGACTTGGGGATGAACGAACACTAAATGTAAGTT
TTCATAATATAAATATATTTGNAAGCTCTCTTCTTCTGTGTGTTTTGGTTGAGTT
TGACTTTTACAATTGAAAAGTTTGGTGTAATTCACGCTAACTACCTCAAAGTTA
GGGAATGGTGGGATAATTATTTATTACAATTGTATTTGATGGATAACGTGCTTA
TCGCTAGTGGCTCGCGGGTAGCATTTAAGCATGGGTCAATGCTTGTGTCTAC
GAGCTCGAGTGATCGAGCACACACAATCCAATCCGAACACAAAACAAGAAG
AAAAACAAAATAAGATCTTAGATGTAAGGNATTCTTAAAT
```

*FIG. 19C*

EIN3 peptide

MMFNEMGMCGNMDFFSSGSLGEVDFCPVPQAEPDSIVEDDYTDDEIDVDELE
RRMWRDKMRLKRLKEQDKGKEGVDAAKQRQSQEQARRKKMSRAQDGILKYM
LKMMEVCKAQGFVYGIIPENGKPVTGASDNLREWWKDKVRFDRNGPAAITKYQ
AENNIPGIHEGNNPIGPTPHTLQELQDTTLGSLLSALMQHCDPPQRRFPLEKGV
PPPWWPNGKEDWWPQLGLPKDQGPAPYKKPHDLKKAWKVGVLTAVIKHMFP
DIAKIRKLVRQSKCLQDKMTAKESATWLAIINQEESLARELYPESCPPLSLSGG
SCSLLMNDCSQYDVEGFEKESHYEVEELKPEKVMNSSNFGMVAKMHDFPVK
EEVPAGNSEFMRKRKPNRDLNTIMDRTVFTCENLGCAHSEISRGFLDRNSRDN
HQLACPHRDSRLPYGAAPSRFHVNEVKPVVGFPQPRPVNSVAQPIDLTGIVPE
DGQKMISELMSMYDRNVQSNQTSMVMENQSVSLLQPTVHNHQEHLQFPGN
MVEGSFFEDLNIPNRANNNNSSNNQTFFQGNNNNNNVFKFDTADHNNFEAAH
NNNNNSSGNRFQLVFDSTPFDMASFDYRDDMSMPGVVGTMDGMQQKQQDV
SIWF

*FIG. 19D*

EIL1 cDNA

```
GGCCGCTTCAAACTCTACAAACCCAGAAACCACCACACAGTAATTAATGTCT
CTTTCTTTCTTCCCATGTGATCTTTAACAGACTTTTCTTCTTATTCTCCATCTC
TGAAGTtGTGGGGATTCATCAAGACTTCCTTATCTGTTTCTTTTATAAAACAA
GAGAGAGATACCACTTTTGGTGTTCTTTATTTGCAACTCTTTCAGGTTAAAGA
AATCGATAGGCTCTGTTCTTGATTGTGGTGGAAGAGAcATGATGATGTTTaAC
GAGATGGGAATGTATGGAAACATGGATTTCTTCTCTtCCTCCACATCTCTCGA
tGTGtGtccATTACCACAAGCTGAACAAGAACCTGTagtTGAagaTGTCGACTACA
CCGATGATGAGATGGATGAGCTTGAGCAGAGGATGTGGAGAGACAAAATGC
GTTTGAAACGTCTCAAGGAGCAACAGAGTAAGTGTAAAGGAGGCGTCGATg
GTTCGAAACAGAGGCAGTcgCaAGAGCAAGCTAGGAGGAAGAAAAtgtCTAGA
GCCCAAGATGGGATCTTGAAGTATATGTTGAAGATGAtGGAAGTTTGTAAAG
CTCAAGGCTTTGTTTATGGTATTATTCCTGAGAAGGGTAAGCCTGTGACTGG
tGCTTCGGATaATTTGAGGGAATGGTgGAAAGATAAGGTTAGGTTTGATCGTA
ATGGTCCAgCTGCTATTGCTAAGTATCAGtCAGAGAATaATATTTCTGGAGGG
AGTAATGATTGTAACAGCTTGGTTGGTCCAACACcgcATACGcTTCAGGAGCT
TCAGGACACGACTCTTGGTTCgCTTTTATCGGCTTTGATGCAACATTGTGAT
CCACCGCAGAGACGGTTTCCTTTGgaGAAaGGAGTTTCTcCACCTTGGTGGC
CTAATGGGAATGAAGAgtgGTGGccTcaGCTtgGtTTACCAAATGAGCAAGGTCC
TCCTCCTTATAAGAAGCCTCATGATTTGAAGAAAGCTTGGAAAgTCGGTGTTT
TaACTGCGGTGATCAAGCATATgTCGCCGGATATTGCGAAGATCCGTAAGCT
TGTGAGGCAATCAAAATGCTTgCAGGATAAGATGACGGCGAAAGAGAGTGC
TACTTGGCTTGCCATTATTAACCAAGAAGAGGTTGTGGCTCGGGAgCTTTAT
CCCGAGTCATGCCCTCCTCTTTCTTCTTCTTCATCATTAGGAAGCGGGTCGC
TtcTCATTAATGATTGTAGCGAGTATGACGTTGaAGGTTTCGAGAAGGaACaA
CATGGTTTCGATGTGGaAGAGCGGAAACCAGAGATAGTGATGATgCATCCTC
TAgCAAGCTTTGGGGTTgCTAAAATGCAACATTTTCCCATAAAGGAGGAGGT
CgCCAcCACGGTAAACTTAGAGTTCACGAGAAAGAGGAAGCAGAACAATGAT
ATGAATGTTATGGTAATGGACAGATCAGcAGGTTACACtTGTGAGaATGGTca
GTGTCCTCACAGCAAAATGAaTCTTGGATTTCAAGACAGGAGTTCAAGGGAC
AACCACCAGATgGTTTGTCCATATAGAGACAATCGTTTAGCGTATGGAGCAT
CCAAGTTTcATATGGGTGGAAtGAAACTAGTAGTTCCTCAGCAAcCAGTCCaa
CCGATCGACcTATCGGGCGTTGGAGTTCCGGAAAACGGGCaGAAGATGAT
CACCGAGCTTATGGCCATGTACGACAGAAATGTCCAAAGCAACCAAACGCC
TCCTACTTTGATGGAAAACCAAAGCATGGTCATTGATGCAAAAGCAGCTCAG
AATCAGCAGCTGAATTTCAACAGTGGCAATCAAATGTTTATGCAACAAGGGA
CGAACAACGGGGTTAACAATCGGTTCCAGATGGTGTTTGATTCGACACCATT
CGATATGGCAGCATTCGATTACAGAGATGATTGGCAAACCGGAGCAATGGA
AGGAATGGGGAAGCAGCAGCAGCAGCAGCAGCAGCAaAGATGTATCA
ATATGGTTCTGAATATTACACAATCTCTGTAATATTCATTCTTTCATAATAACT
CTGTTACCTACTTACCTGACTTGGGTATGTATTCTATTGCACCAAACACTCAT
CTATATTGTTGATGATGATGAAGCCATCTATTTTTTTTTTGTGTCTGAAAGTC
ATTTAACTCGCTTCATTGTTTTAATAATGTCACTATCCATTGAACATCATTCTC
ATGCTACAAGTTTGATTCTTTGAGGCGGCCGC
```

EIL1 peptide

MMMFNEMGMYGNMDFFSSSTSLDVCPLPQAEQEPVVEDVDYTDDEMDVDE
LEKRMWRDKMRLKRLKEQQSKCKEGVDGSKQRQSQEQARRKKMSRAQDGIL
KYMLKMMEVCKAQGFVYGIIPEKGKPVTGASDNLREWWKDKVRFDRNGPAAIA
KYQSENNISGGSNDCNSLVGPTPHTLQELQDTTLGSLLSALMQHCDPPQRRF
PLEKGVSPPWWPNGNEEWWPQLGLPNEQGPPPYKKPHDLKKAWKVGVLTAV
IKHMSPDIAKIRKLVRQSKCLQDKMTAKESATWLAIINQEEVVARELYPESCPPL
SSSSSLGSGSLLINDCSEYDVEGFEKEQHGFDVEERKPEIVMMHPLASFGVA
KMQHFPIKEEVATTVNLEFTRKRKQNNDMNVMVMDRSAGYTCENGQCPHSKM
NLGFQDRSSRDNHQMVCPYRDNRLAYGASKFHMGGMKLVVPQQPVQPIDLS
GVGVPENGQKMITELMAMYDRNVQSNQTPPTLMENQSMVIDAKAAQNQQLNF
NSGNQMFMQQGTNNGVNNRFQMVFDSTPFDMAAFDYRDDWQTGAMEGMGK
QQQQQQQQQQDVSIWF

*FIG. 20B*

EIL2 cDNA

```
CAGATTCTATGGATATGTATAACAACAATATAGGGATGTTCCGGAGTTTAGTTT
GTAGCTCGGCGCCTCCATTTACAGAGGGACATATGTGTTCTGATTCGCATAC
GGCTTTGTGCGATGATCTGAGTAGTGATGAGGAAATGGAAATAGAGGAGCTT
GAGAAGAAGATCTGGAGAGACAAGCAGCGTTTAAAGCGGCTCAAGGAAATG
GCGAAGAACGGTCTAGGAACAAGATTGTTGTTGAAGCAGCAACATGATGATT
TTCCAGAGCACTCTAGTAAGAGAACCATGTACAAGGCACAAGATGGGATCTT
GAAGTACATGTCGAAGACAATGGAGCGATATAAAGCTCAAGGTTTTGTTTATG
GGATTGTGTTAGAGAATGGGAAAACGGTAGCGGGATCTTCTGATAATCTCCG
TGAATGGTGGAAAGACAAAGTGAGGTTTGATAGGAACGGCCCAGCTGCTATA
ATCAAGCACCAAAGGGATATCAATCTTTCTGATGGAAGTGATTCAGGGTCTGA
GGTTGGGGATTCTACCGCACAGAAGTTGCTTGAGCTTCAAGATACTACTCTT
GGAGCTCTGTTATCGGCTCTGTTTCCTCACTGCAACCCTCCTCAGAGGCGGT
TTCCGTTGGAGAAAGGCGTGACACCGCCATGGTGGCCAACGGGGAAAGAAG
ATTGGTGGGATCAACTGTCTTTACCCGTTGATTTTCGAGGTGTTCCGCCACCT
TACAAGAAGCCTCATGATCTCAAGAAGCTGTGGAAAATTGGTGTTTGATTGG
TGTAATCAGACATATGGCTTCTGACATTAGCAACATACCCAATCTCGTGAGAC
GGTCTAGAAGTTTGCAGGAGAAAATGACGTCAAGAGAAGGCGC
TTTATGGCTCGCTGCTCTTTACCGAGAAAAGGCTATTGTTGATCAAATAGCCA
TGTCTAGAGAAAACAACAACACTTCTAACTTTCTTGTTCCTGCAACCGGTGGA
GACCCAGATGTTTTGTTTCCTGAATCTACAGACTATGATGTTGAACTGATTGG
TGGCACTCATCGGACCAATCAGCAGTATCCTGAATTTGAAAACAACTACAAC
TGTGTTTACAAGAGAAAGTTTGAAGAAGATTTTGGGATGCCAATGCATCCAAC
ACTCCTAACATGTGAGAACAGTCTCTGTCCTTATAGCCAACCACATATGGGA
TTTCTTGACAGGAACTTAAGAGAGAATCACCAAATGACTTGTCCTTATAAAGT
CACTTCCTTCTACCAACCAACTAAACCCTATGGTATGACGGGTTTAATGGTTC
CTTGTCCGGATTATAACGGGATGCAGCAGCAGGTTCAGAGCTTTCAAGACCA
GTTTAATCATCCCAACGATCTCTACAGACCAAAAGCTCCACAAAGAGGCAAC
GATGACTTGGTTGAGGATTTGAATCCTTCTCCTTCGACGCTGAATCAGAATCT
TGGTTTAGTCTTACCTACTGACTTCAATGGAGGTGAGGAAACAGTAGGAACA
GAGAACAATCTGCATAATCAAGGGCAAGAGTTGCCCACATCTTGGATTCAGT
AAAGAAAGCTTCAGAGTTTTCTTTTTATGTTTTCTAGTCTTTATAGCTTTGTCTC
TTGCTTATTCTCTCATTAAACACAGTTTTTGATCTCTCCATTTCATAGCCCATG
TAGCAATGGAGAAGATTAGGTTTCATAATAAGTTAATAACCAAATTCAAA
```

EIL2 peptide

```
DSMDMYNNNIGMFRSLVCSSAPPFTEGHMCSDSHTALCDDLSSDEEMEIEEL
EKKIWRDKQRLKRLKEMAKNGLGTRLLLKQQHDDFPEHSSKRTMYKAQDGILK
YMSKTMERYKAQGFVYGIVLENGKTVAGSSDNLREWWKDKVRFDRNGPAAIIK
HQRDINLSDGSDSGSEVGDSTAQKLLELQDTTLGALLSALFPHCNPPQRRFPL
EKGVTPPWWPTGKEDWWDQLSLPVDFRGVPPPYKKPHDLKKLWKIGVLIGVIR
HMASDISNIPNLVRRSRSLQEKMTSREGALWLAALYREKAIVDQIAMSRENNNT
SNFLVPATGGDPDVLFPESTDYDVELIGGTHRTNQQYPEFENNYNCVYKRKFE
EDFGMPMHPTLLTCENSLCPYSQPHMGFLDRNLRENHQMTCPYKVTSFYQPT
KPYGMTGLMVPCPDYNGMQQQVQSFQDQFNHPNDLYRPKAPQRGNDDLVED
LNPSPSTLNQNLGLVLPTDFNGGEETVGTENNLHNQGQELPTSWIQ
```

*FIG. 21B*

EIL3 cDNA

```
TTCCCCTGAGAACGACAGGAGAAAGAATAAAAACCCTAAATTTCTTTAATTTC
GGCGCTTCAGATTATCGTTGTTAAAGGTTTTTGATTGATTTTGTTTAAATGGGC
GATCTTGCTATGTCCGTAGCAGACATCAGGATGGAGAATGAGCCTGATGATT
TAGCTAGTGATAATGTTGCTGAGATTGATGTGAGTGATGAAGAGATTGATGCT
GACGACCTTGAGAGACGGATGTGGAAAGATCGTGTCAGGCTTAAAAGAATCA
AAGAGCGACAAAAAGCTGGCTCTCAAGGAGCTCAAAACGAAGGGAGACACC
TAAGAAAATCTCTGATCAAGCTCAGAGGAAGAAAATGTCTTAGAGCTCAAGAT
GGTATCCTTAAGTACATTGTTGAAGCTTATGGAAGTCTGCAAAGTTCGCGGGT
TTGTCTATGGTATAATACCGGAAAAGGGCAAGCCTGTGAGTTGGCTCCTCTG
ACAATATAAGAGCTTGGTGGAAAGAGAAAGTGAAGTTTGATAAGAaCGGTCCT
GCTGCTATTGCTAAATACGAAGAGGAGTGTTTAGCGTTTGGGAAATCTGATGG
GAATAGGAATTCACAGTTTGTTCTCCAGGATTTGCAAGATGCTACTTTAGGGT
CTTTGTTATCTTCTTTGATGCAACATTGTGATCCTCCTCAAAGGAAGTATCCGT
TGGAGAAAGGGACGCCTCCGCCTTGGTGGCCAACGGGGAATGAAGAATGGT
GGGTGAAACTCGGTCTGCCTAAAAGCCAGAGTCCTCCTTACCGAAAACCTC
ATGATCTCAAGAAGATGTGGAAGGTTGGAGTTTTAACGGCAGTGATCAATCAT
ATGTTACCTGATATTGCAAAGATTAAGAGGCATGTTCGTCAGTCGAAATGTTT
ACAGGACAAGATGACAGCTAAAGAGAGTGCGATTTGGTTGGCGGTTTTGAAC
CAAGAGGAATCTTTGATTCAGCAGCCTAGCAGTGACAATGGAAACTCCAATG
TGACTGAGACACATCGTAGGGGTAATAACGCTGACAGGAGGAAACCTGTGGT
CAACAGTGACAGTGACTATGATGTTGATGGGACAGAGGAAGCTTCAGGTTCA
GTTTCATCTAAAGACAGTAGAAGAAATCAGATTCAAAAAGAACAACCAACAG
CCATCTCACATTCAGTAAGAGATCAAGATAAAGCAGAGAAACATCGCAGAAG
GAAAAGACCTCGAATTAGATCCGGAACTGTCAATCGACAAGAGGAAGAACAA
CCTGAAGCTCAACAAAGAAACATCTTACCTGATATGAATCATGTTGATGCCC
CTCTGCTAGAATATAACATCAACGGTACTCATCAAGAGGACGATGTTGTCGA
CCCAAATATTGCCTTAGGACCAGAGGATaATGgTCTGGAACTAGTGGTTCCTG
AGtTCAATAaCCaaaCATACTTATCTTCCACTTGTTAATGAACAAACTATGATGC
CTGTAGACGAaAGGCCAATGCTTTATGGACCCAAACCCTAACCAAGAGCT
TCAATTTGGGTCAGGGTACAACTTCTACAATCCCTCTGCAGTGTTTGTACATA
ACCAGGAAGACGACATTCTCCATACACAGATAGAAATGAATACACAAGCACC
ACCTCACAACAGTGGGTTCGAGGAGGCCCCAGGAGGAGTACTTCAACCCCT
TGGTTTACTCGGAAATGAAGACGGTGTAACAGGGAGTGAGTTGCCTCAGTAT
CAGAGTGGCATTCTGTCTCCATTGACTGACTTGGACTTTGACTATGGTGGTTT
TGGTGATGATTTCTCATGGTTTGGAGCTTAGTGTCTTGCCATTTTTTTGGGAG
ATTACATAGTTCAAAAGGACATGGCAATAGTCTGGCTAGTACAGTTACTTTCT
CTTCTTCATTTCTTCTGATCTTATATTCTTCCTCTTTTTTTCTTATAATATTTTCT
TAGATTTGTTAAGAGAAACAATTTTCCTTTTGAATAAGTTGCCAGAAGAACTGC
TTTGCCCGTTGTAATGGTCTCTAGGGAAAGCAGTTAGCGTATCATCATTTGTA
AATTTACCTGTGAG
```

*FIG. 22*

HLS1 cDNA:

```
CTCCAACTTTTAAAACTCATCATAAATAGTAAAAAAGTAGCCGGAAAAATAAA
ATAAAAAGTCTATTTCTCTTTCCTTTAAAATCCAAATCCTATAAACTCATAGCT
TTCTCTGTTCTTTACTTATACCTCACGTTATACATATATATAGAGTTTCTATA
AATGCTTCTCTTTCCTCTCGAACAAATCTTCCTCACTTCTCTCATTTCCACAC
TCACCTTCCTCTCTATATATTAAACCCTATCTACTTAACTCTTCTTCTAACTCT
AATCTCTCTCTATTTACTCTGCTTCTGTTCTCACTCTGAAAGAACCAAAAC
ATGACGGTGGTTAGAGAGTACGACCCGACCCGAGACTTAGTCGGCGTGGAG
GACGTGGAACGACGGTGTGAAGTCGGACCAAGCGGCAAGCTTTCTCTTTTCA
CCGACCTTTTGGGTGACCCGATTTGTAGAATCCGACATTCACCTTCCTATCT
CATGCTGGTGGCTGAGATGGGTACGGAGAAGAAGGAGATAGTGGGCATGATT
AGAGGATGTATCAAAACCGTTACATGTGGCCAAAAACTCGATTTAAATCACAA
ATCTCAAAACGATGTCGTTAAGCCTCTTTACACTAAACTCGCTTACGTCTTGG
GCCTTCGCGTCTCTCCTTTTCACAGGAGACAAGGGATTGGGTTTAAGCTCGT
GAAGATGATGGAGGAATGGTTTAGACAAAACGGAGCTGAGTATTCGTATATTG
CAACTGAGAACGATAATCAAGCTTCTGTGAATTTGTTCACCGGGAAATGTGGT
TATTCGGAGTTTCGTACACCGTCGATTTTGGTTAACCCGGTTTACGCTCATCG
AGTTAATGTTTCGCGGCGAGTCACGGTTATCAAGTTAGAGCCGGTTGATGCT
GAGACGTTGTACCGAATCCGGTTTAGCACAACAGAGTTTTTCCCGCGGGATA
TTGATTCGGTACTTAATAACAAACTCTCGCTTGGGACTTTCGTCGCGGTGCCA
CGTGGAAGCTGTTATGGATCCGGGTCTGGATCATGGCCCGGTTCGGCTAAAT
TCCTCGAATATCCACCCGAGTCATGGGCCGTATTAAGCGTGTGGAATTGTAA
AGACTCGTTTCTGTTAGAAGTACGTGGAGCGTCGAGATTGAGACGTGTGGTG
GCTAAAACGACGCGAGTAGTTGATAAAACGTTGCCGTTTCTGAAACTACCTT
CGATACCGTCCGTTTTCGAACCTTTTGGACTTCATTTTATGTATGGAATCGGA
GGAGAAGGTCCACGCGCGGTGAAGATGGTGAAATCCTTGTGTGCTCACGCG
CATAACTTGGCTAAGGCAGGTGGTTGTGGTGTCGTGGCGGCGGAAGTTGCC
GGAGAAGACCCGTTGCGGCGAGGAATACCACATTGGAAAGTGCTATCGTGT
GACGAGGATCTTTGGTGTATAAAGCGGCTTGGAGATGACTATAGTGATGGTGT
TGTTGGTGATTGGACTAAATCGCCACCTGGCGTTTCCATTTTTGTAGACCCT
AGAGAATTTTAAAACTTTTTTTTAACTCTATAATATATATTCTCTATTAACCACT
TGATGTTAAATTAGGGGTTTTCTTCTAAGTTTATAGATTTTCTTGTTTTAGAATTA
ATCTTTTTTTTAGGTAACTTTTTTGCTTTTTGTTTTGTTTTGTTTTGTTTTGTGG
GTGTTATAAATTA
```

HLS1 genomic sequence:

tgtcataatcagtacaaaataaatcacctaccaacctgaactatatgttatatattttgaggggccacgtcaagtgt
gccgtttattttgtgtttatgattgtttaatatttgtgcgtgtgatggtgtttcttgcttagtttccacttaatacacaatc
aaatatcaagtggaactatttatgaaaattgttcttcgagaagaattctgacccctaaaaggtcatttgagggcttg
aggcttattgtttccaaattacaccagtaaacaaggggttttttttgtcaacaaagattattgtaattcgaatttcgtcta
caataaaacaattttcttactaaaacaaaacaattagctgacggttgatatttcggcttttgagttttaattaactaatt
ggtgattatgttgatgatctttcacacctaatgaagtgtcatgtatatgtatatatgtatatacttatgtatatataaaac
gtacatataatcatttgtcatatatatcatcatgtattgcatgactaaactacccttaaaagaggaatacgatagac
atgacctttaggaatttgttttttcttctdaaatggattccttcgcttcttttagcctcgtagtgaatttgaacattgcagttat
ttctagtaagatattttttctgtattttcggaaaatgttaaaaactaattatacacaatttactttctctctcaactct
tattttacgttactgttttttttttcctcttgcaaaattagagctgatgtatttacatttactagtaatttggtagatag
acagttaatgtagtatatagatgggttgagggcaaatgattacttgggagatggtgcaatgcatcagagtgat
gatgtggaatttaataagtgtgaatttatgggcaaaggaagggaactagtagtagaaagggaaataaatac
agtacaagtaagaggaaaacgaaaagagagatagaaaccataataatgagttaacgcagacatagccg
ccattttcaacttctcactcccacttacaacttctccttctgggcaagttttccacatcaatgctcgtcttaatcaccatta
atctctactcatcattaatacgttgaagcccactatttcaaaatttactaggagtatttattcgtgaaaaacatttaaat
gtccctaattataagagatttaatttcatatttattgtattaaagagaatttacattagctgtcaaaaaaaaaaaaaa
aagagaattaacattatttacagaacataaaattttgaaaatagatagcgccactgcatgtaagaacatacaa
atttctttttttcaacaaaatctatttatatttcttctttttttgaacattatgtgtagtttgtagtaaactaaaaagtgtggacc
aacacaatttaaatcattcgattttgtagcaaaaacatttttgttccaatttccaagcagcaaatatggaaggaata
taaattctttactattttttcctcttaacacataaaagtaaaaaaagcattcaatgatcagttaaaatctggttagaattc
taccttatcatttagaactagctaatatttaaattcatatatacaaaaaataaaatgggaactgtagagactagag
actataaatagaggattgagaagaagaacttttaaagctctatcaatcatgaactactcgccttCTCCAACT
TTTAAAACTCATCATAAATAGTAAAAAAGTAGCCGGAAAAATAAAATAAAAAGT
CTATTTCTCTTTCCTTTAAAATCCAAATCCTATAAACTCATAGCTTTCTCTGTT
CTTTACTTATACCTCACGTTATACATATATATAGAGTTTCTATAAATGCTTCTCT
TTCCTCTCGAACAAATCTTCCTCACTTCTCTCATTTCCACACTCACCTTCCTC
TCTATATATTAAACCCTATCTACTTAACTCTTCTTCTAACTCTAATCTCTCTCT
CTATTTACTCTGCTTCTGTTCTCACTCTGAAAGAACCAAAACATGACGGTGGT
TAGAGAGTACGACCCGACCCGAGACTTAGTCGGCGTGGAGGACGTGGAACG
ACGGTGTGAAGTCGGACCAAGCGGCAAGCTTTCTCTTTTCACCGACCTTTTG
GGTGACCCGATTTGTAGAATCCGACATTCACCTTCCTATCTCATGCTGGgtaata
acatgtttcacaatcttttatcttcttttacttgtatgtctcttcaaaaactctgtttgtttttgaacctagaagtagaaaaca
tagaacaccaacttctcaacctttggttaatccaaaaaaacccattttccataaacaattaaagttcggttcttttttgg
tatcatttctattttttccgattcttgataagatcaaaagactcatcatttatattattttttgcaaccaaatgatacccga
gtaactataactaataaagtttcctctttattataaaaggttaaaaacatataataacggaaaatttaaattatggg
actgtaacagGTGGCTGAGATGGGTACGGAGAAGAAGGAGATAGTGGGCATGAT
TAGAGGATGTATCAAAACCGTTACATGTGGCCAAAAACTCGATTTAAATCACA
AATCTCAAAACGATGTCGTTAAGCCTCTTTACACTAAACTCGCTTACGTCTTG
GGCCTTCGCGTCTCTCCTTTTCACAGgtacccttccgttttcctcccactcataatcacacgctatt
atagattttggttatctaaactagttttggttttttgcagGAGACAAGGGATTGGGTTTAAGCTCGTG
AAGATGATGGAGGAATGGTTTAGACAAAACGGAGCTGAGTATTCGTATATTGC
AACTGAGAACGATAATCAAGCTTCTGTGAATTTGTTCACCGGGAAATGTGGTT
ATTCGGAGTTTCGTACACCGTCGATTTTGGTTAACCCGGTTTACGCTCATCGA
GTTAATGTTTCGCGGCGAGTCACGGTTATCAAGTTAGAGCCGGTTGATGCTG
AGACGTTGTACCGAATCCGGTTTAGCACAACAGAGTTTTTCCCGCGGGATAT
TGATTCGGTACTTAATAACAAACTCTCGCTTGGGACTTTCGTCGCGGTGCCA

*FIG. 23B*

CGTGGAAGCTGTTATGGATCCGGGTCTGGATCATGGCCCGGTTCGGCTAAAT
TCCTCGAATATCCACCCGAGTCATGGGCCGTATTAAGCGTGTGGAATTGTAA
AGACTCGTTTCTGTTAGAAGTACGTGGAGCGTCGAGATTGAGACGTGTGGTG
GCTAAAACGACGCGAGTAGTTGATAAAACGTTGCCGTTTCTGAAACTACCTT
CGATACCGTCCGTTTTCGAACCTTTTGGACTTCATTTTATGTATGGAATCGGA
GGAGAAGGTCCACGCGCGGTGAAGATGGTGAAATCCTTGTGTGCTCACGCG
CATAACTTGGCTAAGGCAGGTGGTTGTGGTGTCGTGGCGGCGGAAGTTGCC
GGAGAAGACCCGTTGCGGCGAGGAATACCACATTGGAAAGTGCTATCGTGT
GACGAGGATCTTTGGTGTATAAAGCGGCTTGGAGATGACTATAGTGATGGTGT
TGTTGGTGATTGGACTAAATCGCCACCTGGCGTTTCCATTTTTGTAGACCCTA
GAGAATTTTAAAACTTTTTTTTTAACTCTATAATATATATTCTCTATTAACCACTT
GATGTTAAATTAGGGGTTTTCTTCTAAGTTTATAGATTTTCTTGTTTTAGAATTA
ATCTTTTTTTTAGGTAACTTTTTTTTGCTTTTTGTTTTGTTTTGTTTGTTTTGTGG
GTGTTATAAATTAgtggtaagaggtaatatctcctactttttgggtttgtgtcttcttgtcttgtaaatggatctagc
tttttaagatacttttctttgtggccaaaccaaaacgccgacctgattattatttccaagtagataaaatttcatgaac
gcactgatacgtataatgatgcaatttgtgttaagacgatactttggagataaaattacaatatgacaatgataga
aaatgttaccaataacgattagcattatcgtgtgtgccatcaagtataactaagagaaagacgcacatttctttta
agagtaaataaaatatt

*FIG. 23C*

HLS1 polypeptide:

MTVVREYDPTRDLVGVEDVERRCEVGPSGKLSLFTDLLGDPICRIRHSPSYLML
VAEMGTEKKEIVGMIRGCIKTVTCGQKLDLNHKSQNDVVKPLYTKLAYVLGLRV
SPFHRRQGIGFKLVKMMEEWFRQNGAEYSYIATENDNQASVNLFTGKCGYSE
FRTPSILVNPVYAHRVNVSRRVTVIKLEPVDAETLYRIRFSTTEFFPRDIDSVLNN
KLSLGTFVAVPRGSCYGSGSGSWPGSAKFLEYPPESWAVLSVWNCKDSFLL
EVRGASRLRRVVAKTRRVVDKTLPFLKLPSIPSVFEPFGLHFMYGIGGEGPRA
VKMVKSLCAHAHNLAKAGGCGVVAAEVAGEDPLRRGIPHWKVLSCDEDLWCI
KRLGDDYSDGVVGDWTKCHLAFPFL

*FIG. 23D*

SEQUENCE LISTING ( 1 ) GENERAL INFORMATION:

( i i i ) NUMBER OF SEQUENCES: 82

( 2 ) INFORMATION FOR SEQ ID NO:1:

( i ) SEQUENCE CHARACTERISTICS:
        ( A ) LENGTH: 6042 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
TTCTCTCTCT CTCTTTGAAG GTGGCACGAG CACCCATAAC CTTCAGACCT ATAGATACAA    60
ATATGTATGT ATACGTTTTT TATATATAAA TATTTTATAT AATTGATTTT TCGATCTTCT   120
TTTATCTCTC TCTTTCGATG GAACTGAGCT CTTTCTCTCT TTCCTCTTCT TTTCTCTCTC   180
TATCTCTATC TCTCGTAGCT TGATAAGAGT TTCTCTCTTT TGAAGATCCG TTTCTCTCTC   240
TCTCACTGAG ACTATTGTTG TTAGGTCAAC TTGCGATCAT GGCGATTTCG AAGGTGACTT   300
CTTTCAAAAA CCCTAATCCT CTGTTTTTTT TTTATTTTG CTGGGGGCT TTGTACGGAC     360
TTTCATGGGT TTTTGTAGCT TTTCCCTCGG CTTTTGCGCA AATGAGACTT TCTGGGTTTT   420
TTTTCCAGCT TTTTATAATT TCATCAGGTG GATCGAATTC GTAGTTTCAG CTTAGATCTC   480
TCTCCCTCTT CATTATCTGG ACTTTCCAGA CTTGGAGTTC TTCGGGATTG TTTTCGGTTT   540
CTGGGTTTTG TTTTAATTGC GAGATTAAG CTTTTTTCTT TTTTACTACT GTACTTGGTT    600
TGTGGTTGAC CTTTTTTTTC CTTGAAGATC TGAATGCGTA GATCATACGG GATCTTTGCA   660
TTTTTGTTGC TTTTCGTCAG CGTTACGATT CTTTTAGCTT CAGTTTAGTT GAAATTTGTA   720
TTTTTTTTGA GCTTATCTTC TTTTTGTTGC TGCTTCATAC TAAGATCAAT TATTGATTTG   780
TAATACTACT GTATCTGAAG ATTTTCACCA TAAAAAAAAA ATTCAGGTCT GAAGCTGATT   840
TCGAATGGTT TGGAGATATC CGTAGTGGTT AAGCATATGG AAGTCTATGT TCTGCTCTTG   900
GTTGCTCTGT TAGGGCTTCC TCCATTTGGA CCAACTTAGC TGAATGTTGT ATGATCTCTC   960
TCCTTGAAGC AGCAAATAAG AAGAAGGTCT GGTCCTTAAC TTAACATCTG GTTACTAGAG  1020
GAAACTTCAG CTATTATTAG GTAAAGAAAG ACTGTACAGA GTTGTATAAC AAGTAAGCGT  1080
TAGAGTGGCT TTGTTTGCCT CGGTGATAGA AGAACCGACT GATTCGTTGT TGTGTGTTAG  1140
CTTTGGAGGG AATCAGATTT CGCGAGGGAA GGTGTTTTAG ATCAAATCTG TGAATTTTAC  1200
TCAACTGAGG CTTTTAGTGA ACCACGACTG TAGAGTTGAC CTTGAATCCT ACTCTGAGTA  1260
ATTATATTAT CAGATAGATT TAGGATGGAA GCTGAAATTG TGAATGTGAG ACCTCAGCTA  1320
GGGTTTATCC AGAGAATGGT TCCTGCTCTA CTTCCTGTCC TTTTGGTTTC TGTCGGATAT  1380
ATTGATCCCG GGAAATGGGT TGCAAATATC GAAGGAGGTG CTCGTTTCGG GTATGACTTG  1440
GTGGCAATTA CTCTGCTTTT CAATTTGCC GCCATCTTAT GCCAATATGT TGCAGCTCGC   1500
ATAAGCGTTG TGACTGGTAA ACACTTGGCT CAGGTAAACA TTTTCTGAT CTCTAAAGAG   1560
CAAACTTTTT AAAATAACAA ACTGGGCTCT GTGGTTGTCT TGTCACTTTC TCAAAGTGGA  1620
ATTCTACTAA CCACCTTCTC TATTTTTCTA ACATTTTAAT GTTCTTTACT GGGACAGATC  1680
```

```
TGCAATGAAG AATATGACAA GTGGACGTGC ATGTTCTTGG GCATTCAGGC GGAGTTCTCA  1740
GCAATTCTGC TCGACCTTAC CATGGTAGTT ACTACAATT  CTTGCTGTT  CTTAATTTTT  1800
TTATTATGTA GTAAAATTTT GATTCCTCTG ACTGAGCTT  CTCTATTATA AACAGGTTGT  1860
GGGAGTTGCG CATGCACTTA ACCTTTTGTT TGGGGTGGAG TTATCCACTG GAGTGTTTTT  1920
GGCCGCCATG GATGCGTTTT TATTTCCTGT TTTCGCCTCT TTCCTTGTAG TTACTTACAA  1980
TTCTTTGCTG TTCTTAATTT TTTTATTATG TAGTAAAATT TTGATTCCTC TGACTTGAGC  2040
TTCTCTATTA TAAACAGGAA AATGGTATGG CAAATACAGT ATCCATTTAC TCTGCAGGCC  2100
TGGTATTACT TCTCTATGTA TCTGGCGTCT TGCTGAGTCA GTCTGAGATC CCACTCTCTA  2160
TGAATGGAGT GTTAACTCGG TTAAATGGAG AGAGCGCATT CGCACTGATG GGTCTTCTTG  2220
GCGCAAGCAT CGTCCCTCAC AATTTTTATA TCCATTCTTA TTTGCTGGG  GTACCTTTTT  2280
TCTCTTTATA TGTATCTCTC TTCTCTGTTA AGAAGCAATA ATTATACTAA GCAGTGAACG  2340
CTCTATTACA GGAAAGTACA TCTTCGTCTG ATGTCGACAA GAGCAGCTTG TGTCAAGACC  2400
ATTTGTTCGC CATCTTGGT  GTCTTCAGCG GACTGTCACT TGTAAATTAT GTATTGATGA  2460
ATGCAGCAGC TAATGTGTTT CACAGTACTG GCCTTGTGGT ACTGACTTTT CACGATGCCT  2520
TGTCACTAAT GGAGCAGGTT TGTTCTGACG GTTTATGTT  CGTATTAGTC AATAATTCAT  2580
TTTTAGGGAA AATGTTCAGA AATCTCTCGT GATTATTAAT TATCTTGTTC TTGATTGTTG  2640
ATCACAGGTA TTTATGAGTC CGCTCATTCC AGTGGTCTTT TGATGCTCT  TGTTCTTCTC  2700
TAGTCAAATT ACCGCACTAG CTTGGGCTTT CGGTGGAGAG GTCGTCCTGC ATGACTTCCT  2760
GAAGATAGAA ATACCCGCTT GGCTTCATCG TGCTACAATC AGAATTCTTG CAGTTGCTCC  2820
TGCGCTTTAT TGTGTATGGA CATCTGGTGC AGACGGAATA TACCAGTTAC TTATATTCAC  2880
CCAGGTCTTG GTGGCAATGA TGCTTCCTTG CTCGGTAATA CCGCTTTTCC GCATTGCTTC  2940
GTCGAGACAA ATCATGGGTG TCCATAAAAT CCCTCAGGTT GGCGAGTTCC TCGCACTTAC  3000
AACGTTTTTG GGATTCTGG  GGTTGAATGT TGTTTTTGTT GTTGAGATGG TATTTGGGAG  3060
CAGTGACTGG GCTGGTGGTT TGAGATGGAA TACCGGTATG GGCACCTCGA TTCAGTACAC  3120
CACTCTGCTT GTATCGTCAT GTGCATCCTT ATGCCTGATA CTCTGGCTGG CAGCCACGCC  3180
GCTGAAATCT GCGAGTAACA GAGCGGAAGC TCAAATATGG AACATGGATG CTCAAAATGC  3240
TTATCTTAT  CCATCTGTTC AAGAAGAGGA AATTGAAAGA ACAGAAACAA GGAGGAACGA  3300
AGACGAATCA ATAGTGCGGT TGGAAAGCAG GGTAAGGAT  CAGTTGGATA CTACGTCTGT  3360
TACTAGCTCG GTCTATGATT TGCCAGAGAA CATTCTAATG ACGGATCAAG AAATCCGTTC  3420
GAGCCCTCCA GAGGAAAGAG AGTTGGATGT AAAGTACTCT ACCTCTCAAG TTAGTAGTCT  3480
TAAGGAAGAC TCTGATGTAA AGGAACAGTC TGTATTGCAG TCAACAGTGG TTAATGAGGT  3540
CAGTGATAAG GATCTGATTG TTGAAACAAA GATGGCGAAA ATTGAACCAA TGAGTCCTGT  3600
GGAGAAGATT GTTAGCATGG AGAATAACAG CAAGTTTATT GAAAAGGATG TTGAAGGGGT  3660
TTCATGGGAA ACAGAAGAAG CTACCAAAGC TGCTCCTACA AGCAACTTTA CTGTCGGATC  3720
TGATGGTCCT CCTTCATTCC GCAGCTTAAG TGGGGAAGGG GGAAGTGGGA CTGGAAGCCT  3780
TTCACGGTTG CAAGGTTTGG GACGTGCTGC CCGGAGACAC TTATCTGCGA TCCTTGATGA  3840
ATTTGGGGA  CATTTATATG ATTTTCATGG GCAATTGGTT GCTGAAGCCA GGGCAAGAA   3900
ACTAGATCAG CTGTTTGGCA CTGATCAAAA GTCAGCCTCT TCTATGAAAG CAGATTCGTT  3960
TGGAAAAGAC ATTAGCAGTG GATATTGCAT GTCACCAACT GCGAAGGGAA TGGATTCACA  4020
GATGACTTCA AGTTTATATG ATTCACTGAA GCAGCAGAGG ACACCGGGAA GTATCGATTC  4080
```

| | | | | | | |
|---|---|---|---|---|---|---|
| GTTGTATGGA | TTACAAAGAG | GTTCGTCACC | GTCACCGTTG | GTCAACCGTA | TGCAGATGTT | 4140 |
| GGGTGCATAT | GGTAACACCA | CTAATAATAA | TAATGCTTAC | GAATTGAGTG | AGAGAAGATA | 4200 |
| CTCTAGCCTG | CGTGCTCCAT | CATCTTCAGA | GGGTTGGGAA | CACCAACAAC | CAGCTACAGT | 4260 |
| TCACGGATAC | CAGATGAAGT | CATATGTAGA | CAATTTGGCA | AAAGAAAGGC | TTGAAGCCTT | 4320 |
| ACAATCCCGT | GGAGAGATCC | CGACATCGAG | ATCTATGGCG | CTTGGTACAT | TGAGCTATAC | 4380 |
| ACAGCAACTT | GCTTAGCCT | TGAAACAGAA | GTCCCAGAAT | GGTCTAACCC | CTGGACCAGC | 4440 |
| TCCTGGGTTT | GAGAATTTTG | CTGGGTCTAG | AAGCATATCG | CGACAATCTG | AAAGATCTTA | 4500 |
| TTACGGTGTT | CCATCTTCTG | GCAATACTGA | TACTGTTGGC | GCAGCAGTAG | CCAATGAGAA | 4560 |
| AAAATATAGT | AGCATGCCAG | ATATCTCAGG | ATTGTCTATG | TCCGCAAGGA | ACATGCATTT | 4620 |
| ACCAAACAAC | AAGAGTGGAT | ACTGGGATCC | GTCAAGTGGA | GGAGGAGGGT | ATGGTGCGTC | 4680 |
| TTATGGTCGG | TTAAGCAATG | AATCATCGTT | ATATTCTAAT | TTGGGGTCAC | GGGTGGGAGT | 4740 |
| ACCCTCGACT | TATGATGACA | TTTCTCAATC | AAGAGGAGGC | TACAGAGATG | CCTACAGTTT | 4800 |
| GCCACAGAGT | GCAACAACAG | GGACCGGATC | GCTTTGGTCC | AGACAGCCCT | TTGAGCAGTT | 4860 |
| TGGTGTAGCG | GAGAGGAATG | GTGCTGTTGG | TGAGGAGCTC | AGGAATAGAT | CGAATCCGAT | 4920 |
| CAATATAGAC | AACAACGCTT | CTTCTAATGT | TGATGCAGAG | GCTAAGCTTC | TTCAGTCGTT | 4980 |
| CAGGCACTGT | ATTCTAAAGC | TTATTAAACT | TGAAGGATCC | GAGTGGTTGT | TTGGACAAAG | 5040 |
| CGATGGAGTT | GATGAAGAAC | TGATTGACCG | GGTAGCTGCA | CGAGAGAAGT | TTATCTATGA | 5100 |
| AGCTGAAGCT | CGAGAAATAA | ACCAGGTGGG | TCACATGGGG | GAGCCACTAA | TTTCATCGGT | 5160 |
| TCCTAACTGT | GGAGATGGTT | GCGTTTGGAG | AGCTGATTTG | ATTGTGAGCT | TGGAGTTTG | 5220 |
| GTGCATTCAC | CGTGTCCTTG | ACTTGTCTCT | CATGGAGAGT | CGGCCTGAGC | TTTGGGGAAA | 5280 |
| GTACACTTAC | GTTCTCAACC | GCCTACAGGG | TAACAAAAAC | CGCAGTAGTT | CATTGAAAAT | 5340 |
| CACAGTTTTG | CAGTTTGAAA | ATATTGACAT | GTATGGATTT | AAACAGGAGT | GATTGATCCG | 5400 |
| GCGTTCTCAA | AGCTGCGGAC | ACCAATGACA | CCGTGCTTTT | GCCTTCAGAT | TCCAGCGAGC | 5460 |
| CACCAGAGAG | CGAGTCCGAC | TTCAGCTAAC | GGAATGTTAC | CTCCGGCTGC | AAAACCGGCT | 5520 |
| AAAGGCAAAT | GCACAACCGC | AGTCACACTT | CTTGATCTAA | TCAAAGACGT | TGAAATGGCA | 5580 |
| ATCTCTTGTA | GAAAAGGCCG | AACCGGTACA | GCTGCAGGTG | ATGTGGCTTT | CCCAAAGGGG | 5640 |
| AAAGAGAATT | TGGCTTCGGT | TTCGAAGCGG | TATAAACGTC | GGTTATCGAA | TAAACCAGTA | 5700 |
| AGGTATGAAT | CAGGATGGAC | CCGGTTCAAG | AAAAAACGTG | ACTGCGTACG | GATCATTGGG | 5760 |
| TTGAAGAAGA | AGAACATTGT | GAGAAATCTC | ATGATCAAAG | TGACGTCGAG | AGGGAAGCCG | 5820 |
| AAGAATCAAA | ACTCTCGCTT | TTGATTGCTC | CTCTGCTTCG | TTAATTGTGT | ATTAAGAAAA | 5880 |
| GAAGAAAAAA | AATGGATTTT | TGTTGCTTCA | GAATTTTTCG | CTCTTTTTT | CTTAATTTGG | 5940 |
| TTGTAATGTT | ATGTTTATAT | ACATATATCA | TCATCATAGG | ACCATAGCTA | CAAACCGAAT | 6000 |
| CCGGTTTGTG | TAATTCTATG | CGGAATCATA | AGAAATCGT | CG | | 6042 |

( 2 ) INFORMATION FOR SEQ ID NO:2:

( i ) SEQUENCE CHARACTERISTICS:
        ( A ) LENGTH: 4747 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

```
CTTTTCTCTC TCTATCTCTA TCTCTCGTAG CTTGATAAGA GTTCTCTCT  TTTGAAGATC     60
CGTTTCTCTC TCTCTCACTG AGACTATTGT TGTTAGGTCA ACTTGCGATC ATGGCGATTT    120
CGAAGGTCTG AAGCTGATTT CGAATGGTTT GGAGATATCC GTAGTGGTTA AGCATATGGA    180
AGTCTATGTT CTGCTCTTGG TTGCTCTGTT AGGGCTTCCT CCATTTGGAC CAACTTAGCT    240
GAATGTTGTA TGATCTCTCT CCTTGAAGCA GCAAATAAGA AGAAGGTCTG GTCCTTAACT    300
TAACATCTGG TTACTAGAGG AAACTTCAGC TATTATTAGG TAAAGAAAGA CTGTACAGAG    360
TTGTATAACA AGTAAGCGTT AGAGTGGCTT TGTTTGCCTC GGTGATAGAA GAACCGACTG    420
ATTCGTTGTT GTGTGTTAGC TTTGGAGGGA ATCAGATTTC GCGAGGGAAG GTGTTTAGA    480
TCAAATCTGT GAATTTACT  CAACTGAGGC TTTTAGTGAA CCACGACTGT AGAGTTGACC    540
TTGAATCCTA CTCTGAGTAA TTATATTATC AGATAGATTT AGGATGGAAG CTGAAATTGT    600
GAATGTGAGA CCTCAGCTAG GGTTATCCA  GAGAATGGTT CCTGCTCTAC TTCCTGTCCT    660
TTTGGTTTCT GTCGGATATA TTGATCCCGG GAAATGGGTT GCAAATATCG AAGGAGGTGC    720
TCGTTTCGGG TATGACTTGG TGGCAATTAC TCTGCTTTTC AATTTTGCCG CCATCTTATG    780
CCAATATGTT GCAGCTCGCA TAAGCGTTGT GACTGGTAAA CACTTGGCTC AGATCTGCAA    840
TGAAGAATAT GACAAGTGGA CGTGCATGTT CTTGGGCATT CAGGCGGAGT TCTCAGCAAT    900
TCTGCTCGAC CTTACCATGG TTGTGGGAGT TGCGCATGCA CTTAACCTTT TGTTTGGGGT    960
GGAGTTATCC ACTGGAGTGT TTTTGGCCGC CATGGATGCG TTTTTATTTC CTGTTTTCGC   1020
CTCTTTCCTT GAAAATGGTA TGGCAAATAC AGTATCCATT TACTCTGCAG GCCTGGTATT   1080
ACTTCTCTAT GTATCTGGCG TCTTGCTGAG TCAGTCTGAG ATCCCACTCT CTATGAATGG   1140
AGTGTTAACT CGGTTAAATG GAGAGAGCGC ATTCGCACTG ATGGGTCTTC TTGGCGCAAG   1200
CATCGTCCCT CACAATTTTT ATATCCATTC TTATTTGCT  GGGGAAAGTA CATCTTCGTC   1260
TGATGTCGAC AAGAGCAGCT TGTGTCAAGA CCATTGTTC  GCCATCTTTG GTGTCTTCAG   1320
CGGACTGTCA CTTGTAAATT ATGTATTGAT GAATGCAGCA GCTAATGTGT TCACAGTAC    1380
TGGCCTTGTG GTACTGACTT TTCACGATGC CTTGTCACTA ATGGAGCAGG TATTTATGAG   1440
TCCGCTCATT CCAGTGGTCT TTTTGATGCT CTTGTTCTTC TCTAGTCAAA TTACCGCACT   1500
AGCTTGGGCT TTCGGTGGAG AGGTCGTCCT GCATGACTTC CTGAAGATAG AAATACCCGC   1560
TTGGCTTCAT CGTGCTACAA TCAGAATTCT TGCAGTTGCT CCTGCGCTTT ATTGTGTATG   1620
GACATCTGGT GCAGACGGAA TATACCAGTT ACTTATATTC ACCCAGGTCT TGGTGGCAAT   1680
GATGCTTCCT TGCTCGGTAA TACCGCTTTT CCGCATTGCT TCGTCGAGAC AAATCATGGG   1740
TGTCCATAAA ATCCCTCAGG TTGGCGAGTT CCTCGCACTT ACAACGTTTT TGGGATTTCT   1800
GGGGTTGAAT GTTGTTTTTG TTGTTGAGAT GGTATTTGGG AGCAGTGACT GGGCTGGTGG   1860
TTTGAGATGG AATACCGGTA TGGGCACCTC GATTCAGTAC ACCACTCTGC TTGTATCGTC   1920
ATGTGCATCC TTATGCCTGA TACTCTGGCT GGCAGCCACG CCGCTGAAAT CTGCGAGTAA   1980
CAGAGCGGAA GCTCAAATAT GGAACATGGA TGCTCAAAAT GCTTTATCTT ATCCATCTGT   2040
TCAAGAAGAG GAAATTGAAA GAACAGAAAC AAGGAGGAAC GAAGACGAAT CAATAGTGCG   2100
GTTGGAAAGC AGGGTAAAGG ATCAGTTGGA TACTACGTCT GTTACTAGCT CGGTCTATGA   2160
TTTGCCAGAG AACATTCTAA TGACGGATCA AGAAATCCGT TCGAGCCCTC CAGAGGAAAG   2220
AGAGTTGGAT GTAAAGTACT CTACCTCTCA AGTTAGTAGT CTTAAGGAAG ACTCTGATGT   2280
AAAGGAACAG TCTGTATTGC AGTCAACAGT GGTTAATGAG GTCAGTGATA AGGATCTGAT   2340
```

```
TGTTGAAACA AAGATGGCGA AAATTGAACC AATGAGTCCT GTGGAGAAGA TTGTTAGCAT    2400
GGAGAATAAC AGCAAGTTTA TTGAAAAGGA TGTTGAAGGG GTTCATGGG AAACAGAAGA     2460
AGCTACCAAA GCTGCTCCTA CAAGCAACTT TACTGTCGGA TCTGATGGTC CTCCTTCATT    2520
CCGCAGCTTA AGTGGGGAAG GGGAAGTGG GACTGGAAGC CTTTCACGGT TGCAAGGTTT     2580
GGGACGTGCT GCCCGGAGAC ACTTATCTGC GATCCTTGAT GAATTTTGGG GACATTATA    2640
TGATTTTCAT GGGCAATTGG TTGCTGAAGC CAGGGCAAAG AAACTAGATC AGCTGTTTGG    2700
CACTGATCAA AAGTCAGCCT CTTCTATGAA AGCAGATTCG TTTGGAAAAG ACATTAGCAG    2760
TGGATATTGC ATGTCACCAA CTGCGAAGGG AATGGATTCA CAGATGACTT CAAGTTTATA    2820
TGATTCACTG AAGCAGCAGA GGACACCGGG AAGTATCGAT TCGTTGTATG GATTACAAAG    2880
AGGTTCGTCA CCGTCACCGT TGGTCAACCG TATGCAGATG TTGGGTGCAT ATGGTAACAC    2940
CACTAATAAT AATAATGCTT ACGAATTGAG TGAGAGAAGA TACTCTAGCC TGCGTGCTCC    3000
ATCATCTTCA GAGGGTTGGG AACACCAACA ACCAGCTACA GTTCACGGAT ACCAGATGAA    3060
GTCATATGTA GACAATTTGG CAAAAGAAAG GCTTGAAGCC TTACAATCCC GTGGAGAGAT    3120
CCCGACATCG AGATCTATGG CGCTTGGTAC ATTGAGCTAT ACACAGCAAC TTGCTTTAGC    3180
CTTGAAACAG AAGTCCCAGA ATGGTCTAAC CCCTGGACCA GCTCCTGGGT TGAGAATTT    3240
TGCTGGGTCT AGAAGCATAT CGCGACAATC TGAAAGATCT TATTACGGTG TTCCATCTTC    3300
TGGCAATACT GATACTGTTG GCGCAGCAGT AGCCAATGAG AAAAAATATA GTAGCATGCC    3360
AGATATCTCA GGATTGTCTA TGTCCGCAAG GAACATGCAT TTACCAAACA ACAAGAGTGG    3420
ATACTGGGAT CCGTCAAGTG GAGGAGGAGG GTATGGTGCG TCTTATGGTC GGTTAAGCAA    3480
TGAATCATCG TTATATTCTA ATTTGGGGTC ACGGGTGGGA GTACCCTCGA CTTATGATGA    3540
CATTTCTCAA TCAAGAGGAG GCTACAGAGA TGCCTACAGT TTGCCACAGA GTGCAACAAC    3600
AGGGACCGGA TCGCTTTGGT CCAGACAGCC CTTTGAGCAG TTTGGTGTAG CGGAGAGGAA    3660
TGGTGCTGTT GGTGAGGAGC TCAGGAATAG ATCGAATCCG ATCAATATAG ACAACAACGC    3720
TTCTTCTAAT GTTGATGCAG AGGCTAAGCT TCTTCAGTCG TTCAGGCACT GTATTCTAAA    3780
GCTTATTAAA CTTGAAGGAT CCGAGTGGTT GTTTGGACAA AGCGATGGAG TTGATGAAGA    3840
ACTGATTGAC CGGGTAGCTG CACGAGAGAA GTTTATCTAT GAAGCTGAAG CTCGAGAAAT    3900
AAACCAGGTG GGTCACATGG GGAGCCACT AATTTCATCG GTTCCTAACT GTGGAGATGG     3960
TTGCGTTTGG AGAGCTGATT TGATTGTGAG CTTTGGAGTT TGGTGCATTC ACCGTGTCCT    4020
TGACTTGTCT CTCATGGAGA GTCGGCCTGA GCTTGGGGA AAGTACACTT ACGTTCTCAA     4080
CCGCCTACAG GGAGTGATTG ATCCGGCGTT CTCAAAGCTG CGGACACCAA TGACACCGTG    4140
CTTTTGCCTT CAGATTCCAG CGAGCCACCA GAGAGCGAGT CCGACTTCAG CTAACGGAAT    4200
GTTACCTCCG GCTGCAAAAC CGGCTAAAGG CAAATGCACA ACCGCAGTCA CACTTCTTGA    4260
TCTAATCAAA GACGTTGAAA TGGCAATCTC TTGTAGAAAA GGCCGAACCG GTACAGCTGC    4320
AGGTGATGTG GCTTTCCCAA AGGGGAAAGA GAATTTGGCT TCGGTTTCGA AGCGGTATAA    4380
ACGTCGGTTA TCGAATAAAC CAGTAAGGTA TGAATCAGGA TGGACCCGGT TCAAGAAAAA    4440
ACGTGACTGC GTACGGATCA TTGGGTTGAA GAAGAAGAAC ATTGTGAGAA ATCTCATGAT    4500
CAAAGTGACG TCGAGAGGGA AGCCGAAGAA TCAAAACTCT CGCTTTTGAT TGCTCCTCTG    4560
CTTCGTTAAT TGTGTATTAA GAAAAGAAGA AAAAAAATGG ATTTTGTTG CTTCAGAATT     4620
TTTCGCTCTT TTTTCTTAA TTTGGTTGTA ATGTTATGTT TATATACATA TATCATCATC    4680
ATAGGACCAT AGCTACAAAC CGAATCCGGT TTGTGTAATT CTATGCGGAA TCATAAAGAA    4740
```

ATCGTCG 4747

(2) INFORMATION FOR SEQ ID NO:3:

(i) SEQUENCE CHARACTERISTICS:
        (A) LENGTH: 1321 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

```
Met  Glu  Ala  Glu  Ile  Val  Asn  Val  Arg  Pro  Gln  Leu  Gly  Phe  Ile  Gln
  1              5                      10                         15

Arg  Met  Val  Pro  Ala  Leu  Leu  Pro  Val  Leu  Leu  Val  Ser  Val  Gly  Tyr
            20                      25                      30

Ile  Asp  Pro  Gly  Lys  Trp  Val  Ala  Asn  Ile  Glu  Gly  Gly  Ala  Arg  Phe
            35                      40                      45

Gly  Tyr  Asp  Leu  Val  Ala  Ile  Thr  Leu  Leu  Phe  Asn  Phe  Ala  Ala  Ile
       50                      55                      60

Leu  Cys  Gln  Tyr  Val  Ala  Ala  Arg  Ile  Ser  Val  Val  Thr  Gly  Lys  His
 65                      70                      75                      80

Leu  Ala  Gln  Ile  Cys  Asn  Glu  Glu  Tyr  Asp  Lys  Trp  Thr  Cys  Met  Phe
                 85                      90                      95

Leu  Gly  Ile  Gln  Ala  Glu  Phe  Ser  Ala  Ile  Leu  Leu  Asp  Leu  Thr  Met
                100                     105                     110

Val  Val  Gly  Val  Ala  His  Ala  Leu  Asn  Leu  Leu  Phe  Gly  Val  Glu  Leu
           115                     120                     125

Ser  Thr  Gly  Val  Phe  Leu  Ala  Ala  Met  Asp  Ala  Phe  Leu  Phe  Pro  Val
      130                     135                     140

Phe  Ala  Ser  Phe  Leu  Glu  Asn  Gly  Met  Ala  Asn  Thr  Val  Ser  Ile  Tyr
145                     150                     155                     160

Ser  Ala  Gly  Leu  Val  Leu  Leu  Leu  Tyr  Val  Ser  Gly  Val  Leu  Leu  Ser
                165                     170                     175

Gln  Ser  Glu  Ile  Pro  Leu  Ser  Met  Asn  Gly  Val  Leu  Thr  Arg  Leu  Asn
                180                     185                     190

Gly  Glu  Ser  Ala  Phe  Ala  Leu  Met  Gly  Leu  Leu  Gly  Ala  Ser  Ile  Val
           195                     200                     205

Pro  His  Asn  Phe  Tyr  Ile  His  Ser  Tyr  Phe  Ala  Gly  Glu  Ser  Thr  Ser
      210                     215                     220

Ser  Ser  Asp  Val  Asp  Lys  Ser  Ser  Leu  Cys  Gln  Asp  His  Leu  Phe  Ala
225                     230                     235                     240

Ile  Phe  Gly  Val  Phe  Ser  Gly  Leu  Ser  Leu  Val  Asn  Tyr  Val  Leu  Met
                245                     250                     255

Asn  Ala  Ala  Ala  Asn  Val  Phe  His  Ser  Thr  Gly  Leu  Val  Val  Leu  Thr
           260                     265                     270

Phe  His  Asp  Ala  Leu  Ser  Leu  Met  Glu  Gln  Val  Phe  Met  Ser  Pro  Leu
      275                     280                     285

Ile  Pro  Val  Val  Phe  Leu  Met  Leu  Leu  Phe  Phe  Ser  Ser  Gln  Ile  Thr
      290                     295                     300

Ala  Leu  Ala  Trp  Ala  Phe  Gly  Gly  Glu  Val  Val  Leu  His  Asp  Phe  Leu
305                     310                     315                     320
```

```
Lys  Ile  Glu  Ile  Pro  Ala  Trp  Leu  His  Arg  Ala  Thr  Ile  Arg  Ile  Leu
               325                 330                           335

Ala  Val  Ala  Pro  Ala  Leu  Tyr  Cys  Val  Trp  Thr  Ser  Gly  Ala  Asp  Gly
               340                 345                      350

Ile  Tyr  Gln  Leu  Leu  Ile  Phe  Thr  Gln  Val  Leu  Val  Ala  Met  Met  Leu
          355                      360                           365

Pro  Cys  Ser  Val  Ile  Pro  Leu  Phe  Arg  Ile  Ala  Ser  Ser  Arg  Gln  Ile
     370                      375                      380

Met  Gly  Val  His  Lys  Ile  Pro  Gln  Val  Gly  Glu  Phe  Leu  Ala  Leu  Thr
385                      390                      395                           400

Thr  Phe  Leu  Gly  Phe  Leu  Gly  Leu  Asn  Val  Val  Phe  Val  Val  Glu  Met
                    405                      410                           415

Val  Phe  Gly  Ser  Ser  Asp  Trp  Ala  Gly  Gly  Leu  Arg  Trp  Asn  Thr  Gly
               420                      425                      430

Met  Gly  Thr  Ser  Ile  Gln  Tyr  Thr  Thr  Leu  Leu  Val  Ser  Ser  Cys  Ala
          435                      440                      445

Ser  Leu  Cys  Leu  Ile  Leu  Trp  Leu  Ala  Ala  Thr  Pro  Leu  Lys  Ser  Ala
     450                      455                 460

Ser  Asn  Arg  Ala  Glu  Ala  Gln  Ile  Trp  Asn  Met  Asp  Ala  Gln  Asn  Ala
465                           470                 475                           480

Leu  Ser  Tyr  Pro  Ser  Val  Gln  Glu  Glu  Ile  Glu  Arg  Thr  Glu  Thr
                    485                      490                      495

Arg  Arg  Asn  Glu  Asp  Glu  Ser  Ile  Val  Arg  Leu  Glu  Ser  Arg  Val  Lys
               500                      505                 510

Asp  Gln  Leu  Asp  Thr  Thr  Ser  Val  Thr  Ser  Ser  Val  Tyr  Asp  Leu  Pro
          515                      520                      525

Glu  Asn  Ile  Leu  Met  Thr  Asp  Gln  Glu  Ile  Arg  Ser  Ser  Pro  Pro  Glu
     530                      535                      540

Glu  Arg  Glu  Leu  Asp  Val  Lys  Tyr  Ser  Thr  Ser  Gln  Val  Ser  Ser  Leu
545                      550                      555                           560

Lys  Glu  Asp  Ser  Asp  Val  Lys  Glu  Gln  Ser  Val  Leu  Gln  Ser  Thr  Val
               565                      570                           575

Val  Asn  Glu  Val  Ser  Asp  Lys  Asp  Leu  Ile  Val  Glu  Thr  Lys  Met  Ala
               580                      585                      590

Lys  Ile  Glu  Pro  Met  Ser  Pro  Val  Glu  Lys  Ile  Val  Ser  Met  Glu  Asn
          595                      600                      605

Asn  Ser  Lys  Phe  Ile  Glu  Lys  Asp  Val  Glu  Gly  Val  Ser  Trp  Glu  Thr
     610                      615                      620

Glu  Glu  Ala  Thr  Lys  Ala  Ala  Pro  Thr  Ser  Asn  Phe  Thr  Val  Gly  Ser
625                      630                      635                           640

Asp  Gly  Pro  Pro  Ser  Phe  Arg  Ser  Leu  Ser  Gly  Glu  Gly  Gly  Ser  Gly
                    645                      650                      655

Thr  Gly  Ser  Leu  Ser  Arg  Leu  Gln  Gly  Leu  Gly  Arg  Ala  Ala  Arg  Arg
               660                      665                      670

His  Leu  Ser  Ala  Ile  Leu  Asp  Glu  Phe  Trp  Gly  His  Leu  Tyr  Asp  Phe
          675                      680                      685

His  Gly  Gln  Leu  Val  Ala  Glu  Ala  Arg  Ala  Lys  Lys  Leu  Asp  Gln  Leu
     690                      695                 700

Phe  Gly  Thr  Asp  Gln  Lys  Ser  Ala  Ser  Ser  Met  Lys  Ala  Asp  Ser  Phe
705                      710                      715                           720

Gly  Lys  Asp  Ile  Ser  Ser  Gly  Tyr  Cys  Met  Ser  Pro  Thr  Ala  Lys  Gly
               725                      730                      735

Met  Asp  Ser  Gln  Met  Thr  Ser  Ser  Leu  Tyr  Asp  Ser  Leu  Lys  Gln  Gln
               740                      745                      750
```

| | | | | | | | | | | | | | | |
|---|---|---|---|---|---|---|---|---|---|---|---|---|---|---|
|Arg|Thr|Pro|Gly|Ser|Ile|Asp|Ser|Leu|Tyr|Gly|Leu|Gln|Arg|Gly|Ser|
| | |755| | | |760| | | |765| | | | |
|Ser|Pro|Ser|Pro|Leu|Val|Asn|Arg|Met|Gln|Met|Leu|Gly|Ala|Tyr|Gly|
| |770| | | |775| | | |780| | | | | |
|Asn|Thr|Thr|Asn|Asn|Asn|Asn|Ala|Tyr|Glu|Leu|Ser|Glu|Arg|Arg|Tyr|
|785| | | | |790| | | |795| | | | |800|
|Ser|Ser|Leu|Arg|Ala|Pro|Ser|Ser|Ser|Glu|Gly|Trp|Glu|His|Gln|Gln|
| | | | |805| | | |810| | | | |815| |
|Pro|Ala|Thr|Val|His|Gly|Tyr|Gln|Met|Lys|Ser|Tyr|Val|Asp|Asn|Leu|
| | |820| | | | |825| | | | |830| | |
|Ala|Lys|Glu|Arg|Leu|Glu|Ala|Leu|Gln|Ser|Arg|Gly|Glu|Ile|Pro|Thr|
| | |835| | | | |840| | | |845| | | |
|Ser|Arg|Ser|Met|Ala|Leu|Gly|Thr|Leu|Ser|Tyr|Thr|Gln|Gln|Leu|Ala|
| |850| | | | |855| | | |860| | | | |
|Leu|Ala|Leu|Lys|Gln|Lys|Ser|Gln|Asn|Gly|Leu|Thr|Pro|Gly|Pro|Ala|
|865| | | | |870| | | |875| | | | |880|
|Pro|Gly|Phe|Glu|Asn|Phe|Ala|Gly|Ser|Arg|Ser|Ile|Ser|Arg|Gln|Ser|
| | | | |885| | | |890| | | | |895| |
|Glu|Arg|Ser|Tyr|Tyr|Gly|Val|Pro|Ser|Ser|Gly|Asn|Thr|Asp|Thr|Val|
| | | |900| | | |905| | | |910| | | |
|Gly|Ala|Ala|Val|Ala|Asn|Glu|Lys|Lys|Tyr|Ser|Ser|Met|Pro|Asp|Ile|
| | |915| | | |920| | | |925| | | | |
|Ser|Gly|Leu|Ser|Met|Ser|Ala|Arg|Asn|Met|His|Leu|Pro|Asn|Asn|Lys|
| |930| | | |935| | | |940| | | | | |
|Ser|Gly|Tyr|Trp|Asp|Pro|Ser|Ser|Gly|Gly|Gly|Tyr|Gly|Ala|Ser|
|945| | | |950| | | |955| | | | |960|
|Tyr|Gly|Arg|Leu|Ser|Asn|Glu|Ser|Ser|Leu|Tyr|Ser|Asn|Leu|Gly|Ser|
| | | |965| | | |970| | | | |975| | |
|Arg|Val|Gly|Val|Pro|Ser|Thr|Tyr|Asp|Ile|Ser|Gln|Ser|Arg|Gly|
| | |980| | | |985| | | |990| | | | |
|Gly|Tyr|Arg|Asp|Ala|Tyr|Ser|Leu|Pro|Gln|Ser|Ala|Thr|Thr|Gly|Thr|
| | |995| | | |1000| | | |1005| | | | |
|Gly|Ser|Leu|Trp|Ser|Arg|Gln|Pro|Phe|Glu|Gln|Phe|Gly|Val|Ala|Glu|
| |1010| | | |1015| | | |1020| | | | | |
|Arg|Asn|Gly|Ala|Val|Gly|Glu|Glu|Leu|Arg|Asn|Arg|Ser|Asn|Pro|Ile|
|1025| | | |1030| | | |1035| | | | |1040|
|Asn|Ile|Asp|Asn|Asn|Ala|Ser|Ser|Asn|Val|Asp|Ala|Glu|Ala|Lys|Leu|
| | | |1045| | | |1050| | | |1055| | | |
|Leu|Gln|Ser|Phe|Arg|His|Cys|Ile|Leu|Lys|Leu|Ile|Lys|Leu|Glu|Gly|
| | | |1060| | | |1065| | | |1070| | | |
|Ser|Glu|Trp|Leu|Phe|Gly|Gln|Ser|Asp|Gly|Val|Asp|Glu|Glu|Leu|Ile|
| | |1075| | | |1080| | | |1085| | | | |
|Asp|Arg|Val|Ala|Ala|Arg|Glu|Lys|Phe|Ile|Tyr|Glu|Ala|Glu|Ala|Arg|
| |1090| | | |1095| | | |1100| | | | | |
|Glu|Ile|Asn|Gln|Val|Gly|His|Met|Gly|Glu|Pro|Leu|Ile|Ser|Ser|Val|
|1105| | | |1110| | | |1115| | | | |1120|
|Pro|Asn|Cys|Gly|Asp|Gly|Cys|Val|Trp|Arg|Ala|Asp|Leu|Ile|Val|Ser|
| | | |1125| | | |1130| | | |1135| | | |
|Phe|Gly|Val|Trp|Cys|Ile|His|Arg|Val|Leu|Asp|Leu|Ser|Leu|Met|Glu|
| | | |1140| | | |1145| | | |1150| | | |
|Ser|Arg|Pro|Glu|Leu|Trp|Gly|Lys|Tyr|Thr|Tyr|Val|Leu|Asn|Arg|Leu|
| |1155| | | |1160| | | |1165| | | | | |
|Gln|Gly|Val|Ile|Asp|Pro|Ala|Phe|Ser|Lys|Leu|Arg|Thr|Pro|Met|Thr|

|   |   |   |   |   |   |   |   |   |   |   |   |   |   |   |
|---|---|---|---|---|---|---|---|---|---|---|---|---|---|---|
|   |   |   |   | 1170 |   |   |   |   | 1175 |   |   |   | 1180 |   |
| Pro | Cys | Phe | Cys | Leu | Gln | Ile | Pro | Ala | Ser | His | Gln | Arg | Ala | Ser | Pro |
| 1185 |   |   |   |   | 1190 |   |   |   |   | 1195 |   |   |   |   | 1200 |
| Thr | Ser | Ala | Asn | Gly | Met | Leu | Pro | Pro | Ala | Ala | Lys | Pro | Ala | Lys | Gly |
|   |   |   |   |   | 1205 |   |   |   |   | 1210 |   |   |   |   | 1215 |
| Lys | Cys | Thr | Thr | Ala | Val | Thr | Leu | Leu | Asp | Leu | Ile | Lys | Asp | Val | Glu |
|   |   |   |   | 1220 |   |   |   |   | 1225 |   |   |   |   | 1230 |   |
| Met | Ala | Ile | Ser | Cys | Arg | Lys | Gly | Arg | Thr | Gly | Thr | Ala | Ala | Gly | Asp |
|   |   |   |   | 1235 |   |   |   |   | 1240 |   |   |   |   | 1245 |   |
| Val | Ala | Phe | Pro | Lys | Gly | Lys | Glu | Asn | Leu | Ala | Ser | Val | Ser | Lys | Arg |
|   |   |   |   | 1250 |   |   |   |   | 1255 |   |   |   |   | 1260 |   |
| Tyr | Lys | Arg | Arg | Leu | Ser | Asn | Lys | Pro | Val | Arg | Tyr | Glu | Ser | Gly | Trp |
| 1265 |   |   |   |   | 1270 |   |   |   |   | 1275 |   |   |   |   | 1280 |
| Thr | Arg | Phe | Lys | Lys | Lys | Arg | Asp | Cys | Val | Arg | Ile | Ile | Gly | Leu | Lys |
|   |   |   |   | 1285 |   |   |   |   | 1290 |   |   |   |   | 1295 |   |
| Lys | Lys | Asn | Ile | Val | Arg | Asn | Leu | Met | Ile | Lys | Val | Thr | Ser | Arg | Gly |
|   |   |   |   | 1300 |   |   |   |   | 1305 |   |   |   |   | 1310 |   |
| Lys | Pro | Lys | Asn | Gln | Asn | Ser | Arg | Phe |   |   |   |   |   |   |   |
|   |   |   |   | 1315 |   |   |   |   | 1320 |   |   |   |   |   |   |

( 2 ) INFORMATION FOR SEQ ID NO:4:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

| TCTTCTTCTT | CTTCCTCTTC | CTCATCTCGT | ATCTCTAACT | TTTGTCGAAG | TTCTTTTGAT | 60 |
| GAAACTAGGG | TTTATTATCT | TCTCCTTCTT | TTTCCCATCA | CCATAGAAAA | GGCAGAGACC | 120 |
| TTTTTCTTCA | TCATTTTTAT | TCTCCTTCTT | CTTCTGCTGT | TCATTTCTCC | AGGTTACAAT | 180 |
| GATGTTTAAT | GAGATGGGAA | TGTGTGGAAA | CATGGATTTC | TTCTCTTCTG | GATCACTTGG | 240 |
| TGAAGTTGAT | TTCTGTCCTG | TTCCACAAGC | TGAGCCTGAT | TCCATTGTTG | AAGATGACTA | 300 |
| TACTGATGAT | GAGATTGATG | TTGATGAATT | GGAGAGGAGG | ATGTGGAGAG | ACAAAATGCG | 360 |
| GCTTAAACGT | CTCAAGGAGC | AGGATAAGGG | TAAAGAAGGT | GTTGATGCTG | CTAAACAGAG | 420 |
| GCAGTCTCAA | GAGCAAGCTA | GGAGGAAGAA | AATGTCTAGA | GCTCAAGATG | GATCTTGAA | 480 |
| GTATATGTTG | AAGATGATGG | AAGTTTGTAA | AGCTCAAGGC | TTTGTTTATG | GGATTATTCC | 540 |
| GGAGAATGGG | AAGCCTGTGA | CTGGTGCTTC | TGATAATTTA | AGGGAGTGGT | GGAAAGATAA | 600 |
| GGTTAGGTTT | GATCGTAATG | GTCCTGCGGC | TATTACCAAG | TATCAAGCGG | AGAATAATAT | 660 |
| CCCGGGGATT | CATGAAGGTA | ATAACCCGAT | GGACCGACT | CCTCATACCT | TGCAAGAGCT | 720 |
| TCAAGACACG | ACTCTTGGAT | CGCTTTTGTC | TGCGTTGATG | CAACACTGTG | ATCCTCCTCA | 780 |
| GAGACGTTTT | CCTTTGGAGA | AAGGAGTTCC | TCCTCCGCGG | TGGCCTAATG | GAAAGAGGA | 840 |
| TTGGTGGCCT | CAACTTGGTT | TGCCTAAAGA | TCAAGGTCCT | GCACCTTACA | AGAAGCCTCA | 900 |
| TGATTTGAAG | AAGGCGTGGA | AAGTCGGCGT | TTTGACTGCG | GTTATCAAGC | ATATGTTTCC | 960 |
| TGATATTGCT | AAGATCCGTA | AGCTCGTGAG | GCAATCTAAA | TGTTTGCAGG | ATAAGATGAC | 1020 |

-continued

| | | | | | |
|---|---|---|---|---|---|
| TGCTAAAGAG | AGTGCTACCT | GGCTTGCTAT | TATTAACCAA | GAAGAGTCCT | TGGCTAGAGA | 1080 |
| GCTTTATCCC | GAGTCATGTC | CACCTCTTTC | TCTGTCTGGT | GGAAGTTGCT | CGCTTCTGAT | 1140 |
| GAATGATTGC | AGTCAATACG | ATGTTGAAGG | TTTCGAGAAG | GAGTCTCACT | ATGAAGTGGA | 1200 |
| AGAGCTCAAG | CCAGAAAAAG | TTATGAATTC | TTCAAACTTT | GGGATGGTTG | CTAAAATGCA | 1260 |
| TGACTTTCCT | GTCAAGAAG | AAGTCCCAGC | AGGAAACTCG | GAATTCATGA | GAAAGAGAAA | 1320 |
| GCCAAACAGA | GATCTGAACA | CTATTATGGA | CAGAACCGTT | TCACCTGCG | AGAATCTTGG | 1380 |
| GTGTGCGCAC | AGCGAAATCA | GCCGGGGATT | TCTGGATAGG | AATTCGAGAG | ACAACCATCA | 1440 |
| ACTGGCATGT | CCACATCGAG | ACAGTCGCTT | ACCGTATGGA | GCAGCACCAT | CCAGGTTTCA | 1500 |
| TGTCAATGAA | GTTAAGCCTG | TAGTTGGATT | TCCTCAGCCA | AGGCCAGTGA | ACTCAGTAGC | 1560 |
| CCAACCAATT | GACTTAACGG | GTATAGTTCC | TGAAGATGGA | CAGAAGATGA | TCTCAGAGCT | 1620 |
| CATGTCCATG | TACGACAGAA | ATGTCCAGAG | CAACCAAACC | TCTATGGTCA | TGGAAAATCA | 1680 |
| AAGCGTGTCA | CTGCTTCAAC | CCACAGTCCA | TAACCATCAA | GAACATCTCC | AGTTCCCAGG | 1740 |
| AAACATGGTG | GAAGGAAGTT | TCTTTGAAGA | CTTGAACATC | CCAAACAGAG | CAAACAACAA | 1800 |
| CAACAGCAGC | AACAATCAAA | CGTTTTTTCA | AGGGAACAAC | AACAACAACA | ATGTGTTTAA | 1860 |
| GTTCGACACT | GCAGATCACA | ACAACTTTGA | AGCTGCACAT | AACAACAACA | ATAACAGTAG | 1920 |
| CGGCAACAGG | TTCCAGCTTG | TGTTTGATTC | CACACCGTTC | GACATGGCGT | CATTCGATTA | 1980 |
| CAGAGATGAT | ATGTCGATGC | CAGGAGTAGT | AGGAACGATG | GATGGAATGC | AGCAGAAGCA | 2040 |
| GCAAGATGTA | TCCATATGGT | TCTAAAGTCT | TGGTAGTAGA | TTTCATCTTC | TCTTATTTTT | 2100 |
| ATCTTTTGTG | TTCTTACATT | CACTCAACCA | TGTAATATTT | TTCCTGGGT | CTCTCTGTCT | 2160 |
| CTATCGCTTG | TTATGATGTG | TCTGTAAGAG | TCTCTAAAAA | CTCTCTGTTA | CTGTGTGTCT | 2220 |
| TTGTCTCGGC | TTGGTGAATC | TCTCTGTCAT | CATCAGCTTT | TAGTTACACA | CCCGACTTGG | 2280 |
| GGATGAACGA | ACACTAAATG | TAAGTTTTCA | | | | 2310 |

(2) INFORMATION FOR SEQ ID NO:5:

(i) SEQUENCE CHARACTERISTICS:
        (A) LENGTH: 3387 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

| | | | | | |
|---|---|---|---|---|---|
| AGAGCAGTGA | GTATTNCCAC | NAGCCGCTTT | GTTAATTACA | TATTAATTGT | GTAATAATAA | 60 |
| TAATAAATGA | TGTCTTAAAT | TTATGTGTA | AGAAATGAAA | TTAAAATGAT | ATATATGTAT | 120 |
| ATTATATATC | TANACATATA | TATATATATA | TAAATAGAGT | ATATATACTA | TGATCTATCT | 180 |
| TCCTGATCTA | CAGAGAGACT | CCACAAAGAA | ACGCAAATAA | ACAAAGTCG | CTTTCTAGCC | 240 |
| ACGTGATCTT | TCGTCGACTT | TTCTTCTTCT | TCTTCTTCTT | CCTCTTCCTC | ATCTCGTATC | 300 |
| TCTAACTTTT | GTCGAAGTTC | TTTTGATGAA | ACTAGGGTTT | ATTATCTTCT | CCTTCTTTTT | 360 |
| CCCATCACCA | TAGAAAAGGC | AGAGACCTTT | TTCTTCATCA | TTTTTATTCT | CCTTCTTCTT | 420 |
| CTGCTGTTCA | TTTCTCCAGG | TACTATACGC | TTCTTCTTCT | ATTGATTTTT | TAGGGTTATT | 480 |
| ATTGATACTG | AAGATGATGA | TAGGTTTATT | CATAGGGTTT | TACTAGATCG | ATGGTTTTAC | 540 |
| TTTAGTTTAC | TAGTGTTTAC | ACGATCTAAT | TTCATGAGTT | TATNCTACTT | TTAGTTTTTT | 600 |

| | | | | | |
|---|---|---|---|---|---|
| NTTTGGGTGA | AGTTTTGTTT | ATTGTTTATA | AATCGTTGAT | CTATTTGAAA | ATGTTTCTC | 660
| TTTCTTATTC | ATATATGATC | CTTTCTATAT | TTGGTTCCTA | TGTTGAAGAT | CTCATCCTTT | 720
| TTTTGGAAAT | TGAATCTGTT | GATAATTTTT | ATTATCCGAT | TGATTATTTA | GTTAGGAGT | 780
| GATTAAAATA | CGATCTGATT | ATGTGTTTAT | TACTTAAAAC | TTTGATTGAA | TTCGAAAAGC | 840
| CCCTTTTTTA | TAATTTAGGG | TTTGATGATT | TTTTTAGTA | AGTTGTTTGA | TTCAGAAGAA | 900
| ATATAATTGT | ACTGATTAGT | TTTGTTTGTG | TATTTGATTT | GTTACAGGTT | ACAATGATGT | 960
| TTAATGAGAT | GGGAATGTGT | GGAAACATGG | ATTTCTTCTC | TTCTGGATCA | CTTGGTGAAG | 1020
| TTGATTTCTG | TCCTGTTCCA | CAAGCTGAGC | CTGATTCCAT | TGTTGAAGAT | GACTATACTG | 1080
| ATGATGAGAT | TGATGTTGAT | GAATTGGAGA | GGAGGATGTG | GAGAGACAAA | ATGCGGCTTA | 1140
| AACGTCTCAA | GGAGCAGGAT | AAGGGTAAAG | AAGGTGTTGA | TGCTGCTAAA | CAGAGGCAGT | 1200
| CTCAAGAGCA | AGCTAGGAGG | AAGAAATGT | CTAGAGCTCA | AGATGGGATC | TTGAAGTATA | 1260
| TGTTGAAGAT | GATGGAAGTT | TGTAAAGCTC | AAGGCTTTGT | TTATGGGATT | ATTCCGGAGA | 1320
| ATGGGAAGCC | TGTGACTGGT | GCTTCTGATA | ATTTAAGGGA | GTGGTGGAAA | GATAAGGTTA | 1380
| GGTTTGATCG | TAATGGTCCT | GCGGCTATTA | CCAAGTATCA | AGCGGAGAAT | AATATCCCGG | 1440
| GGATTCATGA | AGGTAATAAC | CCGATTGGAC | CGACTCCTCA | TACCTTGCAA | GAGCTTCAAG | 1500
| ACACGACTCT | TGGATCGCTT | TTGTCTGCGT | TGATGCAACA | CTGTGATCCT | CCTCAGAGAC | 1560
| GTTTTCCTTT | GGAGAAAGGA | GTTCCTCCTC | CGTGGTGGCC | TAATGGGAAA | GAGGATTGGT | 1620
| GGCCTCAACT | TGGTTTGCCT | AAAGATCAAG | GTCCTGCACC | TTACAAGAAG | CCTCATGATT | 1680
| TGAAGAAGGC | GTGGAAAGTC | GGCGTTTTGA | CTGCGGTTAT | CAAGCATATG | TTTCCTGATA | 1740
| TTGCTAAGAT | CCGTAAGCTC | GTGAGGCAAT | CTAAATGTTT | GCAGGATAAG | ATGAC TGCTA | 1800
| AAGAGAGTGC | TACCTGGCTT | GCTATTATTA | ACCAAGAAGA | GTCCTTGGCT | AGAGAGCTTT | 1860
| ATCCCGAGTC | ATGTCCACCT | CTTTCTCTGT | CTGGTGGAAG | TTGCTCGCTT | CTGATGAATG | 1920
| ATTGCAGTCA | ATACGATGTT | GAAGGTTTCG | AGAAGGAGTC | TCACTATGAA | GTGGAAGAGC | 1980
| TCAAGCCAGA | AAAAGTTATG | AATTCTTCAA | ACTTTGGGAT | GGTTGCTAAA | ATGCATGACT | 2040
| TTCCTGTCAA | AGAAGAAGTC | CCAGCAGGAA | ACTCGGAATT | CATGAGAAAG | AGAAAGCCAA | 2100
| ACAGAGATCT | GAACACTATT | ATGGACAGAA | CCGTTTTCAC | CTGCGAGAAT | CTTGGGTGTG | 2160
| CGCACAGCGA | AATCAGCCGG | GGATTTCTGG | ATAGGAATTC | GAGAGACAAC | CATCAACTGG | 2220
| CATGTCCACA | TCGAGACAGT | CGCTTACCGT | ATGGAGCAGC | ACCATCCAGG | TTTCATGTCA | 2280
| ATGAAGTTAA | GCCTGTAGTT | GGATTTCCTC | AGCCAAGGCC | AGTGAACTCA | GTAGCCCAAC | 2340
| CAATTGACTT | AACGGGTATA | GTTCCTGAAG | ATGGACAGAA | GATGATCTCA | GAGCTCATGT | 2400
| CCATGTACGA | CAGAAATGTC | CAGAGCAACC | AAACCTCTAT | GGTCATGGAA | AATCAAAGCG | 2460
| TGTCACTGCT | TCAACCCACA | GTCCATAACC | ATCAAGAACA | TCTCCAGTTC | CCAGGAAACA | 2520
| TGGTGGAAGG | AAGTTTCTTT | GAAGACTTGA | ACATCCCAAA | CAGAGCAAAC | AACAACAACA | 2580
| GCAGCAACAA | TCAAACGTTT | TTCAAGGGA | ACAACAACAA | CAACAATGTG | TTTAAGTTCG | 2640
| ACACTGCAGA | TCACAACAAC | TTTGAAGCTG | CACATAACAA | CAACAATAAC | AGTAGCGGCA | 2700
| ACAGGTTCCA | GCTTGTGTTT | GATTCCACAC | CGTTCGACAT | GGCGTCATTC | GATTACAGAG | 2760
| ATGATATGTC | GATGCCAGGA | GTAGTAGGAA | CGATGGATGG | AATGCAGCAG | AAGCAGCAAG | 2820
| ATGTATCCAT | ATGGTTCTAA | AGTCTTGGTA | GTAGATTTCA | TCTTCTCTTA | TTTTTATCTT | 2880
| TTGTGTTCTT | ACATTCACTC | AACCATGTAA | TATTTTTTCC | TGGGTCTCTC | TGTCTCTATC | 2940
| GCTTGTTATG | ATGTGTCTGT | AAGAGTCTCT | AAAAACTCTC | TGTTACTGTG | TGTCTTTGTC | 3000

```
TCGGCTTGGT  GAATCTCTCT  GTCATCATCA  GCTTTTAGTT  ACACACCCGA  CTTGGGGATG    3060

AACGAACACT  AAATGTAAGT  TTTCATAATA  TAAATATATT  TGNAAGCTCT  CTTCTTCTGT    3120

GTGTTTTGGT  TGAGTTTGAC  TTTTACAATT  GAAAAGTTTG  GTGTAATTCA  CGCTAACTAC    3180

CTCAAAGTTA  GGGAATGGTG  GGATAATTAT  TTATTACAAT  TGTATTTGAT  GGATAACGTG    3240

CTTATCGCTA  GTGGCTCGCG  GGTAGCATTT  AAGCATGGGT  CAATGCTTGT  GTCTACGAGC    3300

TCGAGTGATC  GAGCACACAC  AATCCAATCC  GAACACAAAA  CAAGAAGAAA  AACAAAATAA    3360

GATCTTAGAT  GTAAGGNATT  CTTAAAT                                           3387
```

( 2 ) INFORMATION FOR SEQ ID NO:6:

( i ) SEQUENCE CHARACTERISTICS:
        ( A ) LENGTH: 628 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

```
Met Met Phe Asn Glu Met Gly Met Cys Gly Asn Met Asp Phe Phe Ser
 1               5                  10                  15

Ser Gly Ser Leu Gly Glu Val Asp Phe Cys Pro Val Pro Gln Ala Glu
                20                  25                  30

Pro Asp Ser Ile Val Glu Asp Tyr Thr Asp Asp Glu Ile Asp Val
                35                  40                  45

Asp Glu Leu Glu Arg Arg Met Trp Arg Asp Lys Met Arg Leu Lys Arg
        50                  55                  60

Leu Lys Glu Gln Asp Lys Gly Lys Glu Gly Val Asp Ala Ala Lys Gln
 65                 70                  75                  80

Arg Gln Ser Gln Glu Gln Ala Arg Arg Lys Lys Met Ser Arg Ala Gln
                85                  90                  95

Asp Gly Ile Leu Lys Tyr Met Leu Lys Met Met Glu Val Cys Lys Ala
                100                 105                 110

Gln Gly Phe Val Tyr Gly Ile Ile Pro Glu Asn Gly Lys Pro Val Thr
                115                 120                 125

Gly Ala Ser Asp Asn Leu Arg Glu Trp Trp Lys Asp Lys Val Arg Phe
        130                 135                 140

Asp Arg Asn Gly Pro Ala Ala Ile Thr Lys Tyr Gln Ala Glu Asn Asn
145                 150                 155                 160

Ile Pro Gly Ile His Glu Gly Asn Asn Pro Ile Gly Pro Thr Pro His
                165                 170                 175

Thr Leu Gln Glu Leu Gln Asp Thr Thr Leu Gly Ser Leu Leu Ser Ala
                180                 185                 190

Leu Met Gln His Cys Asp Pro Pro Gln Arg Arg Phe Pro Leu Glu Lys
                195                 200                 205

Gly Val Pro Pro Pro Trp Trp Pro Asn Gly Lys Glu Asp Trp Trp Pro
        210                 215                 220

Gln Leu Gly Leu Pro Lys Asp Gln Gly Pro Ala Pro Tyr Lys Lys Pro
225                 230                 235                 240

His Asp Leu Lys Lys Ala Trp Lys Val Gly Val Leu Thr Ala Val Ile
                245                 250                 255
```

```
Lys His Met Phe Pro Asp Ile Ala Lys Ile Arg Lys Leu Val Arg Gln
        260             265             270

Ser Lys Cys Leu Gln Asp Lys Met Thr Ala Lys Glu Ser Ala Thr Trp
        275             280             285

Leu Ala Ile Ile Asn Gln Glu Ser Leu Ala Arg Glu Leu Tyr Pro
        290             295             300

Glu Ser Cys Pro Pro Leu Ser Leu Ser Gly Gly Ser Cys Ser Leu Leu
305             310             315             320

Met Asn Asp Cys Ser Gln Tyr Asp Val Glu Gly Phe Glu Lys Glu Ser
                325             330             335

His Tyr Glu Val Glu Glu Leu Lys Pro Glu Lys Val Met Asn Ser Ser
            340             345             350

Asn Phe Gly Met Val Ala Lys Met His Asp Phe Pro Val Lys Glu Glu
        355             360             365

Val Pro Ala Gly Asn Ser Glu Phe Met Arg Lys Arg Lys Pro Asn Arg
    370             375             380

Asp Leu Asn Thr Ile Met Asp Arg Thr Val Phe Thr Cys Glu Asn Leu
385             390             395             400

Gly Cys Ala His Ser Glu Ile Ser Arg Gly Phe Leu Asp Arg Asn Ser
            405             410             415

Arg Asp Asn His Gln Leu Ala Cys Pro His Arg Asp Ser Arg Leu Pro
        420             425             430

Tyr Gly Ala Ala Pro Ser Arg Phe His Val Asn Glu Val Lys Pro Val
            435             440             445

Val Gly Phe Pro Gln Pro Arg Pro Val Asn Ser Val Ala Gln Pro Ile
    450             455             460

Asp Leu Thr Gly Ile Val Pro Glu Asp Gly Gln Lys Met Ile Ser Glu
465             470             475             480

Leu Met Ser Met Tyr Asp Arg Asn Val Gln Ser Asn Gln Thr Ser Met
            485             490             495

Val Met Glu Asn Gln Ser Val Ser Leu Leu Gln Pro Thr Val His Asn
        500             505             510

His Gln Glu His Leu Gln Phe Pro Gly Asn Met Val Glu Gly Ser Phe
    515             520             525

Phe Glu Asp Leu Asn Ile Pro Asn Arg Ala Asn Asn Asn Asn Ser Ser
    530             535             540

Asn Asn Gln Thr Phe Phe Gln Gly Asn Asn Asn Asn Asn Asn Val Phe
545             550             555             560

Lys Phe Asp Thr Ala Asp His Asn Asn Phe Glu Ala Ala His Asn Asn
            565             570             575

Asn Asn Asn Ser Ser Gly Asn Arg Phe Gln Leu Val Phe Asp Ser Thr
        580             585             590

Pro Phe Asp Met Ala Ser Phe Asp Tyr Arg Asp Asp Met Ser Met Pro
        595             600             605

Gly Val Val Gly Thr Met Asp Gly Met Gln Gln Lys Gln Gln Asp Val
    610             615             620

Ser Ile Trp Phe
625
```

( 2 ) INFORMATION FOR SEQ ID NO:7:

( i ) SEQUENCE CHARACTERISTICS:
        ( A ) LENGTH: 2234 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

| | | | | | | |
|---|---|---|---|---|---|---|
| GGCCGCTTCA | AACTCTACAA | ACCCAGAAAC | CACCACACAG | TAATTAATGT | CTCTTTCTTT | 60 |
| CTTCCCATGT | GATCTTTAAC | AGACTTTTCT | TCTTATTCTC | CATCTCTGAA | GTTGTGGGGA | 120 |
| TTCATCAAGA | CTTCCTTATC | TGTTTCTTTT | ATAAACAAG | AGAGAGATAC | CACTTTTGGT | 180 |
| GTTCTTTATT | TGCAACTCTT | TCAGGTTAAA | GAAATCGATA | GGCTCTGTTC | TTGATTGTGG | 240 |
| TGGAAGAGAC | ATGATGATGT | TAACGAGAT | GGGAATGTAT | GGAAACATGG | ATTTCTTCTC | 300 |
| TTCCTCCACA | TCTCTCGATG | TGTGTCCATT | ACCACAAGCT | GAACAAGAAC | CTGTAGTTGA | 360 |
| AGATGTCGAC | TACACCGATG | ATGAGATGGA | TGAGCTTGAG | CAGAGGATGT | GGAGAGACAA | 420 |
| AATGCGTTTG | AAACGTCTCA | AGGAGCAACA | GAGTAAGTGT | AAAGGAGGCG | TCGATGGTTC | 480 |
| GAAACAGAGG | CAGTCGCAAG | AGCAAGCTAG | GAGGAAGAAA | ATGTCTAGAG | CCCAAGATGG | 540 |
| GATCTTGAAG | TATATGTTGA | AGATGATGGA | AGTTTGTAAA | GCTCAAGGCT | TTGTTTATGG | 600 |
| TATTATTCCT | GAGAAGGGTA | AGCCTGTGAC | TGGTGCTTCG | GATAATTTGA | GGGAATGGTG | 660 |
| GAAAGATAAG | GTTAGGTTTG | ATCGTAATGG | TCCAGCTGCT | ATTGCTAAGT | ATCAGTCAGA | 720 |
| GAATAATATT | TCTGGAGGGA | GTAATGATTG | TAACAGCTTG | GTTGGTCCAA | CACCGCATAC | 780 |
| GCTTCAGGAG | CTTCAGGACA | CGACTCTTGG | TTCGCTTTTA | TCGGCTTTGA | TGCAACATTG | 840 |
| TGATCCACCG | CAGAGACGGT | TTCCTTTGGA | GAAAGGAGTT | TCTCCACCTT | GGTGGCCTAA | 900 |
| TGGGAATGAA | GAGTGGTGGC | CTCAGCTTGG | TTTACCAAAT | GAGCAAGGTC | CTCCTCCTTA | 960 |
| TAAGAAGCCT | CATGATTTGA | AGAAAGCTTG | GAAAGTCGGT | GTTTAACTG | CGGTGATCAA | 1020 |
| GCATATGTCG | CCGGATATTG | CGAAGATCCG | TAAGCTTGTG | AGGCAATCAA | AATGCTTGCA | 1080 |
| GGATAAGATG | ACGGCGAAAG | AGAGTGCTAC | TTGGCTTGCC | ATTATTAACC | AAGAAGAGGT | 1140 |
| TGTGGCTCGG | GAGCTTTATC | CCGAGTCATG | CCCTCCTCTT | TCTTCTTCTT | CATCATTAGG | 1200 |
| AAGCGGGTCG | CTTCTCATTA | ATGATTGTAG | CGAGTATGAC | GTTGAAGGTT | TCGAGAAGGA | 1260 |
| ACAACATGGT | TTCGATGTGG | AAGAGCGGAA | ACCAGAGATA | GTGATGATGC | ATCCTCTAGC | 1320 |
| AAGCTTTGGG | GTTGCTAAAA | TGCAACATTT | TCCCATAAAG | GAGGAGGTCG | CCACCACGGT | 1380 |
| AAACTTAGAG | TTCACGAGAA | AGAGGAAGCA | GAACAATGAT | ATGAATGTTA | TGGTAATGGA | 1440 |
| CAGATCAGCA | GGTTACACTT | GTGAGAATGG | TCAGTGTCCT | CACAGCAAAA | TGAATCTTGG | 1500 |
| ATTTCAAGAC | AGGAGTTCAA | GGGACAACCA | CCAGATGGTT | TGTCCATATA | GAGACAATCG | 1560 |
| TTTAGCGTAT | GGAGCATCCA | AGTTTCATAT | GGGTGGAATG | AAACTAGTAG | TTCCTCAGCA | 1620 |
| ACCAGTCCAA | CCGATCGACC | TATCGGGCGT | TGGAGTTCCG | GAAAACGGGC | AGAAGATGAT | 1680 |
| CACCGAGCTT | ATGGCCATGT | ACGACAGAAA | TGTCCAAAGC | AACCAAACGC | CTCCTACTTT | 1740 |
| GATGGAAAAC | CAAAGCATGG | TCATTGATGC | AAAAGCAGCT | CAGAATCAGC | AGCTGAATTT | 1800 |
| CAACAGTGGC | AATCAAATGT | TTATGCAACA | AGGGACGAAC | AACGGGGTTA | CAATCGGTT | 1860 |
| CCAGATGGTG | TTTGATTCGA | CACCATTCGA | TATGGCAGCA | TTCGATTACA | GAGATGATTG | 1920 |
| GCAAACCGGA | GCAATGGAAG | GAATGGGGAA | GCAGCAGCAG | CAGCAGCAGC | AGCAGCAAAG | 1980 |
| ATGTATCAAT | ATGGTTCTGA | ATATTACACA | ATCTCTGTAA | TATTCATTCT | TTCATAATAA | 2040 |
| CTCTGTTACC | TACTTACCTG | ACTTGGGTAT | GTATTCTATT | GCACCAAACA | CTCATCTATA | 2100 |
| TTGTTGATGA | TGATGAAGCC | ATCTATTTTT | TTTTGTGTC | TGAAAGTCAT | TTAACTCGCT | 2160 |

```
TCATTGTTTT AATAATGTCA CTATCCATTG AACATCATTC TCATGCTACA AGTTTGATTC    2220

TTTGAGGCGG CCGC                                                      2234
```

( 2 ) INFORMATION FOR SEQ ID NO:8:

( i ) SEQUENCE CHARACTERISTICS:
        ( A ) LENGTH: 584 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

```
Met Met Met Phe Asn Glu Met Gly Met Tyr Gly Asn Met Asp Phe Phe
  1           5                  10                  15

Ser Ser Ser Thr Ser Leu Asp Val Cys Pro Leu Pro Gln Ala Glu Gln
             20                  25                  30

Glu Pro Val Val Glu Asp Val Asp Tyr Thr Asp Asp Glu Met Asp Val
             35                  40                  45

Asp Glu Leu Glu Lys Arg Met Trp Arg Asp Lys Met Arg Leu Lys Arg
 50                      55                  60

Leu Lys Glu Gln Gln Ser Lys Cys Lys Glu Gly Val Asp Gly Ser Lys
 65                  70                  75                  80

Gln Arg Gln Ser Gln Glu Gln Ala Arg Arg Lys Lys Met Ser Arg Ala
             85                  90                  95

Gln Asp Gly Ile Leu Lys Tyr Met Leu Lys Met Met Glu Val Cys Lys
            100                 105                 110

Ala Gln Gly Phe Val Tyr Gly Ile Ile Pro Glu Lys Gly Lys Pro Val
            115                 120                 125

Thr Gly Ala Ser Asp Asn Leu Arg Glu Trp Trp Lys Asp Lys Val Arg
130                     135                 140

Phe Asp Arg Asn Gly Pro Ala Ala Ile Ala Lys Tyr Gln Ser Glu Asn
145                     150                 155                 160

Asn Ile Ser Gly Gly Ser Asn Asp Cys Asn Ser Leu Val Gly Pro Thr
                165                 170                 175

Pro His Thr Leu Gln Glu Leu Gln Asp Thr Thr Leu Gly Ser Leu Leu
            180                 185                 190

Ser Ala Leu Met Gln His Cys Asp Pro Pro Gln Arg Arg Phe Pro Leu
            195                 200                 205

Glu Lys Gly Val Ser Pro Pro Trp Trp Pro Asn Gly Asn Glu Glu Trp
210                     215                 220

Trp Pro Gln Leu Gly Leu Pro Asn Glu Gln Gly Pro Pro Pro Tyr Lys
225                     230                 235                 240

Lys Pro His Asp Leu Lys Lys Ala Trp Lys Val Gly Val Leu Thr Ala
                245                 250                 255

Val Ile Lys His Met Ser Pro Asp Ile Ala Lys Ile Arg Lys Leu Val
                260                 265                 270

Arg Gln Ser Lys Cys Leu Gln Asp Lys Met Thr Ala Lys Glu Ser Ala
            275                 280                 285

Thr Trp Leu Ala Ile Ile Asn Gln Glu Glu Val Val Ala Arg Glu Leu
290                     295                 300

Tyr Pro Glu Ser Cys Pro Pro Leu Ser Ser Ser Ser Leu Gly Ser
```

|  |  |  |  |  |  | 305 |  |  |  |  |  | 310 |  |  |  |  |  | 315 |  |  |  |  |  | 320 |
|--|--|--|--|--|--|-----|--|--|--|--|--|-----|--|--|--|--|--|-----|--|--|--|--|--|-----|

```
                      305                         310                         315                         320
        Gly  Ser  Leu  Leu  Ile  Asn  Asp  Cys  Ser  Glu  Tyr  Asp  Val  Glu  Gly  Phe
                                325                         330                         335
        Glu  Lys  Glu  Gln  His  Gly  Phe  Asp  Val  Glu  Glu  Arg  Lys  Pro  Glu  Ile
                                340                         345                         350
        Val  Met  Met  His  Pro  Leu  Ala  Ser  Phe  Gly  Val  Ala  Lys  Met  Gln  His
                                355                         360                         365
        Phe  Pro  Ile  Lys  Glu  Glu  Val  Ala  Thr  Thr  Val  Asn  Leu  Glu  Phe  Thr
                                370                         375                         380
        Arg  Lys  Arg  Lys  Gln  Asn  Asn  Asp  Met  Asn  Val  Met  Val  Met  Asp  Arg
        385                         390                         395                         400
        Ser  Ala  Gly  Tyr  Thr  Cys  Glu  Asn  Gly  Gln  Cys  Pro  His  Ser  Lys  Met
                                405                         410                         415
        Asn  Leu  Gly  Phe  Gln  Asp  Arg  Ser  Ser  Arg  Asp  Asn  His  Gln  Met  Val
                                420                         425                         430
        Cys  Pro  Tyr  Arg  Asp  Asn  Arg  Leu  Ala  Tyr  Gly  Ala  Ser  Lys  Phe  His
                                435                         440                         445
        Met  Gly  Gly  Met  Lys  Leu  Val  Val  Pro  Gln  Gln  Pro  Val  Gln  Pro  Ile
                                450                         455                         460
        Asp  Leu  Ser  Gly  Val  Gly  Val  Pro  Glu  Asn  Gly  Gln  Lys  Met  Ile  Thr
        465                         470                         475                         480
        Glu  Leu  Met  Ala  Met  Tyr  Asp  Arg  Asn  Val  Gln  Ser  Asn  Gln  Thr  Pro
                                485                         490                         495
        Pro  Thr  Leu  Met  Glu  Asn  Gln  Ser  Met  Val  Ile  Asp  Ala  Lys  Ala  Ala
                                500                         505                         510
        Gln  Asn  Gln  Gln  Leu  Asn  Phe  Asn  Ser  Gly  Asn  Gln  Met  Phe  Met  Gln
                                515                         520                         525
        Gln  Gly  Thr  Asn  Asn  Gly  Val  Asn  Asn  Arg  Phe  Gln  Met  Val  Phe  Asp
                                530                         535                         540
        Ser  Thr  Pro  Phe  Asp  Met  Ala  Ala  Phe  Asp  Tyr  Arg  Asp  Asp  Trp  Gln
        545                         550                         555                         560
        Thr  Gly  Ala  Met  Glu  Gly  Met  Gly  Lys  Gln  Gln  Gln  Gln  Gln  Gln  Gln
                                565                         570                         575
        Gln  Gln  Asp  Val  Ser  Ile  Trp  Phe
                                580
```

( 2 ) INFORMATION FOR SEQ ID NO:9:

( i ) SEQUENCE CHARACTERISTICS:
        ( A ) LENGTH: 1722 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

```
CAGATTCTAT  GGATATGTAT  AACAACAATA  TAGGGATGTT  CCGGAGTTTA  GTTTGTAGCT      60
CGGCGCCTCC  ATTTACAGAG  GGACATATGT  GTTCTGATTC  GCATACGGCT  TTGTGCGATG     120
ATCTGAGTAG  TGATGAGGAA  ATGGAAATAG  AGGAGCTTGA  GAAGAAGATC  TGGAGAGACA     180
AGCAGCGTTT  AAAGCGGCTC  AAGGAAATGG  CGAAGAACGG  TCTAGGAACA  AGATTGTTGT     240
TGAAGCAGCA  ACATGATGAT  TTTCCAGAGC  ACTCTAGTAA  GAGAACCATG  TACAAGGCAC     300
```

-continued

```
AAGATGGGAT  CTTGAAGTAC  ATGTCGAAGA  CAATGGAGCG  ATATAAAGCT  CAAGGTTTTG    360
TTTATGGGAT  TGTGTTAGAG  AATGGGAAAA  CGGTAGCGGG  ATCTTCTGAT  AATCTCCGTG    420
AATGGTGGAA  AGACAAAGTG  AGGTTTGATA  GGAACGGCCC  AGCTGCTATA  ATCAAGCACC    480
AAAGGGATAT  CAATCTTTCT  GATGGAAGTG  ATTCAGGGTC  TGAGGTTGGG  GATTCTACCG    540
CACAGAAGTT  GCTTGAGCTT  CAAGATACTA  CTCTTGGAGC  TCTGTTATCG  GCTCTGTTTC    600
CTCACTGCAA  CCCTCCTCAG  AGGCGGTTTC  CGTTGGAGAA  AGGCGTGACA  CCGCCATGGT    660
GGCCAACGGG  GAAAGAAGAT  TGGTGGGATC  AACTGTCTTT  ACCCGTTGAT  TTTCGAGGTG    720
TTCCGCCACC  TTACAAGAAG  CCTCATGATC  TCAAGAAGCT  GTGGAAAATT  GGTGTTTTGA    780
TTGGTGTAAT  CAGACATATG  GCTTCTGACA  TTAGCAACAT  ACCCAATCTC  GTGAGACGGT    840
CTAGAAGTTT  GCAGGAGAAA  ATGACGTCAA  GAGAAGGCGC  TTTATGGCTC  GCTGCTCTTT    900
ACCGAGAAAA  GGCTATTGTT  GATCAAATAG  CCATGTCTAG  AGAAACAAC   AACACTTCTA    960
ACTTTCTTGT  TCCTGCAACC  GGTGGAGACC  CAGATGTTTT  GTTCCTGAA   TCTACAGACT   1020
ATGATGTTGA  ACTGATTGGT  GGCACTCATC  GGACCAATCA  GCAGTATCCT  GAATTTGAAA   1080
ACAACTACAA  CTGTGTTTAC  AAGAGAAAGT  TGAAGAAGA   TTTTGGGATG  CCAATGCATC   1140
CAACACTCCT  AACATGTGAG  AACAGTCTCT  GTCCTTATAG  CCAACCACAT  ATGGGATTTC   1200
TTGACAGGAA  CTTAAGAGAG  AATCACCAAA  TGACTTGTCC  TTATAAAGTC  ACTTCCTTCT   1260
ACCAACCAAC  TAAACCCTAT  GGTATGACGG  GTTTAATGGT  TCCTTGTCCG  GATTATAACG   1320
GGATGCAGCA  GCAGGTTCAG  AGCTTTCAAG  ACCAGTTTAA  TCATCCCAAC  GATCTCTACA   1380
GACCAAAAGC  TCCACAAAGA  GGCAACGATG  ACTTGGTTGA  GGATTTGAAT  CCTTCTCCTT   1440
CGACGCTGAA  TCAGAATCTT  GGTTTAGTCT  TACCTACTGA  CTTCAATGGA  GGTGAGGAAA   1500
CAGTAGGAAC  AGAGAACAAT  CTGCATAATC  AAGGGCAAGA  GTTGCCCACA  TCTTGGATTC   1560
AGTAAAGAAA  GCTTCAGAGT  TTTCTTTTA   TGTTTCTAG   TCTTTATAGC  TTTGTCTCTT   1620
GCTTATTCTC  TCATTAAACA  CAGTTTTTGA  TCTCTCCATT  TCATAGCCCA  TGTAGCAATG   1680
GAGAAGATTA  GGTTTCATAA  TAAGTTAATA  ACCAAATTCA  AA                      1722
```

( 2 ) INFORMATION FOR SEQ ID NO:10:

( i ) SEQUENCE CHARACTERISTICS:
    ( A ) LENGTH: 520 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Asp  Ser  Met  Asp  Met  Tyr  Asn  Asn  Asn  Ile  Gly  Met  Phe  Arg  Ser  Leu
 1              5                        10                       15

Val  Cys  Ser  Ser  Ala  Pro  Pro  Phe  Thr  Glu  Gly  His  Met  Cys  Ser  Asp
               20                        25                       30

Ser  His  Thr  Ala  Leu  Cys  Asp  Asp  Leu  Ser  Ser  Asp  Glu  Glu  Met  Glu
          35                        40                       45

Ile  Glu  Glu  Leu  Glu  Lys  Lys  Ile  Trp  Arg  Asp  Lys  Gln  Arg  Leu  Lys
     50                        55                       60

Arg  Leu  Lys  Glu  Met  Ala  Lys  Asn  Gly  Leu  Gly  Thr  Arg  Leu  Leu  Leu
65                       70                       75                       80
```

| | | | | | | | | | | | | | | |
|---|---|---|---|---|---|---|---|---|---|---|---|---|---|---|
| Lys | Gln | Gln | His | Asp 85 | Asp | Phe | Pro | Glu 90 | His | Ser | Ser | Lys | Arg 95 | Met |
| Tyr | Lys | Ala | Gln 100 | Asp | Gly | Ile | Leu | Lys 105 | Tyr | Met | Ser | Lys | Thr 110 | Met | Glu |
| Arg | Tyr | Lys | Ala 115 | Gln | Gly | Phe | Val | Tyr 120 | Gly | Ile | Val | Leu 125 | Glu | Asn | Gly |
| Lys | Thr 130 | Val | Ala | Gly | Ser | Ser 135 | Asp | Asn | Leu | Arg | Glu 140 | Trp | Trp | Lys | Asp |
| Lys 145 | Val | Arg | Phe | Asp | Arg 150 | Asn | Gly | Pro | Ala | Ala 155 | Ile | Ile | Lys | His | Gln 160 |
| Arg | Asp | Ile | Asn | Leu 165 | Ser | Asp | Gly | Ser | Asp 170 | Ser | Gly | Ser | Glu | Val 175 | Gly |
| Asp | Ser | Thr | Ala 180 | Gln | Lys | Leu | Leu | Glu 185 | Leu | Gln | Asp | Thr 190 | Thr | Leu | Gly |
| Ala | Leu | Leu 195 | Ser | Ala | Leu | Phe | Pro 200 | His | Cys | Asn | Pro | Pro 205 | Gln | Arg | Arg |
| Phe | Pro | Leu 210 | Glu | Lys | Gly | Val | Thr 215 | Pro | Pro | Trp | Trp | Pro 220 | Thr | Gly | Lys |
| Glu 225 | Asp | Trp | Trp | Asp | Gln 230 | Leu | Ser | Leu | Pro | Val 235 | Asp | Phe | Arg | Gly | Val 240 |
| Pro | Pro | Pro | Tyr | Lys 245 | Lys | Pro | His | Asp | Leu 250 | Lys | Lys | Leu | Trp | Lys 255 | Ile |
| Gly | Val | Leu | Ile 260 | Gly | Val | Ile | Arg | His 265 | Met | Ala | Ser | Asp | Ile 270 | Ser | Asn |
| Ile | Pro | Asn 275 | Leu | Val | Arg | Arg | Ser 280 | Arg | Ser | Leu | Gln | Glu 285 | Lys | Met | Thr |
| Ser | Arg 290 | Glu | Gly | Ala | Leu | Trp 295 | Leu | Ala | Ala | Leu | Tyr 300 | Arg | Glu | Lys | Ala |
| Ile 305 | Val | Asp | Gln | Ile | Ala 310 | Met | Ser | Arg | Glu | Asn 315 | Asn | Asn | Thr | Ser | Asn 320 |
| Phe | Leu | Val | Pro | Ala 325 | Thr | Gly | Gly | Asp | Pro 330 | Asp | Val | Leu | Phe | Pro 335 | Glu |
| Ser | Thr | Asp | Tyr 340 | Asp | Val | Glu | Leu | Ile 345 | Gly | Gly | Thr | His 350 | Arg | Thr | Asn |
| Gln | Gln | Tyr 355 | Pro | Glu | Phe | Glu | Asn 360 | Asn | Tyr | Asn | Cys | Val 365 | Tyr | Lys | Arg |
| Lys | Phe 370 | Glu | Glu | Asp | Phe | Gly 375 | Met | Pro | Met | His | Pro 380 | Thr | Leu | Leu | Thr |
| Cys 385 | Glu | Asn | Ser | Leu | Cys 390 | Pro | Tyr | Ser | Gln | Pro 395 | His | Met | Gly | Phe | Leu 400 |
| Asp | Arg | Asn | Leu | Arg 405 | Glu | Asn | His | Gln | Met 410 | Thr | Cys | Pro | Tyr | Lys 415 | Val |
| Thr | Ser | Phe | Tyr 420 | Gln | Pro | Thr | Lys | Pro 425 | Tyr | Gly | Met | Thr 430 | Gly | Leu | Met |
| Val | Pro | Cys 435 | Pro | Asp | Tyr | Asn | Gly 440 | Met | Gln | Gln | Val 445 | Gln | Ser | Phe |
| Gln | Asp | Gln | Phe | Asn 450 | His | Pro | Asn | Asp | Leu 455 | Tyr | Arg | Pro | Lys 460 | Ala | Pro |
| Gln 465 | Arg | Gly | Asn | Asp | Asp 470 | Leu | Val | Glu | Asp | Leu 475 | Asn | Pro | Ser | Pro | Ser 480 |
| Thr | Leu | Asn | Gln | Asn 485 | Leu | Gly | Leu | Val | Leu 490 | Pro | Thr | Asp | Phe | Asn 495 | Gly |
| Gly | Glu | Glu | Thr 500 | Val | Gly | Thr | Glu | Asn 505 | Asn | Leu | His | Asn | Gln 510 | Gly | Gln |

```
          Glu  Leu  Pro  Thr  Ser  Trp  Ile  Gln
                    515                      520
```

( 2 ) INFORMATION FOR SEQ ID NO:11:

( i ) SEQUENCE CHARACTERISTICS:
       ( A ) LENGTH: 2065 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

```
TTCCCCTGAG   AACGACAGGA   GAAAGAATAA   AAACCCTAAA   TTTCTTTAAT   TTCGGCGCTT      60

CAGATTATCG   TTGTTAAAGG   TTTTTGATTG   ATTTTGTTTA   AATGGGCGAT   CTTGCTATGT     120

CCGTAGCAGA   CATCAGGATG   GAGAATGAGC   CTGATGATTT   AGCTAGTGAT   AATGTTGCTG     180

AGATTGATGT   GAGTGATGAA   GAGATTGATG   CTGACGACCT   TGAGAGACGG   ATGTGGAAAG     240

ATCGTGTCAG   GCTTAAAAGA   ATCAAAGAGC   GACAAAAAGC   TGGCTCTCAA   GGAGCTCAAA     300

ACGAAGGGAG   ACACCTAAGA   AAATCTCTGA   TCAAGCTCAG   AGGAAGAAAA   TGTCTTAGAG     360

CTCAAGATGG   TATCCTTAAG   TACATTGTTG   AAGCTTATGG   AAGTCTGCAA   AGTTCGCGGG     420

TTTGTCTATG   GTATAATACC   GGAAAAGGGC   AAGCCTGTGA   GTTGGCTCCT   CTGACAATAT     480

AAGAGCTTGG   TGGAAAGAGA   AAGTGAAGTT   TGATAAGAAC   GGTCCTGCTG   CTATTGCTAA     540

ATACGAAGAG   GAGTGTTTAG   CGTTTGGGAA   ATCTGATGGG   AATAGGAATT   CACAGTTTGT     600

TCTCCAGGAT   TTGCAAGATG   CTACTTTAGG   GTCTTTGTTA   TCTTCTTTGA   TGCAACATTG     660

TGATCCTCCT   CAAAGGAAGT   ATCCGTTGGA   GAAAGGGACG   CCTCCGCCTT   GGTGGCCAAC     720

GGGGAATGAA   GAATGGTGGG   TGAAACTCGG   TCTGCCTAAA   AGCCAGAGTC   CTCCTTACCG     780

AAAACCTCAT   GATCTCAAGA   AGATGTGGAA   GGTTGGAGTT   TTAACGGCAG   TGATCAATCA     840

TATGTTACCT   GATATTGCAA   AGATTAAGAG   GCATGTTCGT   CAGTCGAAAT   GTTTACAGGA     900

CAAGATGACA   GCTAAAGAGA   GTGCGATTTG   GTTGGCGGTT   TTGAACCAAG   AGGAATCTTT     960

GATTCAGCAG   CCTAGCAGTG   ACAATGGAAA   CTCCAATGTG   ACTGAGACAC   ATCGTAGGGG    1020

TAATAACGCT   GACAGGAGGA   AACCTGTGGT   CAACAGTGAC   AGTGACTATG   ATGTTGATGG    1080

GACAGAGGAA   GCTTCAGGTT   CAGTTTCATC   TAAAGACAGT   AGAAGAAATC   AGATTCAAAA    1140

AGAACAACCA   ACAGCCATCT   CACATTCAGT   AAGAGATCAA   GATAAGCAG   AGAAACATCG     1200

CAGAAGGAAA   AGACCTCGAA   TTAGATCCGG   AACTGTCAAT   CGACAAGAGG   AAGAACAACC    1260

TGAAGCTCAA   CAAAGAAACA   TCTTACCTGA   TATGAATCAT   GTTGATGCCC   CTCTGCTAGA    1320

ATATAACATC   AACGGTACTC   ATCAAGAGGA   CGATGTTGTC   GACCCAAATA   TTGCCTTAGG    1380

ACCAGAGGAT   AATGGTCTGG   AACTAGTGGT   TCCTGAGTTC   AATAACCAAA   CATACTTATC    1440

TTCCACTTGT   TAATGAACAA   ACTATGATGC   CTGTAGACGA   AAGGCCAATG   CTTTATGGAC    1500

CCAAACCCTA   ACCAAGAGCT   TCAATTTGGG   TCAGGGTACA   ACTTCTACAA   TCCCTCTGCA    1560

GTGTTTGTAC   ATAACCAGGA   AGACGACATT   CTCCATACAC   AGATAGAAAT   GAATACACAA    1620

GCACCACCTC   ACAACAGTGG   GTTCGAGGAG   GCCCCAGGAG   GAGTACTTCA   ACCCCTTGGT    1680

TTACTCGGAA   ATGAAGACGG   TGTAACAGGG   AGTGAGTTGC   CTCAGTATCA   GAGTGGCATT    1740

CTGTCTCCAT   TGACTGACTT   GGACTTTGAC   TATGGTGGTT   TTGGTGATGA   TTTCTCATGG    1800
```

-continued

```
TTTGGAGCTT AGTGTCTTGC CATTTTTTT GGGAGATTAC ATAGTTCAAA AGGACATGGC      1860
AATAGTCTGG CTAGTACAGT TACTTCTCT TCTTCATTTC TTCTGATCTT ATATTCTTCC      1920
TCTTTTTTC TTATAATATT TTCTTAGATT TGTTAAGAGA AACAATTTC CTTTGAATA        1980
AGTTGCCAGA AGAACTGCTT TGCCCGTTGT AATGGTCTCT AGGGAAAGCA GTTAGCGTAT     2040
CATCATTTGT AAATTTACCT GTGAG                                           2065
```

( 2 ) INFORMATION FOR SEQ ID NO:12:

( i ) SEQUENCE CHARACTERISTICS:
        ( A ) LENGTH: 567 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Met Gly Asp Leu Ala Met Ser Val Ala Asp Ile Arg Met Glu Asn Glu
  1               5                  10                  15

Pro Asp Asp Leu Ala Ser Asp Asn Val Ala Glu Ile Asp Val Ser Asp
                 20                  25                  30

Glu Glu Ile Asp Ala Asp Asp Leu Glu Arg Arg Met Trp Lys Asp Arg
             35                  40                  45

Val Arg Leu Lys Arg Ile Lys Glu Arg Gln Lys Ala Gly Ser Gln Gly
 50                  55                  60

Ala Gln Thr Lys Glu Thr Pro Lys Lys Ile Ser Asp Gln Ala Gln Arg
 65                  70                  75                  80

Lys Lys Met Ser Arg Ala Gln Asp Gly Ile Leu Lys Tyr Met Leu Lys
                 85                  90                  95

Leu Met Glu Val Cys Lys Val Arg Gly Phe Val Tyr Gly Ile Ile Pro
                100                 105                 110

Glu Lys Gly Lys Pro Val Ser Gly Ser Ser Asp Asn Ile Arg Ala Trp
            115                 120                 125

Trp Lys Glu Lys Val Lys Phe Asp Lys Asn Gly Pro Ala Ala Ile Ala
130                 135                 140

Lys Tyr Glu Glu Glu Cys Leu Ala Phe Gly Lys Ser Asp Gly Asn Arg
145                 150                 155                 160

Asn Ser Gln Phe Val Leu Gln Asp Leu Gln Asp Ala Thr Leu Gly Ser
                165                 170                 175

Leu Leu Ser Ser Leu Met Gln His Cys Asp Pro Pro Gln Arg Lys Tyr
            180                 185                 190

Pro Leu Glu Lys Gly Thr Pro Pro Trp Trp Pro Thr Gly Asn Glu
            195                 200                 205

Glu Trp Trp Val Lys Leu Gly Leu Pro Lys Ser Gln Ser Pro Pro Tyr
210                 215                 220

Arg Lys Pro His Asp Leu Lys Lys Met Trp Lys Val Gly Val Leu Thr
225                 230                 235                 240

Ala Val Ile Asn His Met Leu Pro Asp Ile Ala Lys Ile Lys Arg His
                245                 250                 255

Val Arg Gln Ser Lys Cys Leu Gln Asp Lys Met Thr Ala Lys Glu Ser
            260                 265                 270

Ala Ile Trp Leu Ala Val Leu Asn Gln Glu Glu Ser Leu Ile Gln Gln
```

|   |   |   |   |   | 275 |   |   |   |   | 280 |   |   |   |   | 285 |   |   |
|---|---|---|---|---|---|---|---|---|---|---|---|---|---|---|---|---|---|
| Pro | Ser | Ser | Asp | Asn | Gly | Asn | Ser | Asn | Val | Thr | Glu | Thr | His | Arg | Arg |
|   | 290 |   |   |   | 295 |   |   |   |   | 300 |   |   |   |   |   |
| Gly | Asn | Asn | Ala | Asp | Arg | Arg | Lys | Pro | Val | Val | Asn | Ser | Asp | Ser | Asp |
| 305 |   |   |   | 310 |   |   |   |   |   | 315 |   |   |   |   | 320 |
| Tyr | Asp | Val | Asp | Gly | Thr | Glu | Glu | Ala | Ser | Gly | Ser | Val | Ser | Ser | Lys |
|   |   |   |   | 325 |   |   |   |   | 330 |   |   |   |   | 335 |   |
| Asp | Ser | Arg | Arg | Asn | Gln | Ile | Gln | Lys | Glu | Gln | Pro | Thr | Ala | Ile | Ser |
|   |   |   | 340 |   |   |   |   | 345 |   |   |   |   | 350 |   |   |
| His | Ser | Val | Arg | Asp | Gln | Asp | Lys | Ala | Glu | Lys | His | Arg | Arg | Arg | Lys |
|   |   |   | 355 |   |   |   |   | 360 |   |   |   |   | 365 |   |   |
| Arg | Pro | Arg | Ile | Arg | Ser | Gly | Thr | Val | Asn | Arg | Gln | Glu | Glu | Glu | Gln |
|   | 370 |   |   |   |   | 375 |   |   |   |   | 380 |   |   |   |   |
| Pro | Glu | Ala | Gln | Gln | Arg | Asn | Ile | Leu | Pro | Asp | Met | Asn | His | Val | Asp |
| 385 |   |   |   |   | 390 |   |   |   |   | 395 |   |   |   |   | 400 |
| Ala | Pro | Leu | Leu | Glu | Tyr | Asn | Ile | Asn | Gly | Thr | His | Gln | Glu | Asp | Asp |
|   |   |   |   | 405 |   |   |   |   | 410 |   |   |   |   | 415 |   |
| Val | Val | Asp | Pro | Asn | Ile | Ala | Leu | Gly | Pro | Glu | Asp | Asn | Gly | Leu | Glu |
|   |   |   | 420 |   |   |   |   | 425 |   |   |   |   | 430 |   |   |
| Leu | Val | Val | Pro | Glu | Phe | Asn | Asn | Asn | Tyr | Thr | Tyr | Leu | Pro | Leu | Val |
|   |   | 435 |   |   |   |   | 440 |   |   |   |   | 445 |   |   |   |
| Asn | Glu | Gln | Thr | Met | Met | Pro | Val | Asp | Glu | Arg | Pro | Met | Leu | Tyr | Gly |
|   | 450 |   |   |   |   | 455 |   |   |   |   | 460 |   |   |   |   |
| Pro | Asn | Pro | Asn | Gln | Glu | Leu | Gln | Phe | Gly | Ser | Gly | Tyr | Asn | Phe | Tyr |
| 465 |   |   |   |   | 470 |   |   |   |   | 475 |   |   |   |   | 480 |
| Asn | Pro | Ser | Ala | Val | Phe | Val | His | Asn | Gln | Glu | Asp | Asp | Ile | Leu | His |
|   |   |   |   | 485 |   |   |   |   | 490 |   |   |   |   | 495 |   |
| Thr | Gln | Ile | Glu | Met | Asn | Thr | Gln | Ala | Pro | Pro | His | Asn | Ser | Gly | Phe |
|   |   |   | 500 |   |   |   |   | 505 |   |   |   |   | 510 |   |   |
| Glu | Glu | Ala | Pro | Gly | Gly | Val | Leu | Gln | Pro | Leu | Gly | Leu | Leu | Gly | Asn |
|   |   |   | 515 |   |   |   |   | 520 |   |   |   |   | 525 |   |   |
| Glu | Asp | Gly | Val | Thr | Gly | Ser | Glu | Leu | Pro | Gln | Tyr | Gln | Ser | Gly | Ile |
|   | 530 |   |   |   |   | 535 |   |   |   |   | 540 |   |   |   |   |
| Leu | Ser | Pro | Leu | Thr | Asp | Leu | Asp | Phe | Asp | Tyr | Gly | Gly | Phe | Gly | Asp |
| 545 |   |   |   |   | 550 |   |   |   |   | 555 |   |   |   |   | 560 |
| Asp | Phe | Ser | Trp | Phe | Gly | Ala |   |   |   |   |   |   |   |   |   |
|   |   |   |   | 565 |   |   |   |   |   |   |   |   |   |   |   |

( 2 ) INFORMATION FOR SEQ ID NO:13:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

| Met | Thr | Val | Val | Arg | Glu | Tyr | Asp | Pro | Thr | Arg | Asp | Leu | Val | Gly | Val |
|---|---|---|---|---|---|---|---|---|---|---|---|---|---|---|---|
| 1 |   |   |   | 5 |   |   |   |   | 10 |   |   |   |   | 15 |   |
| Glu | Asp | Val | Glu | Arg | Arg | Cys | Glu | Val | Gly | Pro | Ser | Gly | Lys | Leu | Ser |
|   |   |   | 20 |   |   |   |   | 25 |   |   |   |   | 30 |   |   |
| Leu | Phe | Thr | Asp | Leu | Leu | Gly | Asp | Pro | Ile | Cys | Arg | Ile | Arg | His | Ser |

|     |     |     |     | 35  |     |     |     |     | 40  |     |     |     |     | 45  |
| --- | --- | --- | --- | --- | --- | --- | --- | --- | --- | --- | --- | --- | --- | --- |
| Pro | Ser | Tyr | Leu | Met | Leu | Val | Ala | Glu | Met | Gly | Thr | Glu | Xaa | Xaa | Xaa |
|     | 50  |     |     |     | 55  |     |     |     |     | 60  |     |     |     |     |
| Lys | Lys | Glu | Ile | Val | Gly | Met | Ile | Arg | Gly | Cys | Ile | Lys | Thr | Val | Thr |
| 65  |     |     |     |     | 70  |     |     |     |     | 75  |     |     |     |     | 80  |
| Cys | Gly | Gln | Lys | Leu | Asp | Leu | Asn | His | Lys | Xaa | Xaa | Xaa | Ser | Gln | Asn |
|     |     |     |     | 85  |     |     |     |     | 90  |     |     |     |     | 95  |     |
| Asp | Val | Val | Xaa | Xaa | Lys | Pro | Leu | Tyr | Thr | Lys | Leu | Xaa | Xaa | Xaa | Xaa |
|     |     |     | 100 |     |     |     |     | 105 |     |     |     |     | 110 |     |     |
| Xaa | Xaa | Xaa | Xaa | Xaa | Xaa | Xaa | Xaa | Ala | Tyr | Val | Leu | Gly | Leu | Arg | Val |
|     |     |     | 115 |     |     |     |     | 120 |     |     |     |     | 125 |     |     |
| Ser | Pro | Phe | His | Arg | Arg | Gln | Gly | Ile | Gly | Phe | Lys | Leu | Val | Lys | Met |
|     | 130 |     |     |     |     | 135 |     |     |     |     | 140 |     |     |     |     |
| Met | Glu | Glu | Trp | Phe | Arg | Gln | Xaa | Asn | Gly | Ala | Glu | Tyr | Ser | Tyr | Ile |
| 145 |     |     |     |     | 150 |     |     |     |     | 155 |     |     |     |     | 160 |
| Ala | Thr | Glu | Asn | Asp | Xaa | Xaa | Xaa | Xaa | Asn | Gln | Ala | Ser | Val | Asn | Leu |
|     |     |     |     | 165 |     |     |     |     | 170 |     |     |     |     | 175 |     |
| Phe | Thr | Gly | Lys | Cys | Gly | Tyr | Ser | Glu | Phe | Arg | Thr | Pro | Ser | Ile | Leu |
|     |     |     | 180 |     |     |     |     | 185 |     |     |     |     | 190 |     |     |
| Val | Asn | Pro | Val | Tyr | Ala | His | Arg | Val | Asn | Val | Ser | Arg | Arg | Val | Thr |
|     |     | 195 |     |     |     |     | 200 |     |     |     |     | 205 |     |     |     |
| Val | Ile | Lys | Leu | Glu | Pro | Val | Asp | Ala | Glu | Thr | Xaa | Xaa | Xaa | Leu | Tyr |
|     | 210 |     |     |     |     | 215 |     |     |     |     | 220 |     |     |     |     |
| Arg | Ile | Arg | Phe | Ser | Thr | Thr | Glu | Phe | Phe | Xaa | Xaa | Xaa | Xaa | Xaa | Xaa |
| 225 |     |     |     |     | 230 |     |     |     |     | 235 |     |     |     |     | 240 |

( 2 ) INFORMATION FOR SEQ ID NO:14:

( i ) SEQUENCE CHARACTERISTICS:
        ( A ) LENGTH: 1702 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

| | | | | | |
|---|---|---|---|---|---|
| CTCCAACTTT | TAAAACTCAT | CATAAATAGT | AAAAAGTAG | CCGGAAAAAT | AAAATAAAAA | 60 |
| GTCTATTTCT | CTTTCCTTTA | AAATCCAAAT | CCTATAAACT | CATAGCTTTC | TCTGTTCTTT | 120 |
| ACTTATACCT | CACGTTATAC | ATATATATAG | AGTTTCTATA | AATGCTTCTC | TTTCCTCTCG | 180 |
| AACAAATCTT | CCTCACTTCT | CTCATTTCCA | CACTCACCTT | CCTCTCTATA | TATTAAACCC | 240 |
| TATCTACTTA | ACTCTTCTTC | TAACTCTAAT | CTCTCTCTCT | ATTTACTCTG | CTTCTGTTCT | 300 |
| CACTCTGAAA | GAACCAAAAC | ATGACGGTGG | TTAGAGAGTA | CGACCCGACC | CGAGACTTAG | 360 |
| TCGGCGTGGA | GGACGTGGAA | CGACGGTGTG | AAGTCGGACC | AAGCGGCAAG | CTTTCTCTTT | 420 |
| TCACCGACCT | TTTGGGTGAC | CCGATTTGTA | GAATCCGACA | TTCACCTTCC | TATCTCATGC | 480 |
| TGGTGGCTGA | GATGGGTACG | GAGAAGAAGG | AGATAGTGGG | CATGATTAGA | GGATGTATCA | 540 |
| AAACCGTTAC | ATGTGGCCAA | AAACTCGATT | TAAATCACAA | ATCTCAAAAC | GATGTCGTTA | 600 |
| AGCCTCTTTA | CACTAAACTC | GCTTACGTCT | TGGGCCTTCG | CGTCTCTCCT | TTTCACAGGA | 660 |
| GACAAGGGAT | TGGGTTTAAG | CTCGTGAAGA | TGATGGAGGA | ATGGTTTAGA | CAAAACGGAG | 720 |
| CTGAGTATTC | GTATATTGCA | ACTGAGAACG | ATAATCAAGC | TTCTGTGAAT | TTGTTCACCG | 780 |

| GGAAATGTGG | TTATTCGGAG | TTTCGTACAC | CGTCGATTTT | GGTTAACCCG | GTTTACGCTC | 840 |
| ATCGAGTTAA | TGTTTCGCGG | CGAGTCACGG | TTATCAAGTT | AGAGCCGGTT | GATGCTGAGA | 900 |
| CGTTGTACCG | AATCCGGTTT | AGCACAACAG | AGTTTTTCCC | GCGGGATATT | GATTCGGTAC | 960 |
| TTAATAACAA | ACTCTCGCTT | GGGACTTTCG | TCGCGGTGCC | ACGTGGAAGC | TGTTATGGAT | 1020 |
| CCGGGTCTGG | ATCATGGCCC | GGTTCGGCTA | AATTCCTCGA | ATATCCACCC | GAGTCATGGG | 1080 |
| CCGTATTAAG | CGTGTGGAAT | TGTAAAGACT | CGTTCTGTT | AGAAGTACGT | GGAGCGTCGA | 1140 |
| GATTGAGACG | TGTGGTGGCT | AAAACGACGC | GAGTAGTTGA | TAAAACGTTG | CCGTTTCTGA | 1200 |
| AACTACCTTC | GATACCGTCC | GTTTCGAAC | CTTTGGACT | TCATTTATG | TATGGAATCG | 1260 |
| GAGGAGAAGG | TCCACGCGCG | GTGAAGATGG | TGAAATCCTT | GTGTGCTCAC | GCGCATAACT | 1320 |
| TGGCTAAGGC | AGGTGGTTGT | GGTGTCGTGG | CGGCGGAAGT | TGCCGGAGAA | GACCCGTTGC | 1380 |
| GGCGAGGAAT | ACCACATTGG | AAAGTGCTAT | CGTGTGACGA | GGATCTTTGG | TGTATAAAGC | 1440 |
| GGCTTGGAGA | TGACTATAGT | GATGGTGTTG | TTGGTGATTG | GACTAAATCG | CCACCTGGCG | 1500 |
| TTTCCATTTT | TGTAGACCCT | AGAGAATTTT | AAAACTTTTT | TTTAACTCT | ATAATATATA | 1560 |
| TTCTCTATTA | ACCACTTGAT | GTTAAATTAG | GGGTTTTCTT | CTAAGTTTAT | AGATTTCTT | 1620 |
| GTTTTAGAAT | TAATCTTTTT | TTTAGGTAAC | TTTTTTGCT | TTTTGTTTTG | TTTTGTTTTG | 1680 |
| TTTTTGTGGG | TGTTATAAAT | TA | | | | 1702 |

( 2 ) INFORMATION FOR SEQ ID NO:15:

( i ) SEQUENCE CHARACTERISTICS:
        ( A ) LENGTH: 4146 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

| TGTCATAATC | AGTACAAAAT | AAATCACCTA | CCAACCTGAA | CTATATGTTA | TATATTTTGA | 60 |
| GGGGCCACGT | CAAGTGTGCC | GTTTATTTTT | GTGTTTATGA | TTGTTAATA | TTTGTGCGTG | 120 |
| TGATGGTGTT | TCTTGCTTAG | TTTCCACTTA | ATACACAATC | AAATATCAAG | TGGAACTATT | 180 |
| TATGAAAATT | GTTCTTCGAG | AAGAATTCTG | ACCCTAAAAG | GTCATTTGAG | GGCTTGAGGC | 240 |
| TTATTGTTTC | CAAATTACAC | CAGTAAACAA | GGGTTTTTT | TTGTCAACAA | AGATTATTGT | 300 |
| AATTCGAATT | TCGTCTACAA | TAAAACAATT | TTCTTACTAA | AACAAAACAA | TTAGCTGACG | 360 |
| GTTGATATTT | CGGCTTTTGA | GTTTAATTAA | CTAATTGGTG | ATTATGTTGA | TGATCTTTCA | 420 |
| CACCTAATGA | AGTGTCATGT | ATATGTATAT | ATGTATATAC | TTATGTATAT | ATAAAACGTA | 480 |
| CATATAATCA | TTTGTCATAT | ATATCATCAT | GTATTGCATG | ACTAAACTAC | CCTTAAAAGA | 540 |
| GGAATACGAT | AGACATGACC | TTTAGGAATT | TGTTTTTTC | TTCTAAATGG | ATTCCTTCGC | 600 |
| TTCTTTTTAG | CCTCGTAGTG | AATTTGAACA | TTGCAGTTAT | TTCTAGTAAG | ATATTTTTC | 660 |
| TGTATTTTTC | GGAAAATGTT | AAAAACTAAT | TATACACAAT | TTACTTTCTC | TCTCAACTCT | 720 |
| TATTTTACGT | TACTGTTTTT | TTTTCCTCT | TGCAAAATTA | GAGCTGATGT | ATTTACATTT | 780 |
| ACTAGTAATT | TGGTAGATAG | ACAGTTAATG | TAGTATATAG | ATGGGGTTGA | GGGCAAATGA | 840 |
| TTACTTGGGA | GATGGTGCAA | TGCATCAGAG | TGATGATGTG | GAATTTAATA | AGTGTGAATT | 900 |

-continued

| | | | | | | |
|---|---|---|---|---|---|---|
| TATGGGCAAA | GGAAGGGAAC | TAGTAGTAGA | AAGGGAAATA | AATACAGTAC | AAGTAAGAGG | 960 |
| AAAACGAAAA | GAGAGATAGA | AACCATAATA | ATGAGTTAAC | GCAGACATAG | CCGCCATTTT | 1020 |
| CAACTTCTCA | CTCCCACTTA | CAACTTCTCC | TTCTGGGCAA | GTTTTCCACA | TCAATGCTCG | 1080 |
| TCTTAATCAC | CATTAATCTC | TACTCATCAT | TAATACGTTG | AAGCCCACTA | TTTCAAAATT | 1140 |
| TACTAGGAGT | ATTTATTCGT | GAAAAACATT | TAAATGTCCC | TAATTATAAG | AGATTTAATT | 1200 |
| TCATATTTAT | TGTATTAAAG | AGAATTTACA | TTAGCTGTCA | AAAAAAAAAA | AAAAAGAGAA | 1260 |
| TTAACATTAT | TTTACAGAAC | ATAAAATTTT | GAAAATAGAT | AGCGCCACTG | CATGTAAGAA | 1320 |
| CATACAAATT | TCTTTTTTC | AACAAATCT | ATTTATATTT | CTTCTTTTTT | TGAACATTAT | 1380 |
| GTGTAGTTTG | TAGTAAACTA | AAAGTGTGG | ACCAACACAA | TTTAAATCAT | TCGATTTTGT | 1440 |
| AGCAAAAACA | TTTTTGTTCC | AATTCCAAG | CAGCAAATAT | GGAAGGAATA | TAAATTCTTT | 1500 |
| ACTATTTTTC | CTCTTAACAC | ATAAAAGTAA | AAAAAGCATT | CAATGATCAG | TTAAAATCTG | 1560 |
| GTTAGAATTC | TACCTTATCA | TTTAGAACTA | GCTAATATTT | AAATTCATAT | ATACAAAAAA | 1620 |
| TAAAATGGGA | ACTGTAGAGA | CTAGAGACTA | TAAATAGAGG | ATTGAGAAGA | AGAACTTTTA | 1680 |
| AAGCTCTATC | AATCATGAAC | TACTCGCCTT | CTCCAACTTT | TAAAACTCAT | CATAAATAGT | 1740 |
| AAAAAAGTAG | CCGGAAAAAT | AAAATAAAAA | GTCTATTTCT | CTTTCCTTTA | AAATCCAAAT | 1800 |
| CCTATAAACT | CATAGCTTTC | TCTGTTCTTT | ACTTATACCT | CACGTTATAC | ATATATATAG | 1860 |
| AGTTCTATA | AATGCTTCTC | TTTCCTCTCG | AACAAATCTT | CCTCACTTCT | CTCATTTCCA | 1920 |
| CACTCACCTT | CCTCTCTATA | TATTAAACCC | TATCTACTTA | ACTCTTCTTC | TAACTCTAAT | 1980 |
| CTCTCTCTCT | ATTTACTCTG | CTTCTGTTCT | CACTCTGAAA | GAACCAAAAC | ATGACGGTGG | 2040 |
| TTAGAGAGTA | CGACCCGACC | CGAGACTTAG | TCGGCGTGGA | GGACGTGGAA | CGACGGTGTG | 2100 |
| AAGTCGGACC | AAGCGGCAAG | CTTTCTCTTT | TCACCGACCT | TTTGGGTGAC | CCGATTGTA | 2160 |
| GAATCCGACA | TTCACCTTCC | TATCTCATGC | TGGTAATAAC | ATGTTTCACA | ATCTTTATC | 2220 |
| TTCTTTTACT | TGTATGTCTC | TTCAAAAACT | CTGTTTGTTT | TTTGAACCTA | GAAGTAGAAA | 2280 |
| ACATAGAACA | CCAACTTCTC | AACCTTTGGT | TAATCCAAAA | AACCCATTTT | CCATAAACAA | 2340 |
| TTAAAGTTCG | GTTCTTTTTT | TGGTATCATT | TCTATTTTTT | TCCGATTCTT | GATAAGATCA | 2400 |
| AAAGACTCAT | CATTTATATT | ATTTTTTGCA | ACCAAATGAT | ACCCGAGTAA | CTATAACTAA | 2460 |
| TAAAGTTTCC | TCTTTATTAT | AAAAGGTTAA | AAACATATAA | TAACGGAAAA | TTTAAATTAT | 2520 |
| GGGACTGTAA | CAGGTGGCTG | AGATGGGTAC | GGAGAAGAAG | GAGATAGTGG | GCATGATTAG | 2580 |
| AGGATGTATC | AAAACCGTTA | CATGTGGCCA | AAAACTCGAT | TTAAATCACA | AATCTCAAAA | 2640 |
| CGATGTCGTT | AAGCCTCTTT | ACACTAAACT | CGCTTACGTC | TTGGGCCTTC | GCGTCTCTCC | 2700 |
| TTTTCACAGG | TACCCTTCCG | TTTTCCTCCC | ACTCATAATC | ACACGCTATT | ATAGATTTTG | 2760 |
| GTTATCTAAA | CTAGTTTTGG | TTTTTGCAGG | AGACAAGGGA | TTGGGTTTAA | GCTCGTGAAG | 2820 |
| ATGATGGAGG | AATGGTTTAG | ACAAAACGGA | GCTGAGTATT | CGTATATTGC | AACTGAGAAC | 2880 |
| GATAATCAAG | CTTCTGTGAA | TTTGTTCACC | GGGAAATGTG | GTTATTCGGA | GTTTCGTACA | 2940 |
| CCGTCGATTT | TGGTTAACCC | GGTTTACGCT | CATCGAGTTA | ATGTTTCGCG | GCGAGTCACG | 3000 |
| GTTATCAAGT | TAGAGCCGGT | TGATGCTGAG | ACGTTGTACC | GAATCCGGTT | TAGCACAACA | 3060 |
| GAGTTTTTCC | CGCGGGATAT | TGATTCGGTA | CTTAATAACA | AACTCTCGCT | TGGGACTTTC | 3120 |
| GTCGCGGTGC | CACGTGGAAG | CTGTTATGGA | TCCGGGTCTG | GATCATGGCC | CGGTTCGGCT | 3180 |
| AAATTCCTCG | AATATCCACC | CGAGTCATGG | GCCGTATTAA | GCGTGTGGAA | TTGTAAAGAC | 3240 |
| TCGTTTCTGT | TAGAAGTACG | TGGAGCGTCG | AGATTGAGAC | GTGTGGTGGC | TAAAACGACG | 3300 |

| | | | | | |
|---|---|---|---|---|---|
| CGAGTAGTTG | ATAAAACGTT | GCCGTTTCTG | AAACTACCTT | CGATACCGTC | CGTTTTCGAA | 3360
| CCTTTTGGAC | TTCATTTTAT | GTATGGAATC | GGAGGAGAAG | GTCCACGCGC | GGTGAAGATG | 3420
| GTGAAATCCT | TGTGTGCTCA | CGCGCATAAC | TTGGCTAAGG | CAGGTGGTTG | TGGTGTCGTG | 3480
| GCGGCGGAAG | TTGCCGGAGA | AGACCCGTTG | CGGCGAGGAA | TACCACATTG | GAAAGTGCTA | 3540
| TCGTGTGACG | AGGATCTTTG | GTGTATAAAG | CGGCTTGGAG | ATGACTATAG | TGATGGTGTT | 3600
| GTTGGTGATT | GGACTAAATC | GCCACCTGGC | GTTTCCATTT | TTGTAGACCC | TAGAGAATTT | 3660
| TAAAACTTTT | TTTTAACTC | TATAATATAT | ATTCTCTATT | AACCACTTGA | TGTTAAATTA | 3720
| GGGGTTTTCT | TCTAAGTTTA | TAGATTTTCT | TGTTTAGAA | TTAATCTTTT | TTTAGGTAA | 3780
| CTTTTTTTGC | TTTTTGTTTT | GTTTTGTTTT | GTTTTGTGG | GTGTTATAAA | TTAGTGGTAA | 3840
| GAGGTAATAT | CTCCTACTTT | TGGGTTTGTG | TCTTCTTGTC | TTGTAAATGG | ATCTAGCTTT | 3900
| TTAAGATACT | TTTTCTTTGT | GGCCAAACCA | AAACGCCGAC | CTGATTATTA | TTTCCAAGTA | 3960
| GATAAAATTT | CATGAACGCA | CTGATACGTA | TAATGATGCA | ATTTGTGTTA | AGACGATACT | 4020
| TTGGAGATAA | AATTACAATA | TGACAATGAT | AGAAAATGTT | ACCAATAACG | ATTAGCATTA | 4080
| TCGTGTGTGC | CATCAAGTAT | AACTAAGAGA | AAGACGCACA | TTTCTTTAA | GAGTAAATAA | 4140
| AATATT | | | | | | 4146

( 2 ) INFORMATION FOR SEQ ID NO:16:

( i ) SEQUENCE CHARACTERISTICS:
        ( A ) LENGTH: 398 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

```
Met  Thr  Val  Val  Arg  Glu  Tyr  Asp  Pro  Thr  Arg  Asp  Leu  Val  Gly  Val
 1              5                        10                       15

Glu  Asp  Val  Glu  Arg  Arg  Cys  Glu  Val  Gly  Pro  Ser  Gly  Lys  Leu  Ser
                20                       25                       30

Leu  Phe  Thr  Asp  Leu  Leu  Gly  Asp  Pro  Ile  Cys  Arg  Ile  Arg  His  Ser
               35                        40                       45

Pro  Ser  Tyr  Leu  Met  Leu  Val  Ala  Glu  Met  Gly  Thr  Glu  Lys  Lys  Glu
          50                        55                       60

Ile  Val  Gly  Met  Ile  Arg  Gly  Cys  Ile  Lys  Thr  Val  Thr  Cys  Gly  Gln
 65                       70                        75                       80

Lys  Leu  Asp  Leu  Asn  His  Lys  Ser  Gln  Asn  Asp  Val  Val  Lys  Pro  Leu
                    85                       90                        95

Tyr  Thr  Lys  Leu  Ala  Tyr  Val  Leu  Gly  Leu  Arg  Val  Ser  Pro  Phe  His
               100                       105                      110

Arg  Arg  Gln  Gly  Ile  Gly  Phe  Lys  Leu  Val  Lys  Met  Met  Glu  Glu  Trp
              115                       120                      125

Phe  Arg  Gln  Asn  Gly  Ala  Glu  Tyr  Ser  Tyr  Ile  Ala  Thr  Glu  Asn  Asp
          130                       135                      140

Asn  Gln  Ala  Ser  Val  Asn  Leu  Phe  Thr  Gly  Lys  Cys  Gly  Tyr  Ser  Glu
145                       150                      155                      160

Phe  Arg  Thr  Pro  Ser  Ile  Leu  Val  Asn  Pro  Val  Tyr  Ala  His  Arg  Val
                    165                       170                      175
```

-continued

```
Asn  Val  Ser  Arg  Arg  Val  Thr  Val  Ile  Lys  Leu  Glu  Pro  Val  Asp  Ala
              180                      185                      190
Glu  Thr  Leu  Tyr  Arg  Ile  Arg  Phe  Ser  Thr  Thr  Glu  Phe  Phe  Pro  Arg
         195                      200                      205
Asp  Ile  Asp  Ser  Val  Leu  Asn  Asn  Lys  Leu  Ser  Leu  Gly  Thr  Phe  Val
    210                      215                      220
Ala  Val  Pro  Arg  Gly  Ser  Cys  Tyr  Gly  Ser  Gly  Ser  Gly  Ser  Trp  Pro
225                      230                      235                      240
Gly  Ser  Ala  Lys  Phe  Leu  Glu  Tyr  Pro  Pro  Glu  Ser  Trp  Ala  Val  Leu
              245                      250                           255
Ser  Val  Trp  Asn  Cys  Lys  Asp  Ser  Phe  Leu  Leu  Glu  Val  Arg  Gly  Ala
              260                      265                      270
Ser  Arg  Leu  Arg  Arg  Val  Val  Ala  Lys  Thr  Arg  Arg  Val  Val  Asp  Lys
         275                      280                      285
Thr  Leu  Pro  Phe  Leu  Lys  Leu  Pro  Ser  Ile  Pro  Ser  Val  Phe  Glu  Pro
    290                      295                      300
Phe  Gly  Leu  His  Phe  Met  Tyr  Gly  Ile  Gly  Gly  Glu  Gly  Pro  Arg  Ala
305                           310                      315                 320
Val  Lys  Met  Val  Lys  Ser  Leu  Cys  Ala  His  Ala  His  Asn  Leu  Ala  Lys
              325                      330                      335
Ala  Gly  Gly  Cys  Gly  Val  Val  Ala  Ala  Glu  Val  Ala  Gly  Glu  Asp  Pro
              340                      345                      350
Leu  Arg  Arg  Gly  Ile  Pro  His  Trp  Lys  Val  Leu  Ser  Cys  Asp  Glu  Asp
         355                      360                      365
Leu  Trp  Cys  Ile  Lys  Arg  Leu  Gly  Asp  Asp  Tyr  Ser  Asp  Gly  Val  Val
    370                      375                      380
Gly  Asp  Trp  Thr  Lys  Cys  His  Leu  Ala  Phe  Pro  Phe  Leu  Glx
385                      390                      395
```

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:17:

GAGTTGCGCA TG                                                        12

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:18:

```
Gly  Val  Ala  His
1
```

( 2 ) INFORMATION FOR SEQ ID NO:19:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:19:

TGCTACAATC AGAATTCTTG CAGT        24

( 2 ) INFORMATION FOR SEQ ID NO:20:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:20:

Ala  Thr  Ile  Arg  Ile  Leu  Ala  Val
    1                   5

( 2 ) INFORMATION FOR SEQ ID NO:21:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:21:

GGATCCTCTA GTCAAATTAC CGC        23

( 2 ) INFORMATION FOR SEQ ID NO:22:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

AGATCTGGTA TATTCCGTCT GCAC        24

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:23:

CCGGATTCGG TTTGTAGC                                                                 18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

GACGTGCATG TTCTTGGG                                                                 18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:25:

GAAAGCCACA TCACCTGC                                                                 18

( 2 ) INFORMATION FOR SEQ ID NO:26:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:26:

GGGGTGGAGT TATCCAC                                                                  17

( 2 ) INFORMATION FOR SEQ ID NO:27:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:27:

GACACCGGGA AGTATCG 17

(2) INFORMATION FOR SEQ ID NO:28:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:28:

CTGCTTTCAT AGAAGAGGC 19

(2) INFORMATION FOR SEQ ID NO:29:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:29:

GTCAGAACAA ACCTGCTCC 19

(2) INFORMATION FOR SEQ ID NO:30:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:30:

CACCCAGGTC TTGGTGG 17

(2) INFORMATION FOR SEQ ID NO:31:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA ( i i i ) HYPOTHETICAL: NO ( i v ) ANTI-SENSE: YES ( x i ) SEQUENCE DESCRIPTION: SEQ ID NO:31:

GGCCGCCATG GATGCG  16

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:32:

TCTCAATCAA GAGGAGGC  18

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:33:

CTTGAAGGAT CCGAGTGG  18

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:34:

CAGGTTGGCG AGTTCCTCG  19

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:35:

CTTGCTGTTA TTCTCCATGC 20

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:36:

CCCTGGACCA GCTCCTGG 18

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:37:

TGGCGCAAGC ATCGTCCC 18

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:38:

AAATGTTCAG GAATCTCTCG 20

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:39:

CTGGCTGGCA GCCACGCC 18

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:40:

GCGTTCTCAA AGCTGCGG                                          18

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:41:

ACTGATGGGT CTTCTGGG                                        18

( 2 ) INFORMATION FOR SEQ ID NO:42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:42:

GGATCAGGAT GGACCCGG                                        18

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:43:

TGGTTGCTGA AGCCAGGG                                        18

( 2 ) INFORMATION FOR SEQ ID NO:44:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:44:

TCCATTCATA GAGAGTGGG 19

( 2 ) INFORMATION FOR SEQ ID NO:45:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:45:

ATGCCCAAGA ACATGCACG 19

( 2 ) INFORMATION FOR SEQ ID NO:46:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:46:

CAACTGATCC TTTACCCTGC 20

( 2 ) INFORMATION FOR SEQ ID NO:47:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:47:

GTTGTTAGGT CAACTTGCG 19

( 2 ) INFORMATION FOR SEQ ID NO:48:

( i ) SEQUENCE CHARACTERISTICS:
      ( A ) LENGTH: 19 base pairs
      ( B ) TYPE: nucleic acid
      ( C ) STRANDEDNESS: single

```
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:48:
```

CTCTGTTAGG GCTTCCTCC                                                                      19

( 2 ) INFORMATION FOR SEQ ID NO:49:

```
        ( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:49:
```

GAATCAGATT TCGCGAGG                                                                       18

( 2 ) INFORMATION FOR SEQ ID NO:50:

```
        ( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:50:
```

GTCCAAATGG AGGAAGCC                                                                       18

( 2 ) INFORMATION FOR SEQ ID NO:51:

```
        ( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:51:
```

CCACGACTGT ACAATTGACC TTG                                                                 23

( 2 ) INFORMATION FOR SEQ ID NO:52:

```
        ( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA
```

( i i i ) HYPOTHETICAL: NO ( i v ) ANTI-SENSE: YES ( x i ) SEQUENCE DESCRIPTION: SEQ ID NO:52:

CATGATCGCA AGTTGACC					18

( 2 ) INFORMATION FOR SEQ ID NO:53:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:53:

AGAAAACTCT TATCAAGCTA CG					22

( 2 ) INFORMATION FOR SEQ ID NO:54:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:54:

AAGCTTATGG GTGCTCGTGC					20

( 2 ) INFORMATION FOR SEQ ID NO:55:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:55:

GGAAAGAGAG AAAGACTCAG					20

( 2 ) INFORMATION FOR SEQ ID NO:56:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:56:

GCCACCAAGT CATACCCG 18

( 2 ) INFORMATION FOR SEQ ID NO:57:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:57:

CCTTCTATAT TTGGTTCC 18

( 2 ) INFORMATION FOR SEQ ID NO:58:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:58:

CCATTCTCCG GAATAATCC 19

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:59:

CACGGAGCAG GATAAGGGTA 20

( 2 ) INFORMATION FOR SEQ ID NO:60:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:60:

CGGATTGGAT TGTGTGTGC 19

( 2 ) INFORMATION FOR SEQ ID NO:61:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:61:

CGCCACTGCA TGTAAGAAC         19

( 2 ) INFORMATION FOR SEQ ID NO:62:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:62:

TCCACACGCT TAATACGGC         19

( 2 ) INFORMATION FOR SEQ ID NO:63:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:63:

GGTACGGAGA AGAAGGAG         18

( 2 ) INFORMATION FOR SEQ ID NO:64:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:64:

CGCGGGATAT TGATTCGGT         19

( 2 ) INFORMATION FOR SEQ ID NO:65:

( i ) SEQUENCE CHARACTERISTICS:

( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:65:

GTGTTGAACA CGCCCACAA                                                                                     19

( 2 ) INFORMATION FOR SEQ ID NO:66:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:66:

ACGACACCAC AACCACCT                                                                                      18

( 2 ) INFORMATION FOR SEQ ID NO:67:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:67:

GACAAGAAGA CACAAACC                                                                                      18

( 2 ) INFORMATION FOR SEQ ID NO:68:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:68:

GAATCGGAGG AGAAGGTC                                                                                      18

( 2 ) INFORMATION FOR SEQ ID NO:69:

( i ) SEQUENCE CHARACTERISTICS:
            ( A ) LENGTH: 240 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:69:

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 1 | | | | 5 | | | | | 10 | | | | | 15 |
| Xaa | Met | Phe | Gly | Tyr | Arg | Ser | Asn | Val | Pro | Lys | Val | Arg | Leu | Thr | Thr |
| | | | 20 | | | | | 25 | | | | | 30 | | |
| Asp | Arg | Leu | Val | Val | Arg | Leu | Val | His | Asp | Arg | Asp | Ala | Trp | Arg | Leu |
| | | 35 | | | | | 40 | | | | | 45 | | | |
| Ala | Asp | Tyr | Tyr | Ala | Glu | Asn | Arg | His | Phe | Leu | Lys | Pro | Trp | Glu | Pro |
| | 50 | | | | | 55 | | | | | 60 | | | | |
| Val | Arg | Asp | Glu | Ser | His | Cys | Tyr | Pro | Ser | Gly | Trp | Gln | Ala | Arg | Leu |
| 65 | | | | | 70 | | | | | 75 | | | | | 80 |
| Gly | Met | Ile | Asn | Glu | Phe | His | Lys | Gln | Gly | Ser | Ala | Phe | Tyr | Phe | Gly |
| | | | | 85 | | | | | 90 | | | | | 95 | |
| Leu | Phe | Asp | Pro | Asp | Glu | Lys | Glu | Ile | Ile | Gly | Val | Ala | Asn | Phe | Ser |
| | | | 100 | | | | | 105 | | | | | 110 | | |
| Asn | Val | Val | Arg | Gly | Ser | Phe | His | Ala | Cys | Tyr | Leu | Gly | Tyr | Ser | Ile |
| | | 115 | | | | | 120 | | | | | 125 | | | |
| Gly | Gln | Lys | Trp | Gln | Gly | Lys | Gly | Leu | Met | Phe | Glu | Ala | Leu | Thr | Ala |
| | 130 | | | | | 135 | | | | | 140 | | | | |
| Ala | Ile | Arg | Tyr | Met | Gln | Arg | Thr | Gln | His | Ile | His | Arg | Ile | Met | Ala |
| 145 | | | | | 150 | | | | | 155 | | | | | 160 |
| Asn | Tyr | Met | Pro | His | Xaa | Xaa | Xaa | Xaa | Asn | Lys | Arg | Ser | Gly | Asp | Leu |
| | | | | 165 | | | | | 170 | | | | | 175 | |
| Leu | Ala | Arg | Leu | Gly | Phe | Glu | Lys | Glu | Gly | Tyr | Ala | Lys | Asp | Tyr | Leu |
| | | | 180 | | | | | 185 | | | | | 190 | | |
| Leu | Ile | Asp | Gly | Gln | Trp | Arg | Asp | His | Val | Leu | Thr | Ala | Leu | Thr | Thr |
| | | 195 | | | | | 200 | | | | | 205 | | | |
| Pro | Asp | Trp | Thr | Pro | Gly | Arg | Xaa | Xaa | Xaa | Xaa | Xaa | Xaa | Xaa | Xaa | Xaa |
| | 210 | | | | | 215 | | | | | 220 | | | | |
| Xaa | Xaa | Xaa | Xaa | Xaa | Xaa | Xaa | Xaa | Xaa | Xaa | Xaa | Xaa | Xaa | Xaa | Xaa | Xaa |
| 225 | | | | | 230 | | | | | 235 | | | | | 240 |

( 2 ) INFORMATION FOR SEQ ID NO:70:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:70:

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 1 | | | | 5 | | | | | 10 | | | | | 15 |
| Xaa | Xaa | Xaa | Xaa | Xaa | Xaa | Xaa | Xaa | Met | Glu | Thr | Glu | Ile | Lys | Val | Ser |
| | | | 20 | | | | | 25 | | | | | 30 | | |
| Glu | Ser | Leu | Glu | Leu | His | Ala | Val | Ala | Glu | Asn | His | Val | Lys | Pro | Leu |
| | | 35 | | | | | 40 | | | | | 45 | | | |

|   |   |   |   |   |   |   |   |   |   |   |   |   |   |   |
|---|---|---|---|---|---|---|---|---|---|---|---|---|---|---|
| Tyr | Gln | Leu | Ile | Cys | Lys | Asn | Lys | Thr | Trp | Leu | Gln | Gln | Ser | Leu | Asn |
|  | 50 |  |  |  | 55 |  |  |  | 60 |  |  |  |  |  |
| Trp | Pro | Gln | Phe | Val | Gln | Ser | Glu | Glu | Asp | Thr | Arg | Lys | Thr | Val | Gln |
| 65 |  |  |  |  | 70 |  |  |  | 75 |  |  |  |  | 80 |
| Gly | Asn | Val | Xaa | Met | Leu | His | Gln | Arg | Gly | Tyr | Ala | Lys | Met | Phe | Met |
|  |  |  |  | 85 |  |  |  |  | 90 |  |  |  |  | 95 |
| Ile | Phe | Xaa | Xaa | Lys | Glu | Asp | Glu | Leu | Ile | Gly | Val | Ile | Ser | Phe | Xaa |
|  |  |  | 100 |  |  |  |  | 105 |  |  |  |  | 110 |  |  |
| Asn | Arg | Ile | Glu | Pro | Leu | Asn | Lys | Thr | Ala | Glu | Ile | Gly | Tyr | Trp | Leu |
|  |  |  | 115 |  |  |  |  | 120 |  |  |  |  | 125 |  |  |
| Asp | Glu | Ser | His | Gln | Gly | Gln | Gly | Ile | Ile | Ser | Gln | Ala | Leu | Gln | Ala |
|  |  | 130 |  |  |  |  | 135 |  |  |  |  | 140 |  |  |  |
| Leu | Ile | His | His | Tyr | Ala | Gln | Ser | Gly | Glu | Leu | Arg | Arg | Phe | Val | Ile |
| 145 |  |  |  |  | 150 |  |  |  |  | 155 |  |  |  |  | 160 |
| Lys | Cys | Arg | Val | Asp | Xaa | Xaa | Xaa | Xaa | Asn | Pro | Gln | Ser | Asn | Gln | Val |
|  |  |  |  | 165 |  |  |  |  | 170 |  |  |  |  | 175 |  |
| Ala | Leu | Arg | Asn | Gly | Phe | Ile | Leu | Glu | Gly | Cys | Leu | Lys | Gln | Ala | Glu |
|  |  |  | 180 |  |  |  |  | 185 |  |  |  |  | 190 |  |  |
| Phe | Leu | Asn | Asp | Ala | Tyr | Asp | Asp | Val | Asn | Leu | Tyr | Ala | Arg | Ile | Ile |
|  |  | 195 |  |  |  |  | 200 |  |  |  |  | 205 |  |  |  |
| Asp | Ser | Gln | Xaa | Xaa | Xaa | Xaa | Xaa | Xaa | Xaa | Xaa | Xaa | Xaa | Xaa | Xaa | Xaa |
|  | 210 |  |  |  |  | 215 |  |  |  |  | 220 |  |  |  |  |
| Xaa | Xaa | Xaa | Xaa | Xaa | Xaa | Xaa | Xaa | Xaa | Xaa | Xaa | Xaa | Xaa | Xaa | Xaa | Xaa |
| 225 |  |  |  |  | 230 |  |  |  |  | 235 |  |  |  |  | 240 |

( 2 ) INFORMATION FOR SEQ ID NO:71:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:71:

|   |   |   |   |   |   |   |   |   |   |   |   |   |   |   |   |
|---|---|---|---|---|---|---|---|---|---|---|---|---|---|---|---|
| Xaa | Xaa | Xaa | Xaa | Xaa | Xaa | Xaa | Met | Leu | Trp | Ser | Ser | Asn | Asp | Val | Thr |
| 1 |  |  |  | 5 |  |  |  |  | 10 |  |  |  |  | 15 |  |
| Gln | Gln | Gly | Ser | Arg | Pro | Lys | Thr | Lys | Leu | Gly | Gly | Ser | Xaa | Met | Ser |
|  |  |  | 20 |  |  |  |  | 25 |  |  |  |  | 30 |  |  |
| Ile | Ile | Ala | Thr | Val | Lys | Ile | Gly | Pro | Asp | Glu | Ile | Ser | Ala | Met | Arg |
|  |  |  | 35 |  |  |  |  | 40 |  |  |  |  | 45 |  |  |
| Ala | Val | Leu | Asp | Leu | Phe | Gly | Lys | Glu | Phe | Glu | Asp | Ile | Pro | Thr | Tyr |
|  | 50 |  |  |  |  | 55 |  |  |  |  | 60 |  |  |  |  |
| Ser | Asp | Arg | Gln | Pro | Thr | Asn | Glu | Tyr | Leu | Ala | Asn | Leu | Leu | His | Ser |
| 65 |  |  |  |  | 70 |  |  |  |  | 75 |  |  |  |  | 80 |
| Glu | Thr | Phe | Ile | Ala | Leu | Ala | Ala | Phe | Asp | Arg | Gly | Thr | Ala | Ile | Gly |
|  |  |  |  | 85 |  |  |  |  | 90 |  |  |  |  | 95 |  |
| Gly | Leu | Ala | Xaa | Xaa | Ala | Tyr | Val | Leu | Pro | Lys | Phe | Glu | Gln | Ala | Arg |
|  |  |  | 100 |  |  |  |  | 105 |  |  |  |  | 110 |  |  |
| Ser | Glu | Xaa | Xaa | Xaa | Xaa | Xaa | Xaa | Ile | Tyr | Ile | Tyr | Asp | Leu | Ala | Val |
|  |  | 115 |  |  |  |  | 120 |  |  |  |  | 125 |  |  |  |
| Ala | Ser | Ser | His | Arg | Arg | Leu | Gly | Val | Ala | Thr | Ala | Leu | Ile | Ser | His |
|  |  | 130 |  |  |  |  | 135 |  |  |  |  | 140 |  |  |  |

```
Leu Lys Arg Xaa Val Ala Val Glu Leu Gly Ala Tyr Val Ile Tyr Val
145                 150                 155                 160

Gln Ala Asp Tyr Gly Xaa Xaa Xaa Xaa Asp Asp Pro Ala Val Ala Leu
                165             170                 175

Tyr Thr Lys Leu Gly Val Arg Glu Asp Val Met His Phe Asp Ile Asp
            180                 185                 190

Pro Arg Thr Ala Thr Xaa Xaa Xaa Xaa Xaa Xaa Xaa Xaa Xaa Xaa Xaa
        195             200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240
```

( 2 ) INFORMATION FOR SEQ ID NO:72:

( i ) SEQUENCE CHARACTERISTICS:
  ( A ) LENGTH: 240 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:72:

```
Xaa Xaa Xaa Xaa Xaa Xaa Xaa Met Leu Arg Ser Ser Asn Asp Val Thr
1               5                   10                  15

Gln Gln Gly Ser Arg Pro Lys Thr Lys Leu Gly Gly Ser Ser Met Gly
            20                  25                  30

Ile Ile Arg Thr Cys Arg Leu Gly Pro Asp Gln Val Lys Ser Met Arg
            35                  40                  45

Ala Ala Leu Asp Leu Phe Gly Arg Glu Phe Gly Asp Val Ala Thr Tyr
        50                  55                  60

Ser Gln His Gln Pro Asp Ser Asp Tyr Leu Gly Asn Leu Leu Arg Ser
65                  70                  75                  80

Lys Thr Phe Ile Ala Leu Ala Ala Phe Asp Gln Glu Ala Val Val Gly
                85                  90                  95

Ala Leu Ala Xaa Xaa Ala Tyr Val Leu Pro Lys Phe Glu Gln Ala Arg
            100                 105                 110

Ser Glu Xaa Xaa Xaa Xaa Xaa Xaa Ile Tyr Ile Tyr Asp Leu Ala Val
        115                 120                 125

Ser Gly Glu His Arg Arg Gln Gly Ile Ala Thr Ala Leu Ile Asn Leu
    130                 135                 140

Leu Lys His Xaa Glu Ala Asn Ala Leu Gly Ala Tyr Val Ile Tyr Val
145                 150                 155                 160

Gln Ala Asp Tyr Gly Xaa Xaa Xaa Xaa Asp Asp Pro Ala Val Ala Leu
                165             170                 175

Tyr Thr Lys Leu Gly Ile Arg Glu Glu Val Met His Phe Asp Ile Asp
            180                 185                 190

Pro Ser Thr Ala Thr Xaa Xaa Xaa Xaa Xaa Xaa Xaa Xaa Xaa Xaa Xaa
        195             200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240
```

( 2 ) INFORMATION FOR SEQ ID NO:73:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:73:

```
Met Thr Thr Leu Asp Asp Thr Ala Tyr Arg Tyr Arg Thr Ser Val Pro
 1               5                  10                  15
Gly Asp Ala Glu Ala Ile Glu Ala Leu Asp Gly Ser Phe Thr Thr Asp
            20                  25                  30
Thr Val Phe Arg Val Thr Ala Thr Gly Asp Gly Phe Thr Leu Arg Glu
                35                  40                  45
Val Pro Val Asp Pro Pro Leu Thr Lys Val Xaa Xaa Phe Pro Asp Asp
        50                  55                  60
Glu Ser Asp Asp Glu Ser Asp Asp Gly Glu Asp Gly Asp Pro Asp Ser
 65                  70                  75                  80
Arg Thr Phe Val Ala Tyr Gly Asp Xaa Xaa Xaa Xaa Xaa Xaa Asp Gly
                85                  90                  95
Asp Leu Ala Xaa Xaa Gly Phe Val Val Ile Ser Tyr Ser Ala Trp Asn
            100                 105                 110
Arg Arg Xaa Xaa Xaa Xaa Xaa Xaa Leu Thr Val Glu Asp Ile Glu Val
        115                 120                 125
Ala Pro Glu His Arg Gly His Gly Val Gly Arg Ala Leu Met Gly Leu
    130                 135                 140
Ala Thr Glu Xaa Phe Ala Gly Glu Arg Gly Ala Gly His Leu Trp Leu
145                 150                 155                 160
Glu Val Thr Asn Val Xaa Xaa Xaa Xaa Asn Ala Pro Ala Ile His Ala
                165                 170                 175
Tyr Arg Arg Met Gly Phe Thr Leu Cys Gly Leu Asp Thr Ala Leu Tyr
            180                 185                 190
Asp Gly Thr Ala Ser Asp Gly Glu Arg Gln Ala Leu Tyr Met Ser Met
        195                 200                 205
Pro Cys Pro Xaa Xaa Xaa Xaa Xaa Xaa Xaa Xaa Xaa Xaa Xaa Xaa Xaa
    210                 215                 220
Xaa Xaa Xaa Xaa Xaa Xaa Xaa Xaa Xaa Xaa Xaa Xaa Xaa Xaa Xaa Xaa
225                 230                 235                 240
```

( 2 ) INFORMATION FOR SEQ ID NO:74:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:74:

```
Met Thr Thr Thr His Gly Ser Thr Tyr Glu Phe Arg Ser Ala Arg Pro
```

|  | 1 |  |  |  | 5 |  |  |  |  | 10 |  |  |  |  | 15 |
|---|---|---|---|---|---|---|---|---|---|---|---|---|---|---|---|

Gly Asp Ala Glu Ala Ile Glu Gly Leu Asp Gly Ser Phe Thr Ser
                    20                      25                      30

Thr Val Phe Glu Val Asp Val Thr Gly Asp Gly Phe Ala Leu Arg Glu
             35                       40                       45

Val Pro Ala Asp Pro Pro Leu Val Lys Val Xaa Xaa Phe Pro Asp Asp
         50                      55                      60

Gly Gly Ser Asp Gly Glu Asp Gly Ala Glu Gly Glu Asp Ala Asp Ser
65                       70                      75                       80

Arg Thr Phe Val Ala Val Gly Ala Xaa Xaa Xaa Xaa Xaa Asp Gly
                     85                      90                      95

Asp Leu Ala Xaa Xaa Gly Phe Ala Ala Val Ser Tyr Ser Ala Trp Asn
                100                     105                     110

Gln Arg Xaa Xaa Xaa Xaa Xaa Xaa Leu Thr Ile Glu Asp Ile Glu Val
            115                     120                     125

Ala Pro Gly His Arg Gly Lys Gly Ile Gly Arg Val Leu Met Arg His
         130                     135                     140

Ala Ala Asp Xaa Phe Ala Arg Glu Arg Gly Ala Gly His Leu Trp Leu
145                      150                     155                     160

Glu Asn Thr Asn Val Xaa Xaa Xaa Xaa Asn Ala Pro Ala Ile His Ala
                    165                     170                     175

Tyr Arg Arg Met Gly Phe Ala Phe Cys Gly Leu Asp Ser Ala Leu Tyr
                 180                    185                     190

Gln Gly Thr Ala Ser Glu Gly Glu Xaa His Ala Leu Tyr Met Ser Met
                 195                    200                     205

Pro Cys Pro Xaa Xaa Xaa Xaa Xaa Xaa Xaa Xaa Xaa Xaa Xaa Xaa Xaa
         210                     215                     220

Xaa Xaa Xaa Xaa Xaa Xaa Xaa Xaa Xaa Xaa Xaa Xaa Xaa Xaa Xaa
225                      230                     235                     240

(2) INFORMATION FOR SEQ ID NO:75:

(i) SEQUENCE CHARACTERISTICS:
        (A) LENGTH: 240 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:75:

Xaa Xaa Xaa Xaa Xaa Xaa Xaa Xaa Met Lys Ile Ser Val Ile Pro Glu
1                        5                       10                      15

Gln Val Ala Glu Thr Leu Asp Ala Xaa Glu Asn His Phe Ile Val Arg
                    20                      25                      30

Glu Val Phe Asp Val His Leu Ser Asp Gln Gly Phe Glu Leu Ser Thr
             35                      40                       45

Arg Ser Val Ser Pro Tyr Arg Lys Asp Tyr Xaa Xaa Ile Ser Asp Asp
         50                      55                      60

Asp Ser Asp Glu Xaa Xaa Xaa Xaa Xaa Xaa Xaa Xaa Xaa Asp Ser
65                       70                      75                       80

Ala Cys Tyr Gly Ala Phe Xaa Ile Xaa Xaa Xaa Xaa Xaa Asp Gln
                     85                      90                      95

Glu Leu Val Xaa Xaa Gly Lys Ile Glu Leu Asn Xaa Ser Thr Trp Asn

```
            100                          105                          110
Asp Leu Xaa Xaa Xaa Xaa Xaa Ala Ser Ile Glu His Ile Val Val
        115                 120                 125

Ser His Thr His Arg Gly Lys Gly Val Ala His Ser Leu Ile Glu Phe
    130                 135                 140

Ala Lys Lys Xaa Trp Ala Leu Ser Arg Gln Leu Leu Gly Ile Arg Leu
145             150                 155                     160

Glu Thr Gln Thr Asn Xaa Xaa Xaa Xaa Asn Val Pro Ala Cys Asn Leu
                165                 170                 175

Tyr Ala Lys Cys Gly Phe Thr Leu Gly Gly Ile Asp Leu Phe Thr Tyr
            180             185                 190

Lys Thr Arg Pro Gln Val Ser Asn Glu Thr Ala Met Tyr Trp Tyr Trp
        195                 200                 205

Phe Ser Gly Ala Gln Asp Asp Ala Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                     240
```

( 2 ) INFORMATION FOR SEQ ID NO:76:

( i ) SEQUENCE CHARACTERISTICS:
       ( A ) LENGTH: 240 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:76:

```
Xaa Xaa Xaa Xaa Xaa Xaa Xaa Xaa Xaa Xaa Xaa Xaa Xaa Xaa Met
1               5                   10                  15

Ala Lys Phe Lys Ile Arg Pro Ala Thr Ala Ser Asp Cys Ser Xaa Xaa
            20                  25                  30

Xaa Xaa Asp Ile Leu Arg Leu Ile Lys Glu Leu Ala Lys Tyr Glu Tyr
        35                  40                  45

Met Glu Asp Gln Val Ile Leu Thr Glu Lys Asp Leu Gln Glu Asp Gly
    50                  55                  60

Phe Gly Glu His Pro Phe Tyr His Cys Leu Val Ala Glu Val Pro Lys
65                  70                  75                  80

Glu His Trp Thr Pro Xaa Xaa Xaa Xaa Xaa Glu Gly His Ser Ile Val
                85                  90                  95

Gly Phe Ala Xaa Xaa Met Tyr Tyr Phe Thr Tyr Asp Pro Trp Ile Gly
            100             105                 110

Lys Leu Xaa Xaa Xaa Xaa Xaa Xaa Leu Tyr Leu Glu Asp Phe Phe Val
        115                 120                 125

Met Ser Asp Tyr Arg Gly Phe Gly Ile Gly Ser Glu Ile Leu Lys Asn
130                 135                 140

Leu Ser Gln Xaa Val Ala Met Lys Cys Arg Cys Ser Ser Met His Phe
145             150                 155                     160

Leu Val Ala Glu Trp Xaa Xaa Xaa Asn Glu Pro Ser Ile Asn Phe
                165                 170             175

Tyr Lys Arg Arg Gly Ala Ser Asp Leu Ser Ser Glu Glu Gly Trp Xaa
            180                 185                 190

Xaa Xaa Xaa Xaa Arg Leu Phe Lys Ile Asp Lys Glu Tyr Leu Leu Lys
```

|  | 195 |  |  |  | 200 |  |  |  |  | 205 |  |  |  |
|---|---|---|---|---|---|---|---|---|---|---|---|---|---|
| Met | Ala | Ala | Glu | Glu | Xaa | Xaa | Xaa | Xaa | Xaa | Xaa | Xaa | Xaa | Xaa |
| 210 | | | | | 215 | | | | | 220 | | | |
| Xaa | Xaa | Xaa | Xaa | Xaa | Xaa | Xaa | Xaa | Xaa | Xaa | Xaa | Xaa | Xaa | Xaa |
| 225 | | | | | 230 | | | | | 235 | | | 240 |

( 2 ) INFORMATION FOR SEQ ID NO:77:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:77:

| Xaa | Xaa | Xaa | Xaa | Xaa | Xaa | Xaa | Xaa | Xaa | Xaa | Xaa | Xaa | Xaa | Xaa | Met |
|---|---|---|---|---|---|---|---|---|---|---|---|---|---|---|
| 1 | | | | 5 | | | | | 10 | | | | | 15 |
| Ala | Lys | Phe | Val | Ile | Arg | Pro | Ala | Thr | Ala | Ala | Asp | Cys | Ser | Xaa | Xaa |
| | | | 20 | | | | 25 | | | | | 30 | | | |
| Xaa | Xaa | Asp | Ile | Leu | Arg | Leu | Ile | Lys | Glu | Leu | Ala | Lys | Tyr | Glu | Tyr |
| | | 35 | | | | 40 | | | | | 45 | | | | |
| Met | Glu | Glu | Gln | Val | Ile | Leu | Thr | Glu | Lys | Asp | Leu | Leu | Glu | Asp | Gly |
| | 50 | | | | | 55 | | | | | 60 | | | | |
| Phe | Gly | Glu | His | Pro | Phe | Tyr | His | Cys | Leu | Val | Ala | Glu | Val | Pro | Lys |
| 65 | | | | | 70 | | | | | 75 | | | | | 80 |
| Glu | His | Trp | Thr | Pro | Xaa | Xaa | Xaa | Xaa | Xaa | Glu | Gly | His | Ser | Ile | Val |
| | | | | 85 | | | | | | 90 | | | | | 95 |
| Gly | Phe | Ala | Xaa | Xaa | Met | Tyr | Tyr | Phe | Thr | Tyr | Asp | Pro | Trp | Ile | Gly |
| | | | 100 | | | | | 105 | | | | | 110 | | |
| Lys | Leu | Xaa | Xaa | Xaa | Xaa | Xaa | Xaa | Leu | Tyr | Leu | Glu | Asp | Phe | Phe | Val |
| | | 115 | | | | | 120 | | | | | 125 | | | |
| Met | Ser | Asp | Tyr | Arg | Gly | Phe | Gly | Ile | Gly | Ser | Glu | Ile | Leu | Lys | Asn |
| | 130 | | | | | 135 | | | | | 140 | | | | |
| Leu | Ser | Gln | Xaa | Val | Ala | Met | Arg | Cys | Arg | Cys | Ser | Ser | Met | His | Phe |
| 145 | | | | | 150 | | | | | 155 | | | | | 160 |
| Leu | Val | Ala | Glu | Trp | Xaa | Xaa | Xaa | Xaa | Asn | Glu | Pro | Ser | Ile | Asn | Phe |
| | | | | 165 | | | | | 170 | | | | | 175 | |
| Tyr | Lys | Arg | Arg | Gly | Ala | Ser | Asp | Leu | Ser | Ser | Glu | Glu | Gly | Trp | Xaa |
| | | | 180 | | | | | 185 | | | | | 190 | | |
| Xaa | Xaa | Xaa | Xaa | Arg | Leu | Phe | Lys | Ile | Asp | Lys | Glu | Tyr | Leu | Leu | Lys |
| | | | 195 | | | | 200 | | | | | 205 | | | |
| Met | Ala | Thr | Glu | Glu | Xaa | Xaa | Xaa | Xaa | Xaa | Xaa | Xaa | Xaa | Xaa | Xaa |
| | 210 | | | | | 215 | | | | | 220 | | | | |
| Xaa | Xaa | Xaa | Xaa | Xaa | Xaa | Xaa | Xaa | Xaa | Xaa | Xaa | Xaa | Xaa | Xaa | Xaa |
| 225 | | | | | 230 | | | | | 235 | | | | | 240 |

( 2 ) INFORMATION FOR SEQ ID NO:78:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( i i ) MOLECULE TYPE: peptide 5,650,553

113                                                                                                                          114

-continued (iii) HYPOTHETICAL: NO (iv) ANTI-SENSE: NO (xi) SEQUENCE DESCRIPTION: SEQ ID NO:78:

| Xaa | Xaa | Xaa | Xaa | Xaa | Xaa | Xaa | Xaa | Xaa | Xaa | Xaa | Xaa | Xaa | Xaa | Met |
|---|---|---|---|---|---|---|---|---|---|---|---|---|---|---|
| 1 | | | | 5 | | | | | 10 | | | | | 15 |

| Asn | His | Ala | Gln | Leu | Arg | Arg | Val | Thr | Ala | Glu | Ser | Phe | Ala | His | Tyr |
|---|---|---|---|---|---|---|---|---|---|---|---|---|---|---|---|
| | | | 20 | | | | | 25 | | | | | 30 | | |

| Arg | His | Gly | Leu | Ala | Gln | Leu | Leu | Phe | Glu | Thr | Val | His | Gly | Gly | Xaa |
|---|---|---|---|---|---|---|---|---|---|---|---|---|---|---|---|
| | | 35 | | | | 40 | | | | | | 45 | | | |

| Xaa | Ala | Ser | Val | Gly | Phe | Met | Ala | Asp | Leu | Asp | Met | Gln | Gln | Ala | Tyr |
|---|---|---|---|---|---|---|---|---|---|---|---|---|---|---|---|
| 50 | | | | | | 55 | | | | | 60 | | | | |

| Ala | Trp | Cys | Asp | Gly | Leu | Lys | Ala | Asp | Ile | Ala | Ala | Gly | Ser | Leu | Leu |
|---|---|---|---|---|---|---|---|---|---|---|---|---|---|---|---|
| 65 | | | | | 70 | | | | 75 | | | | | 80 | |

| Leu | Trp | Val | Val | Ala | Xaa | Xaa | Xaa | Xaa | Xaa | Glu | Asp | Asp | Asn | Val | Leu |
|---|---|---|---|---|---|---|---|---|---|---|---|---|---|---|---|
| | | | | 85 | | | | | 90 | | | | | 95 | |

| Ala | Ser | Ala | Xaa | Xaa | Gln | Leu | Ser | Leu | Cys | Gln | Lys | Pro | Asn | Gly | Leu |
|---|---|---|---|---|---|---|---|---|---|---|---|---|---|---|---|
| | | | 100 | | | | | 105 | | | | | 110 | | |

| Asn | Arg | Xaa | Xaa | Xaa | Xaa | Xaa | Xaa | Ala | Glu | Val | Gln | Lys | Leu | Met | Val |
|---|---|---|---|---|---|---|---|---|---|---|---|---|---|---|---|
| | | 115 | | | | | 120 | | | | | 125 | | | |

| Leu | Pro | Ser | Ala | Arg | Gly | Arg | Gly | Leu | Gly | Arg | Gln | Leu | Met | Asp | Glu |
|---|---|---|---|---|---|---|---|---|---|---|---|---|---|---|---|
| | 130 | | | | | 135 | | | | | 140 | | | | |

| Val | Glu | Gln | Xaa | Val | Ala | Val | Lys | His | Lys | Arg | Gly | Leu | Leu | His | Leu |
|---|---|---|---|---|---|---|---|---|---|---|---|---|---|---|---|
| 145 | | | | | 150 | | | | 155 | | | | | | 160 |

| Asp | Thr | Glu | Ala | Xaa | Xaa | Xaa | Xaa | Xaa | Gly | Ser | Val | Ala | Glu | Ala | Phe |
|---|---|---|---|---|---|---|---|---|---|---|---|---|---|---|---|
| | | | | 165 | | | | | 170 | | | | | 175 | |

| Tyr | Ser | Ala | Leu | Ala | Tyr | Thr | Arg | Val | Gly | Glu | Leu | Pro | Gly | Tyr | Cys |
|---|---|---|---|---|---|---|---|---|---|---|---|---|---|---|---|
| | | | 180 | | | | | 185 | | | | | 190 | | |

| Ala | Thr | Pro | Asp | Gly | Arg | Leu | His | Pro | Thr | Ala | Ile | Tyr | Phe | Lys | Thr |
|---|---|---|---|---|---|---|---|---|---|---|---|---|---|---|---|
| | | 195 | | | | | 200 | | | | | 205 | | | |

| Leu | Gly | Gln | Pro | Thr | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| | 210 | | | | | 215 | | | | | 220 | | | | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 225 | | | | | 230 | | | | | 235 | | | | | 240 |

(2) INFORMATION FOR SEQ ID NO:79:

(i) SEQUENCE CHARACTERISTICS:
        (A) LENGTH: 240 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:79:

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 1 | | | | 5 | | | | | 10 | | | | | 15 |

| Xaa | Xaa | Xaa | Xaa | Met | Pro | Asn | Val | Thr | Ile | Ala | Arg | Glu | Ser | Pro | Leu |
|---|---|---|---|---|---|---|---|---|---|---|---|---|---|---|---|
| | | | 20 | | | | | 25 | | | | | 30 | | |

| Gln | Asp | Ala | Val | Val | Gln | Leu | Ile | Glu | Glu | Leu | Asp | Arg | Xaa | Xaa | Xaa |
|---|---|---|---|---|---|---|---|---|---|---|---|---|---|---|---|
| | | 35 | | | | 40 | | | | | 45 | | | | |

| Xaa | Xaa | Xaa | Xaa | Xaa | Tyr | Leu | Gly | Asp | Leu | Tyr | Pro | Ala | Glu | Ser | Asn |
|---|---|---|---|---|---|---|---|---|---|---|---|---|---|---|---|
| | 50 | | | | | 55 | | | | | 60 | | | | |

His Leu Xaa Xaa Xaa Leu Asp Leu Gln Thr Leu Ala Lys Pro Asp Ile
65                  70                  75                  80

Arg Phe Leu Val Ala Xaa Xaa Xaa Xaa Arg Arg Ser Gly Thr Val
              85                  90                  95

Val Gly Cys Xaa Xaa Gly Ala Ile Ala Ile Asp Thr Glu Gly Gly Tyr
            100             105                 110

Xaa Xaa Xaa Xaa Xaa Xaa Xaa Xaa Gly Glu Val Lys Arg Met Phe Val
            115                 120                 125

Gln Pro Thr Ala Arg Gly Gly Gln Ile Gly Arg Arg Leu Leu Glu Arg
    130             135                 140

Ile Glu Asp Xaa Glu Ala Arg Ala Ala Gly Leu Ser Ala Leu Leu Leu
145                 150                 155                 160

Glu Thr Gly Val Tyr Xaa Xaa Xaa Xaa Gln Ala Thr Arg Ile Ala Leu
              165                 170                 175

Tyr Arg Lys Gln Gly Phe Ala Asp Arg Gly Pro Phe Gly Pro Tyr Gly
            180                 185                 190

Pro Asp Pro Leu Ser Leu Phe Met Glu Lys Pro Leu Xaa Xaa Xaa Xaa
        195             200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

( 2 ) INFORMATION FOR SEQ ID NO:80:

( i ) SEQUENCE CHARACTERISTICS:
  ( A ) LENGTH: 240 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:80:

Xaa Xaa Xaa Xaa Xaa Met Pro Ile Asn Ile Arg Arg Ala Thr Xaa Ile
1               5                   10                  15

Asn Asp Ile Ile Cys Met Gln Asn Ala Asn Leu His Asn Leu Pro Glu
            20                  25                  30

Asn Tyr Met Met Lys Tyr Tyr Met Tyr His Thr Leu Ser Trp Pro Glu
        35                  40                  45

Ala Ser Phe Val Ala Thr Thr Thr Leu Asp Cys Glu Asp Ser Asp
    50                  55                  60

Glu Gln Asp Glu Asn Asp Lys Leu Glu Leu Thr Leu Asp Gly Thr Asn
65                  70                  75                  80

Asp Gly Arg Thr Ile Lys Leu Asp Pro Thr Tyr Leu Ala Pro Gly Glu
            85                  90                  95

Lys Leu Val Xaa Xaa Gly Tyr Val Leu Val Lys Met Asn Asp Asp Pro
            100             105                 110

Asp Gln Gln Asn Glu Pro Pro Asn Gly His Ile Thr Ser Leu Ser Val
        115                 120                 125

Met Arg Thr Tyr Arg Arg Met Gly Ile Ala Glu Asn Leu Met Arg Gln
    130                 135                 140

Ala Leu Phe Ala Leu Arg Glu Val His Gln Ala Glu Tyr Val Ser Leu
145                 150                 155                 160

|  |  |  |  |  |  |  |  |  |  |  |  |  |  |  |
|---|---|---|---|---|---|---|---|---|---|---|---|---|---|---|
| His | Val | Arg | Gln | Ser 165 | Xaa | Xaa | Xaa | Asn 170 | Arg | Ala | Ala | Leu | His 175 | Leu |
| Tyr | Arg | Asp | Thr 180 | Leu | Ala | Phe | Glu | Val 185 | Leu | Ser | Xaa | Xaa | Xaa 190 | Ile |
| Glu | Lys | Ser 195 | Tyr | Tyr | Gln | Asp | Gly 200 | Glu | Asp | Ala | Tyr | Ala 205 | Met | Lys | Lys |
| Val | Leu 210 | Lys | Leu | Glu | Glu | Leu 215 | Gln | Ile | Ser | Asn | Xaa 220 | Xaa | Xaa | Phe | Thr |
| His 225 | Arg | Arg | Leu | Lys | Glu 230 | Asn | Glu | Glu | Lys | Leu 235 | Glu | Asp | Asp | Leu | Glu 240 |

( 2 ) INFORMATION FOR SEQ ID NO:81:

( i ) SEQUENCE CHARACTERISTICS:
( A ) LENGTH: 240 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:81:

|  |  |  |  |  |  |  |  |  |  |  |  |  |  |  |
|---|---|---|---|---|---|---|---|---|---|---|---|---|---|---|
| Met 1 | Glu | Ile | Val | Tyr 5 | Lys | Pro | Leu | Asp | Ile 10 | Arg | Asn | Glu | Glu | Gln 15 | Phe |
| Ala | Ser | Ile | Lys 20 | Lys | Leu | Ile | Asp | Ala 25 | Asp | Leu | Ser | Glu | Pro 30 | Tyr | Ser |
| Ile | Tyr | Val 35 | Tyr | Arg | Tyr | Phe | Leu 40 | Asn | Gln | Xaa | Xaa | Xaa 45 | Trp | Pro | Glu |
| Leu | Thr 50 | Tyr | Ile | Ala | Xaa | Xaa 55 | Xaa | Xaa | Xaa | Xaa | Xaa 60 | Xaa | Xaa | Xaa | Xaa |
| Xaa 65 | Xaa | Xaa | Xaa | Xaa | Xaa 70 | Xaa | Xaa | Xaa | Xaa | Xaa 75 | Val | Asp | Asn | Lys | Ser 80 |
| Gly | Thr | Pro | Asn | Ile 85 | Pro | Xaa | Xaa | Xaa | Xaa 90 | Xaa | Xaa | Xaa | Xaa | Xaa 95 |
| Xaa | Xaa | Ile | Xaa 100 | Xaa | Gly | Cys | Ile | Val 105 | Cys | Lys | Met | Asp | Xaa 110 | Xaa | Xaa |
| Pro | His | Arg 115 | Asn | Val | Arg | Leu | Arg 120 | Gly | Tyr | Ile | Gly | Met 125 | Leu | Ala | Val |
| Glu | Ser 130 | Thr | Tyr | Arg | Gly | His 135 | Gly | Ile | Ala | Lys | Lys 140 | Leu | Val | Glu | Ile |
| Ala 145 | Ile | Asp | Lys | Met | Gln 150 | Arg | Glu | His | Cys | Asp 155 | Glu | Xaa | Ile | Met | Leu 160 |
| Glu | Thr | Glu | Val | Glu 165 | Xaa | Xaa | Xaa | Xaa | Asn 170 | Ser | Ala | Ala | Leu | Asn 175 | Leu |
| Tyr | Xaa | Glu | Gly 180 | Met | Gly | Phe | Ile | Arg 185 | Met | Lys | Xaa | Xaa | Xaa 190 | Arg |
| Met | Phe | Arg 195 | Tyr | Tyr | Leu | Asn | Glu 200 | Gly | Asp | Ala | Phe | Lys 205 | Leu | Xaa | Xaa |
| Ile | Leu 210 | Pro | Leu | Thr | Glu | Lys 215 | Ser | Cys | Thr | Arg | Ser 220 | Thr | Phe | Leu | Met |
| His 225 | Gly | Arg | Leu | Ala | Thr 230 | Xaa | Xaa | Xaa | Xaa | Xaa 235 | Xaa | Xaa | Xaa | Xaa | Xaa 240 |

( 2 ) INFORMATION FOR SEQ ID NO:82:

(i) SEQUENCE CHARACTERISTICS:
    (A) LENGTH: 240 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:82:

| Xaa | Xaa | Xaa | Xaa | Xaa | Xaa | Xaa | Xaa | Xaa | Xaa | Xaa | Xaa | Xaa | Xaa | Xaa |
| 1 | | | | 5 | | | | | 10 | | | | | 15 |
| Xaa | Xaa | Xaa | Xaa | Xaa | Xaa | Xaa | Xaa | Xaa | Xaa | Xaa | Xaa | Xaa | Xaa | Xaa |
| | | | 20 | | | | | 25 | | | | | 30 | |
| Met | Asn | Tyr | Gln | Ile | Val | Asn | Ile | Ala | Glu | Cys | Ser | Asn | Tyr | Gln | Leu |
| | | 35 | | | | | 40 | | | | | 45 | | | |
| Glu | Ala | Ala | Asn | Ile | Leu | Thr | Glu | Ala | Phe | Asn | Asp | Leu | Gly | Asn | Asn |
| | 50 | | | | | 55 | | | | | 60 | | | | |
| Ser | Trp | Pro | Asp | Met | Thr | Ser | Ala | Thr | Lys | Glu | Val | Lys | Glu | Cys | Ile |
| 65 | | | | | 70 | | | | | 75 | | | | | 80 |
| Glu | Ser | Pro | Asn | Leu | Cys | Phe | Gly | Leu | Leu | Ile | Asn | Asn | Ser | Leu | Val |
| | | | | 85 | | | | | 90 | | | | | 95 | |
| Gly | Trp | Ile | Xaa | Xaa | Gly | Leu | Arg | Pro | Met | Tyr | Lys | Glu | Thr | Trp | Glu |
| | | | 100 | | | | | 105 | | | | | 110 | | |
| Xaa | Xaa | Xaa | Xaa | Xaa | Xaa | Xaa | Xaa | Xaa | Leu | His | Pro | Leu | Val | Val |
| | | 115 | | | | | 120 | | | | | 125 | | |
| Arg | Pro | Asp | Tyr | Gln | Asn | Lys | Gly | Ile | Gly | Lys | Ile | Leu | Leu | Lys | Glu |
| | 130 | | | | | 135 | | | | | 140 | | | | |
| Leu | Glu | Asn | Arg | Xaa | Ala | Arg | Glu | Gln | Gly | Ile | Ile | Gly | Ile | Ala | Leu |
| 145 | | | | | 150 | | | | | 155 | | | | | 160 |
| Gly | Thr | Asp | Asp | Glu | Tyr | Tyr | Arg | Thr | Ser | Leu | Ser | Leu | Ile | Thr | Ile |
| | | | | 165 | | | | | 170 | | | | | 175 | |
| Thr | Glu | Asp | Asn | Ile | Phe | Asp | Ser | Ile | Lys | Asn | Ile | Lys | Asn | Ile | Asn |
| | | | 180 | | | | | 185 | | | | | 190 | | |
| Lys | His | Pro | Tyr | Glu | Phe | Tyr | Gln | Lys | Asn | Gly | Tyr | Tyr | Ile | Val | Gly |
| | | 195 | | | | | 200 | | | | | 205 | | | |
| Ile | Ile | Pro | Asn | Ala | Asn | Gly | Lys | Asn | Lys | Pro | Asp | Ile | Trp | Met | Trp |
| | 210 | | | | | 215 | | | | | 220 | | | | |
| Lys | Ser | Leu | Ile | Lys | Glu | Xaa | Xaa | Xaa | Xaa | Xaa | Xaa | Xaa | Xaa | Xaa |
| 225 | | | | | 230 | . | | | | 235 | | | | | 240 |

PLANT GENES FOR SENSITIVITY TO ETHYLENE AND PATHOGENS

REFERENCE TO RELATED APPLICATIONS

This application is a continuation-in-part of U.S. application Ser. No. 08/003,311, filed Jan. 12, 1993, now U.S. Pat. No. 5,444,166, which is a continuation-in-part of U.S. application Ser. No. 928,464, filed Aug. 10, 1992 now U.S. Pat. No. 5,367,065; this application is also a continuation-in-part of U.S. application Ser. No. 08/171,207, filed Dec. 21, 1993, which is a continuation of U.S. application Ser. No. 899,262, filed Jun. 16, 1992, now abandoned; the disclosures of which are hereby incorporated in their entirety.

REFERENCE TO GOVERNMENT GRANTS

This work was supported in part by research grants from the National Institutes Of Health GM-26379 and National Science Foundation grant IBN-92-05342. The United States Government may have certain rights in this invention.

BACKGROUND OF THE INVENTION

Ethylene, a gaseous plant hormone, is involved in the regulation of a number of plant processes ranging from growth and development to fruit ripening. As in animal systems, response of plants to disease not only involves static processes, but also involves inducible defense mechanisms. One of the earliest detectable event to occur during plant-pathogen interaction is a rapid increase in ethylene biosynthesis. Ethylene biosynthesis, in response to pathogen invasion, correlates with increased defense mechanisms, chlorosis, senescence and abscission. The molecular mechanisms underlying operation of ethylene action, however, are unknown. Nonetheless, ethylene produced in response to biological stress is known to regulate the rate of transcription of specific plant genes. A variety of biological stresses can induce ethylene production in plants including wounding, bacterial, viral or fungal infection as can treatment with elicitors, such as glycopeptide elicitor preparations (prepared by chemical extraction from fungal pathogen cells). Researchers have found, for example, that treatment of plants with ethylene generally increases the level of many pathogen-inducible "defense proteins", including β-1,3-glucanase, chitinase, L-phenylalanine ammonia lyase, and hydroxyproline-rich glycoproteins. The genes for these proteins can be transcriptionally activated by ethylene and their expression can be blocked by inhibitors of ethylene biosynthesis. Researchers have also characterized a normal plant response to the production or administration of ethylene, as a so-called "triple response". The triple response involves inhibition of root and stem elongation, radial swelling of the stem and absence of normal geotropic response (diageotropism).

Ethylene is one of five well-established plant hormones. It mediates a diverse array of plant responses including fruit ripening, leaf abscission and flower senescence.

The pathway for ethylene biosynthesis has been established (FIG. 6). Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway, see Kende, *Plant Physiol.* 1989, 91, 1–4. This enzyme has been cloned from several sources, see Sato et al., *PNAS*, (USA) 1989, 86, 6621; Van Der Straeten et al., *PNAS*, (USA) 1990, 87, 4859–4863; Nakajima et al., *Plant Cell Physiol.* 1990, 29, 989. The conversion of ACC to ethylene is catalyzed by ethylene forming enzyme (EFE), which has been recently cloned (Spanu et al., *EMBO J* 1991, 10, 2007. Aminoethoxyvinylglycine (AVG) and α-aminoisobutyric acid (AIB) have been shown to inhibit ACC synthase and EFE respectively. Ethylene binding is inhibited non-competitively by silver, and competitively by several compounds, the most effective of which is trans-cyclooctane. ACC synthase is encoded by a highly divergent gene family in tomato and Arabidopsis (Theologis, A., *Cell* 70:181 (1992)). ACC oxidase, which converts ACC to ethylene, is expressed constitutively in most tissues (Yang et al., *Ann. Rev. Plant Physiol.* 1984, 35, 155), but is induced during fruit ripening (Gray et al. *Cell* 1993 72, 427). It has been shown to be a dioxygenase belonging to the $Fe^{2+}$/ascorbate oxidase superfamily (McGarvey et al., *Plant Physiol.* 1992, 98, 554).

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901, Neljubow, D., *Pflanzen Beih. Bot. Zentralb.*, 1901, 10, 128. In Arabidopsis, a typical triple response consists of a shortening and radial swelling of the hypocotyl, an inhibition of root elongation and an exaggeration of the curvature of the apical hook (FIGS. 7 and 16). Etiolated morphology is dramatically altered by stress conditions which induce ethylene production the ethylene-induced "triple response" may provide the seedling with additional strength required for penetration of compact soils, see Harpham et al., *Annals of Bot.*, 1991, 68, 55. Ethylene may also be important for other stress responses. ACC synthase gene expression and ethylene production is induced by many types of biological and physical stress, such as wounding and pathogen infection, see Boller, T., in *The Plant Hormone Ethylene*, A. K. Mattoo and J. C. Suttle eds., 293–314, 1991, CRC Press, Inc. Boca Raton and Yu, Y. et al., *Plant Phys.*, 1979, 63, 589, Abeles et al. 1992 Second Edition San Diego, Calif. Academic Press; and Gray et al. *Plant Mol Biol.* 1992 19, 69.

A number of researchers have identified the interaction between *Arabidopsis thaliana* and *Pseudomonas syringae* bacteria; Whalen et al., "Identification of *Pseudomonas syringae* Pathogens of Arabidopsis and a Bacterial Locus Determining Avirulence on Both Arabidopsis and Soybean", *The Plant Cell* 1991, 3, 49, Dong et al., "Induction of Arabidopsis Defense Genes by Virulent and Avirulent *Pseudomonas syringae* Strains and by a Cloned Avirulence Gene", *The Plant Cell* 1991, 3, 61, and Debener et al., "Identification and Molecular Mapping of a Single *Arabidopsis thaliana* Locus Determining Resistance to a Phytopathogenic *Pseudomonas syringae* isolate", *The Plant Journal* 1991, 1, 289. *P. syringae* pv. tomato (Pst) strains are pathogenic on Arabidopsis. A single bacterial gene, avrRpt2, was isolated that controls pathogen avirulence on specific Arabidopsis host genotype Col-0.

Bent, A. F., et al., "Disease Development in Ethylene-Insensitive *Arabidopsis thaliana* Infected with Virulent and Avirulent Pseudomonas and Xanthomonas Pathogens", *Molecular Plant-Microbe Interactions* 1992, 5, 372; Agrios, G. N., *Plant Pathology* 1988, 126, Academic Press, San Diego; and Mussel, H., "Tolerance to Disease", page 40, in *Plant Disease: An Advanced Treatise*, Volume 5, Hotsfall, J. G. and Cowling, E. B., eds., 1980, Academic Press, New York, establish the art recognized definitions of tolerance, susceptibility, and resistance. Tolerance is defined for purposes of the present invention as growth of a pathogen in a plant where the plant does not sustain damage. Resistance is defined as the inability of a pathogen to grow in a plant and no damage to the plant results. Susceptibility is indicated by pathogen growth with plant damage.

Regardless of the molecular mechanisms involved, the normal ethylene response of a plant to pathogen invasion has been thought to have a cause and effect relationship in the ability of a plant to fight off plant pathogens. Plants insensitive in any fashion to ethylene were believed to be incapable of eliciting a proper defense response to pathogen invasion, and thus unable to initiate proper defense mechanisms. As such, ethylene insensitive plants were thought to be less disease tolerant.

The induction of disease responses in plants requires recognition of pathogens or pathogen-induced symptoms. In a large number of plant-pathogen interactions, successful resistance is observed when the plant has a resistance gene with functional specificity for pathogens that carry a particular avirulence gene. If the plant and pathogen carry resistance and avirulence genes with matched specificity, disease spread is curtailed and a hypersensitive response involving localized cell death and physical isolation of the pathogen typically occurs. In the absence of matched resistance and avirulence genes, colonization and tissue damage proceed past the site of initial infection and disease is observed.

A better understanding of plant pathogen tolerance is needed. Also needed is the development of methods for improving the tolerance of plants to pathogens, as well as the development of easy and efficient methods for identifying pathogen tolerant plants.

Genetic and molecular characterization of several gene loci and protein products is set forth in the present invention. The results will reveal interactions among modulatory components of the ethylene action pathway and provide insight into how plant hormones function. Thus, the quantity, quality and longevity of food, such as fruits and vegetables, and other plant products such as flowers, will be improved thereby providing more products for market in both developed and underdeveloped countries.

SUMMARY OF THE INVENTION

The present invention is directed to nucleic acid sequences for ethylene insensitive, EIN loci and corresponding amino acid sequences. Several ein wild type sequences, mutations, amino acid sequences, and protein products are included within the scope of the present invention. The nucleic acid sequences set forth in SEQUENCE ID NUMBERS 1 and 2 for ein2; 4, 5, 7, 9, and 11 for ein3 and eil1, eil2, eil3; as well as amino acid sequences set forth in SEQUENCE ID NUMBERS 3 for ein2; 6, 8, 10, 12, and 13 for ein3 and eil1, eil2, eil3; are particular embodiments of the present invention.

The present invention is also directed to nucleic acid sequences for hookless1, HLS1, alleles and amino acid sequences. Wild type and mutated nucleic acid sequences, amino acid sequences and proteins are included within the scope of the present invention. The nucleic acid sequences of hls1 are set forth in SEQUENCE ID NUMBERS: 14 and 15; the amino acid sequences are set forth in SEQUENCE ID NUMBER: 16.

These and other aspects of the invention will become more apparent from the following detailed description when taken in conjunction with the following figures.

BRIEF DESCRIPTION OF THE FIGURES

FIGS. 5A, 5B and 5C exhibit the sequence of the EIN2 locus. Genomic DNA sequence (SEQUENCE ID NO: 1) is shown in lower case letters, cDNA sequence (SEQUENCE ID NO: 2) is shown in capitol letters. The predicted peptide sequence (SEQUENCE ID NO: 3) is displayed under the corresponding nucleic acid codons.

FIG. 7A is a cross section of the seedling body of a seed plant. FIG. 7B is a perspective view of a developing seed plant.

FIGS. 8A and 8B identify the protein sequences of eil1, ein3, eil2, eil3, and a common consensus protein sequence representing all four of the individual protein sequences.

FIG. 9 displays the EIN3 gene structure and mutants. Also set forth in FIG. 9 is the predicted polypeptide acidity and basicity, as well as Ash repeats.

FIGS. 15A and 15B identify the protein sequences of Arabidopsis HLS1 and acetyl transferases in *E. coli*, Pseudomonas, Streptomyces, Mouse, Human, Azospirillum, Yeast, and Citrobacter. A consensus sequence representing common amino acids of the sequences is also provided.

FIGS. 19A-D display EIN3 sequences. FIG. 19A sets forth EIN3 cDNA (SEQUENCE ID NO: 4), FIGS. 19B and 19C set forth EIN3 genomic DNA (SEQUENCE ID NO: 5), and FIG. 19D sets forth EIN3 protein sequence (SEQUENCE ID NO: 6).

FIGS. 20A and 20B display EIL1 sequences. FIG. 20A sets forth EIL1 cDNA (SEQUENCE ID NO: 7), FIG. 20B sets forth EIL1 peptide sequence (SEQUENCE ID NO: 8).

FIGS. 21A and 21B display EIL2 sequences. FIG. 21A sets forth EIL2 cDNA (SEQUENCE ID NO: 9), FIG. 21B sets forth EIL2 peptide sequence (SEQUENCE ID NO: 10).

FIG. 22 displays EIL3 sequence. FIG. 22A sets forth EIL3 cDNA (SEQUENCE ID NO: 11). EIL3 peptide sequence is set forth in SEQUENCE ID NO: 12.

FIGS. 23A-D display HLS1 sequences. FIG. 23A sets forth HLS1 cDNA (SEQUENCE ID NO: 14), FIGS. 23B and 23C set forth HLS1 genomic DNA sequence (SEQUENCE ID NO: 15), and FIG. 23D sets forth HLS1 peptide sequence.

DETAILED DESCRIPTION OF THE INVENTION

Figure 1:
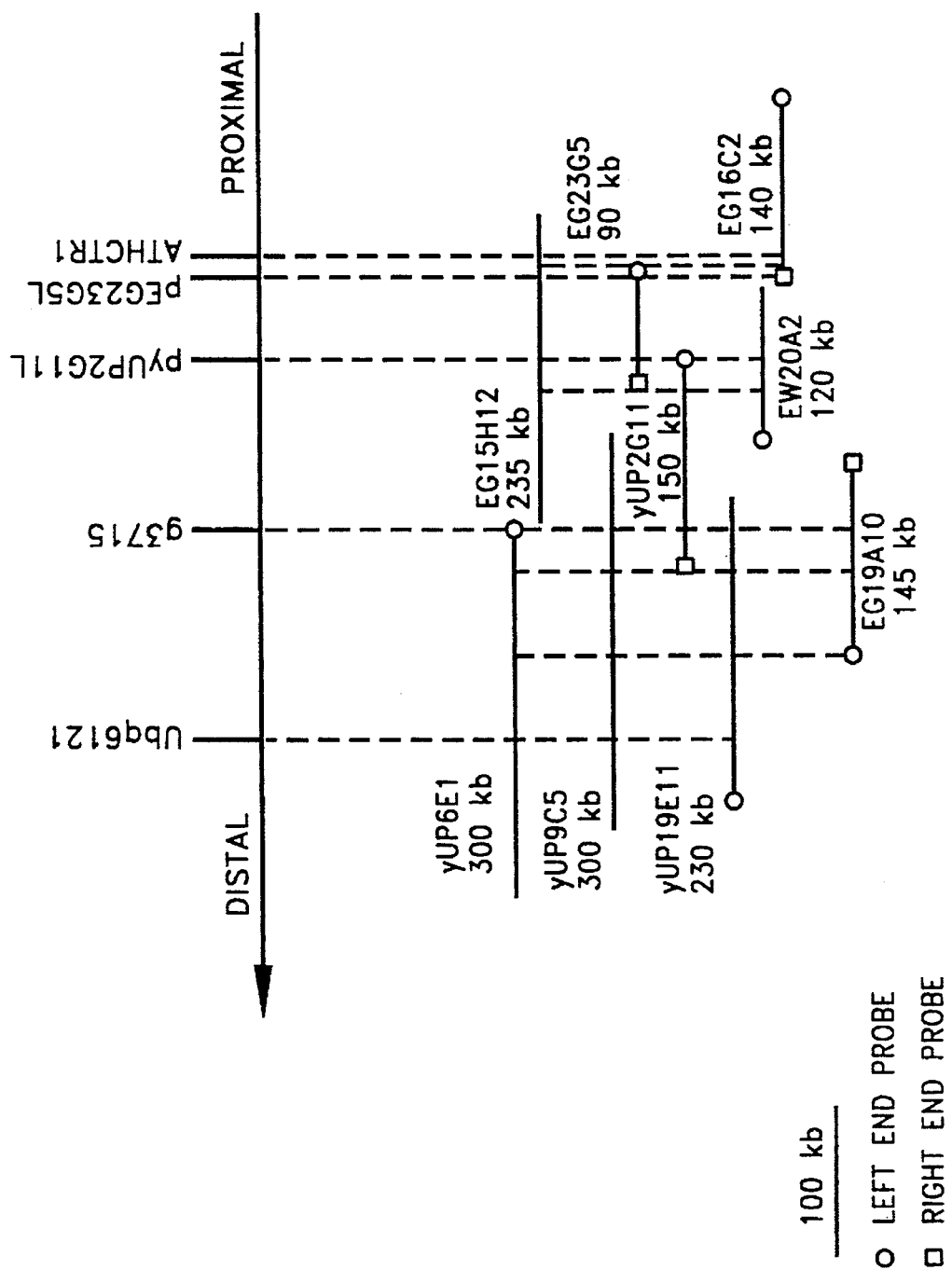
FIG. 1 displays the EIN2 region on chromosome 5 of *Arabidopsis thaliana*. O represents the left end probe, □ represents the right end probe, a length of 100 kb is represented in the legend.

The present invention is directed to nucleic acid and amino acid sequences which lend valuable characteristics to plants.

The present invention is directed to nucleic acid sequences of the EIN2 locus. Wild type and mutant sequences of EIN2 are within the scope of the present invention. Amino acid and protein sequences corresponding to the nucleic acid sequences are included in the present invention. EIN2 mutations provide for ethylene insensitivity and pathogen tolerance in plants.

SEQUENCE ID NO: 2, the isolated cDNA representing the nucleic acid sequence coding for EIN2 and the isolated genomic EIN2 sequence of SEQUENCE ID NO: 1 are embodiments of the present invention. The purified amino acid sequence of SEQUENCE ID NO: 3 represents the EIN2 protein product encoded by the cDNA identified above. The EIN2 mutations identified herein by nucleotide position are measured in accordance with the beginning of the cDNA.

An ein2-3 mutation was created by X-ray mutagenesis which resulted in a thymidine insertion at nucleotide position 3642 of the cDNA sequence in SEQUENCE ID NO: 2. A frameshift results in the corresponding amino acid sequence.

An ein2-4 mutation was also generated by X-ray mutagenesis. The ein2-4 mutation has an "AG" to "TTT" mutation at position 2103 of the EIN2 cDNA sequence resulting in a frameshift in the corresponding amino acid sequence.

An ein2-5 mutation was generated by X-ray mutagenesis, such that a deletion beginning at nucleic acid position 1570 of the cDNA occurred. Nucleic acids CATGACT were deleted. A frameshift results in the corresponding protein product.

An ein2-6 mutation has a deletion of nucleic acids GAGTTGCGCATG, SEQ ID NO: 17, beginning at nucleic acid position 965 of the cDNA sequence. The ein2-6 mutation was generated by Agrobacterium mutagenesis. This mutation results in a deletion at the amino acid level of Gly-Val-Ala-His, SEQ ID NO: 18, formerly beginning at amino acid position 115.

Another mutation, ein2-9 was generated by DEB mutagenesis and has an "A" to "C" transition at position 4048 that results in a "His" to "Pro" change at amino acid position 1143 in the corresponding protein.

ein2-11 was generated by DEB mutagenesis and has a "TG" to "AT" transition at nucleic acid position 3492. This results in an Ochre stop signal at amino acid position 957 in the protein.

An ein2-12 mutation was obtained by X-ray mutagenesis resulting in a deletion at nucleic acid position 1611 of nucleic acids TGCTACAATCAGAATTCTTGCAGT, SEQ ID NO: 19. The corresponding amino acid sequence reveals a deletion of amino acids Ala-Thr-Ile-Arg-Ile-Leu-Ala-Val, SEQ ID NO: 20, beginning at amino acid position 331.

An ein2-16 mutation results in an "AGT" to "G" transition at nucleic acid position 2851 as a result of X-ray mutagenesis. A frameshift results in the corresponding protein.

Table 4 sets forth the EIN2 alleles and the results of the mutagenesis.

Ein3 sequences for genes and proteins are the subject of the present invention. The present invention is directed to wild type nucleic acid and amino acid sequences as well as mutations of these sequences. EIN3 mutations result in ethylene insensitive plants. Ein-like genes and protein sequences, including eil1, eil2, and eil3 sequences, are similar to ein3 sequences, and are also disclosed in the present invention. The EIN3 mutations are identified below by nucleotide position number in accordance with the beginning of the genomic DNA sequence.

The DNA sequences coding for ein3 are set forth in SEQ ID NOS: 5 (genomic) and 4 (cDNA). The amino acid sequence may be found in SEQ ID NO: 6.

In ein3-1, a "G" to "A" conversion in the genomic DNA at nucleotide 1598 occurs as a result of EMS mutagenesis. In the corresponding protein, "W" is changed to a stop codon at amino acid position 215. The ein3-2 mutation was generated by T-DNA insertion mutagenesis. The T-DNA inserted after nucleotide 2001 of the genomic, interrupting the protein after amino acid 349. The ein3-3 mutation results in a "G" to "T" switch at nucleotide position 1688 of genomic DNA as a result of DEB mutagenesis. The amino acid sequence results in a conversion of "K" to "N" at amino acid position 245.

The cDNAs of eil1, eil2, and eil3, are set forth in SEQ ID NOS: 7, 9, and 11, respectively. The corresponding amino acid sequences for the ein-like genes are set forth in SEQ ID NOS: 8, 10, and 12, (eil1, eil2, and eil3, respectively). A consensus sequence representing the common codons of the three ein-lie genes is SEQ ID NO: 13.

Table 6 sets forth the EIN3 alleles and the results of the mutagenesis. The translation start site of EIN3 is at nucleotide position 954 of the genomic sequence. The translation start sites for EIL1, EIL2, and EIL3 are at nucleotide positions 251, 8, and 102 of the respective cDNA sequences.

The present invention is directed to wild type and mutant sequences for the Hls1 locus. The hls gene is regulated by ethylene directly. Amino acid and protein sequences corresponding to the wild type and mutant gene for Hls1 are within the scope of the present invention.

The present invention is directed to nucleic acid sequences of the HLS1 locus. Wild type and mutant sequences of HLS1 are within the scope of the present invention. Amino acid and protein sequences corresponding to the nucleic acid sequences are included in the present invention. The HLS1 mutations are identified below by nucleotide position number in accordance with the beginning of the genomic DNA sequence.

SEQUENCE ID NO: 14, the isolated cDNA representing the nucleic acid sequence coding for HLS1, and the isolated genomic HLS1 sequence of SEQUENCE ID NO: 15 are embodiments of the present invention. The purified amino acid sequence of SEQUENCE ID NO: 16 represents the HLS1 protein product encoded by the cDNA identified above.

An hls1-1 mutation was created by EMS mutagenesis which resulted in a "G" to "A" transition at nucleotide position 3487 of the genomic DNA sequence. This frameshift results in the corresponding amino acid sequence having a "Glu" to "Lys" substitution at amino acid position 345.

An hls1-5 mutation of was generated by DEB mutagenesis. The hls1-5 mutation has an "T" to "A" mutation at position 2194 of the HLS1 genomic DNA sequence, resulting in a mutation in the splice donor site. An hls1-7 mutation was also created by DEB and resulted in a "T" to "A" transition at nucleic acid position 2194. The result in the amino acid sequence is also a mutation in the splice donor site. Mutations at splice donor sites often result in aberrant splicing causing a frameshift or insertion to occur. The exact nature of the change in hls1-5 and hls1-7 may be determined by analyzing the protein from those mutants using an antibody.

hls1-6 is a mutation created by EMS resulting in a "T" to "G" transition at nucleic acid position 3431. The corresponding amino acid sequence has a "Lys" to "Trp" substitution at amino acid position 2326.

The mutation hls1-4 was created by DEB mutagenesis resulting in a "G" to "A" transition at nucleic acid position 3487. The corresponding amino acid sequence has a "Glu" to "Lys" change at amino acid position 345.

hls1-9 is created by EMS mutagenesis. The sequence results in "C" to "T" at nucleic acid position 2060, which corresponds to an "Arg" to "TGA" creating a "stop signal" at amino acid position 11.

hls1-8 is a mutation resulting from EMS mutagenesis. The nucleic acid sequence has a "C" to "T" change at position 2992. The mutation results in an amino acid sequence having an "Arg" to "Stop" transition at amino acid position 180.

An EMS mutation resulting in a "G" to "A" change at nucleic acid position 2033 is represented by hls1-10. The amino acid sequence corresponding to the mutation reveals a "Met" (Start signal) to "Ile" transition at amino acid position 1.

Table 7 sets forth the HLS1 alleles and the results of the mutagenesis.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQUENCE ID NUMBERS set forth herein, and alterations in the nucleic acid sequences including alterations, deletions, mutations and homologs. In addition, mismatches within the sequences identified above, which achieve the methods of the invention, are also considered within the scope of the disclosure. The sequences may also be unmodified or modified.

Also amino acid, peptide and protein sequences within the scope of the present invention include, and are not limited to, the sequences set forth herein and alterations in the amino acid sequences including alterations, deletions, mutations and homologs.

In accordance with the invention, the nucleic acid sequences employed in the invention may be exogenous/ heterologous sequences. Exogenous and heterologous, as used herein, denotes a nucleic acid sequence which is not obtained from and would not normally form a part of the genetic make-up of the plant or the cell to be transformed, in its untransformed state. Plants comprising exogenous nucleic acid sequences of ein2, ein3, eil1, eil2, eil3, or hls1 mutations, such as and not limited to the nucleic acid sequences of SEQUENCE ID NUMBERS set forth herein are within the scope of the invention.

Transfected and/or transformed plant cells comprising nucleic acid sequences of ein2, ein3, eil1, eil2, eil3, or hls1 mutations, such as and not limited to the nucleic acid sequences of SEQUENCE ID NUMBERS set forth herein, are within the scope of the invention. Transfected cells of the invention may be prepared by employing standard transfection techniques and procedures as set forth in Sambrook et al., *Molecular Cloning: A Laboratory Manual*, 2nd ed., 1989, Cold Spring Harbor Laboratory Press, Cold Spring Harbor, N.Y., hereby incorporated by reference in its entirety.

In accordance with the present invention, mutant plants which may be created with the sequences of the claimed invention include higher and lower plants in the Plant Kingdom. Mature plants and seedlings are included in the scope of the invention. A mature plant includes a plant at any stage in development beyond the seedling. A seedling is a very young, immature plant in the early stages of development.

Particularly preferred plants are those from: the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *satira* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

Ein2 mutant sequences render plants disease and pathogen tolerant, and ethylene insensitive. For purposes of the current invention, disease tolerance is the ability of a plant to survive infection with minimal injury or reduction in the harvested yield of saleable material. Plants with disease tolerance may have extensive levels of infection but have little necrosis and few to no lesions. These plants may also have reduced necrotic and water soaking responses and chlorophyll loss may be virtually absent. In contrast, resistant plants generally limit the growth of pathogens and contain the infection to a localized area with multiple apparent injurious lesions.

The current invention is directed to, for example, identifying plant tolerance to bacterial infections including, but not limited to *Clavibacter michiganense* (formerly *Coynebacterium michiganense*), *Pseudomonas solanacearum* and *Erwinia stewartii*, and more particularly, *Xanthomonas campestris* (specifically pathovars *campestris* and *vesicatoria*), *Pseudomonas syringae* (specifically pathovars tomato, *maculicola*).

In addition to bacterial infections, disease tolerance to infection by other plant pathogens is within the scope of the invention. Examples of viral and fungal pathogens include, but are not limited to tobacco mosaic virus, cauliflower mosaic virus, turnip crinkle virus, turnip yellow mosaic virus; fungi including *Phytophthora infestans, Peronospora parasitica, Rhizoctonia solani, Botrytis cinerea, Phoma lingam* (*Leptosphaeria maculans*), and *Albugo candida*.

Like ein2, ein3 mutants also exhibit ethylene insensitivity. However, ein3 mutants do not exhibit disease or pathogen tolerance. Ethylene, $CH_2=CH_2$, is a naturally occurring plant hormone. The ethylene regulatory pathway includes the ethylene biosynthesis pathway and the ethylene autoregulatory or feedback pathway, see FIG. 6. In the ethylene biosynthesis pathway, methionine is converted to ethylene with S-adenosylmethionine (SAM) and 1-aminocyclopropane-1-carboxylic acid (ACC) as intermediates. These two reactions are catalyzed by ACC synthase and ethylene-forming enzyme (EFE), respectively. Little is known about the enzymes catalyzing these reactions and their regulation at the molecular level.

Figure 6:
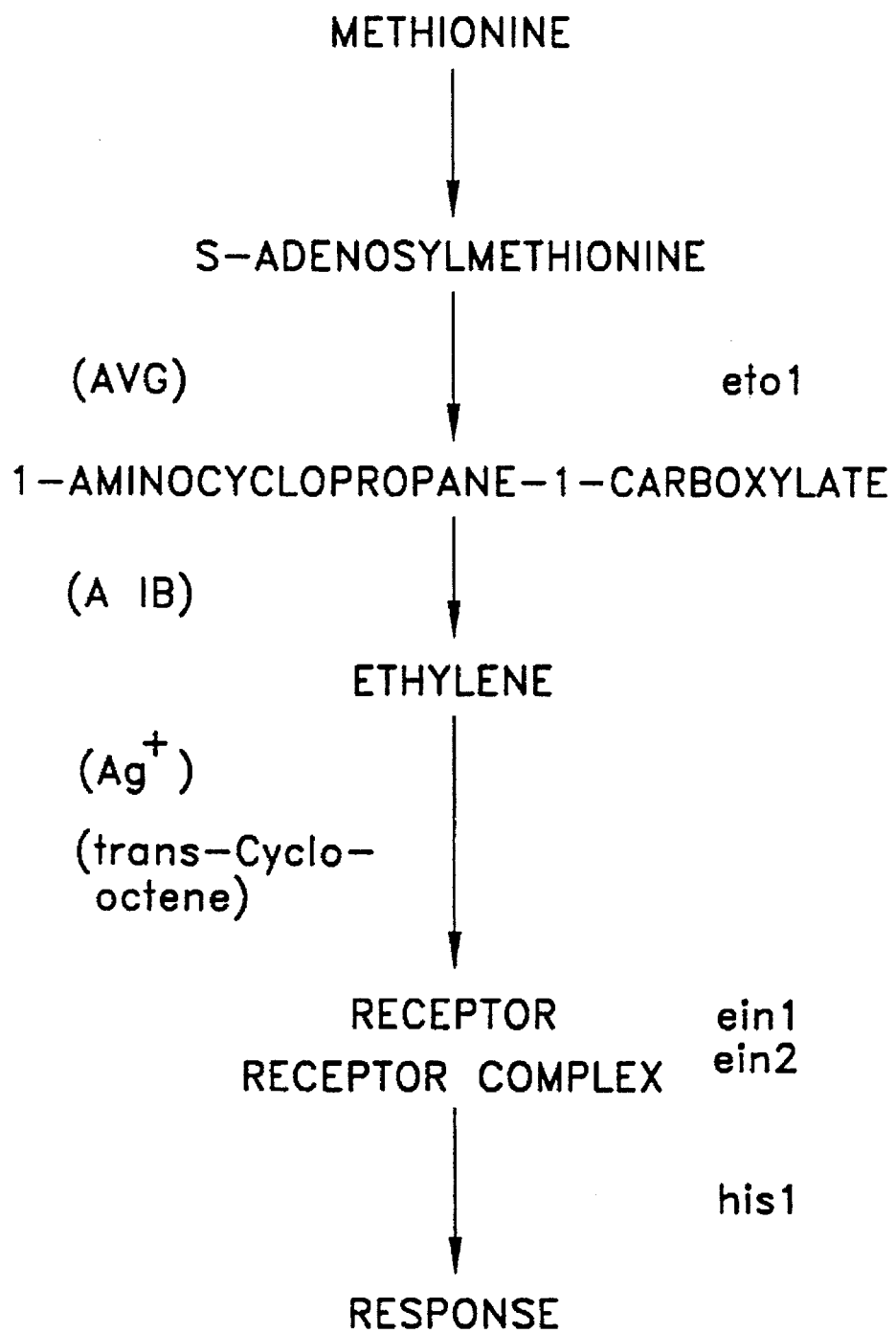
FIG. 6 is a schematic illustration of the ethylene biosynthesis pathway.

The receptor and receptor complex of FIG. 6 are believed to function with the autoregulatory pathway in the control of ethylene production. Ethylene regulatory pathway inhibitors are positioned along the left side of FIG. 6. The inhibitors include AVG (aminoethoxyvinylglycine) and AIB ($\alpha$-aminoisobutyric acid). The steps at which the mutants, ethylene overproducer (eto1), ethylene insensitive (ein1, ein2) and hookless (hls1), are defective appear on the right of FIG. 6.

In accordance with the claimed invention, ethylene insensitive plants are those which are unable to display a typical ethylene response when treated with high concentrations of ethylene. For purposes of the present invention, ethylene insensitivity includes total or partial inability to display a typical ethylene response. A typical ethylene response in wild type plants includes, for example, the so-called "triple response" which involves inhibition of root and stem elongation, radial swelling of the stem, and absence of normal geotropic response (diageotropism). Thus, for example, ethylene insensitive plants may be created in accordance with the present invention by the presence of an altered "triple response" wherein the root and stem are elongated despite the presence of high concentrations of ethylene. Further, a typical ethylene response also includes a shut down or diminution of endogenous ethylene production, upon application of high concentrations of ethylene. Ethylene insensitive plants may thus also be screened for, in accordance with the present invention, by the ability to continue production of ethylene, despite administration of high concentrations of ethylene. Such ethylene insensitive plants are believed to have impaired receptor function such that ethylene is constitutively produced despite the presence of an abundance of exogenous ethylene.

Figure 7A:
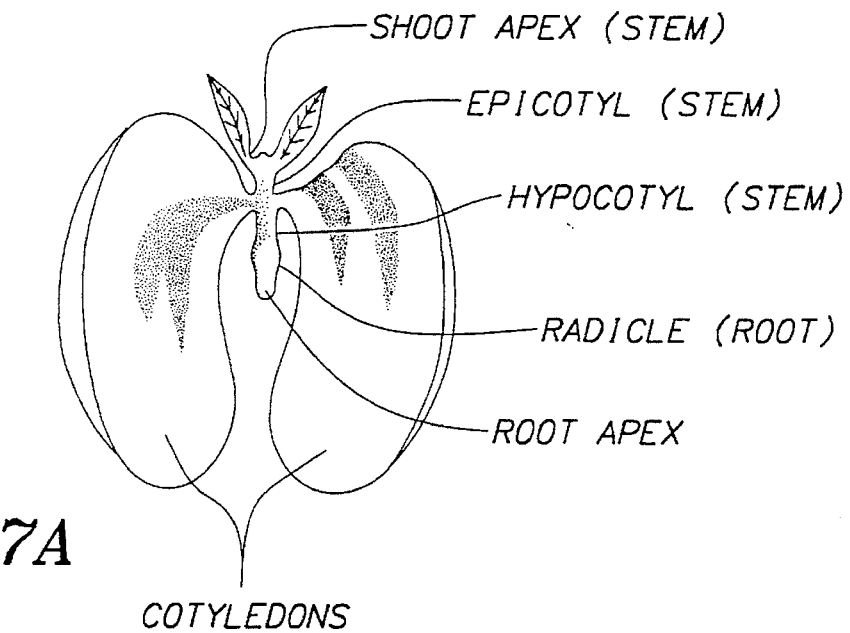
FIG. 7A and 7B depict a seedling body and developing plant. Specifically.
Figure 7B:
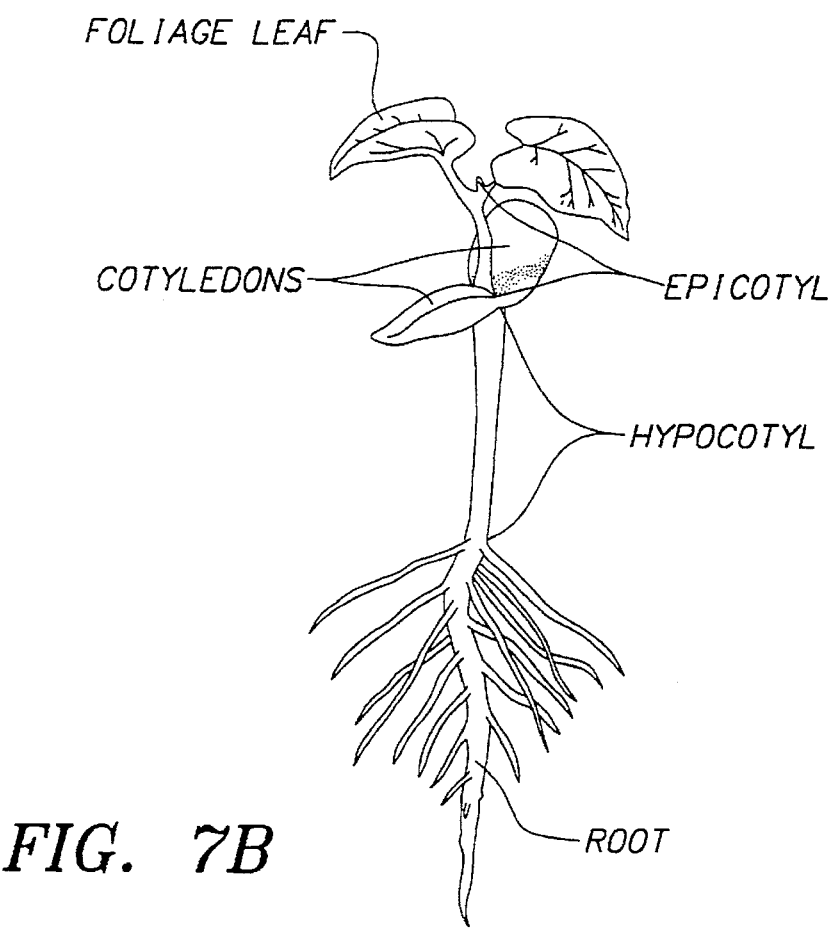
Figure 10:
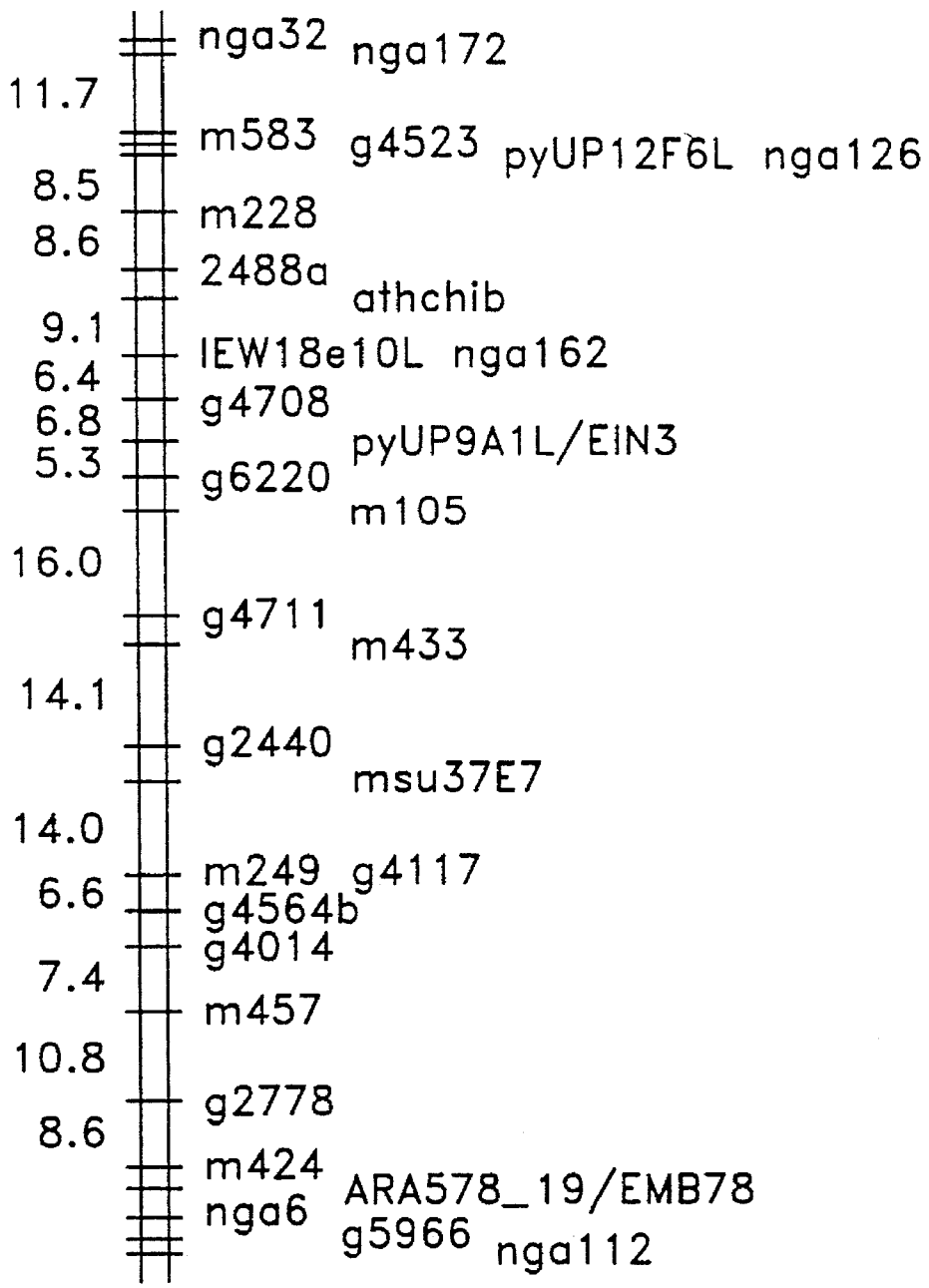
FIG. 10 exhibits a map of chromosome 3 and the position of EIN3 relative to other gene loci.
Figure 11:
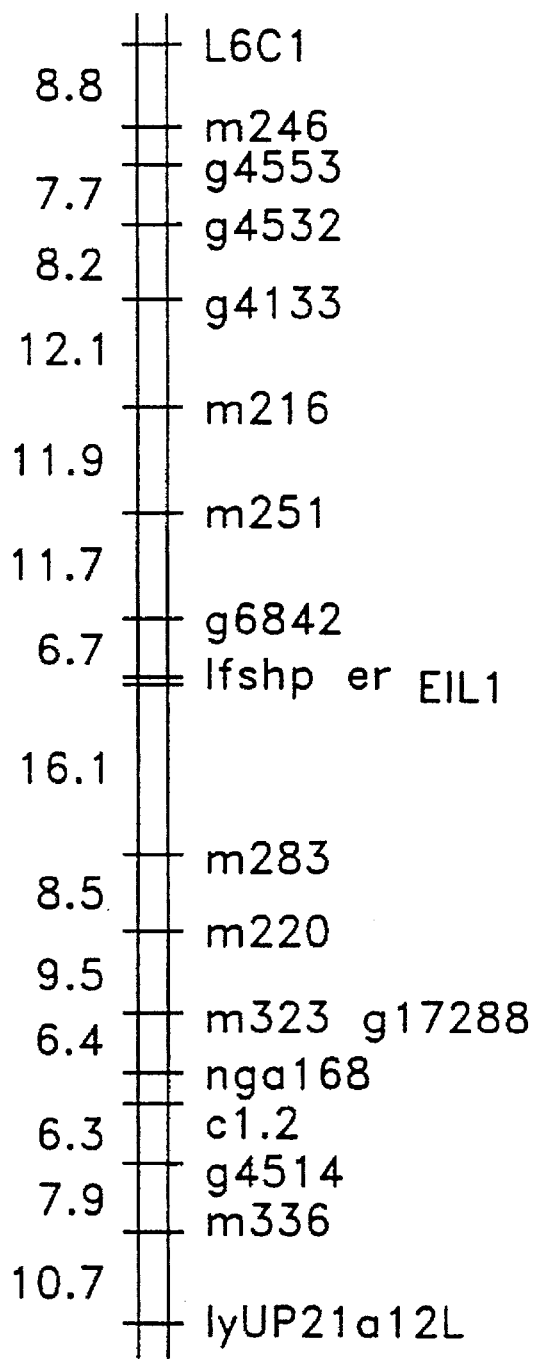
FIG. 11 sets forth a map of chromosome 2 and the position of EIL1 relative to other gene loci.
Figure 12:
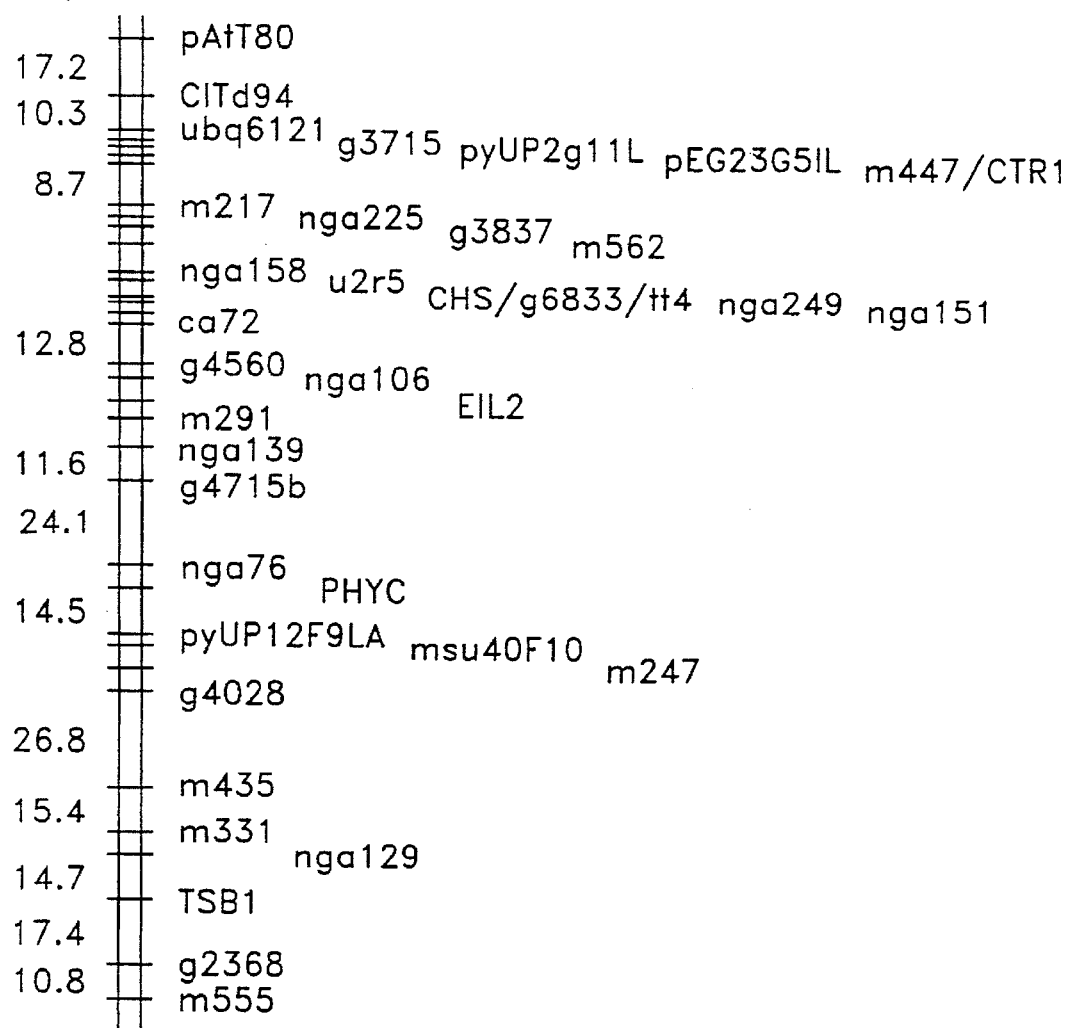
FIG. 12 displays a map of chromosome 5 and the position of EIL2 relative to other gene loci.
Figure 13:
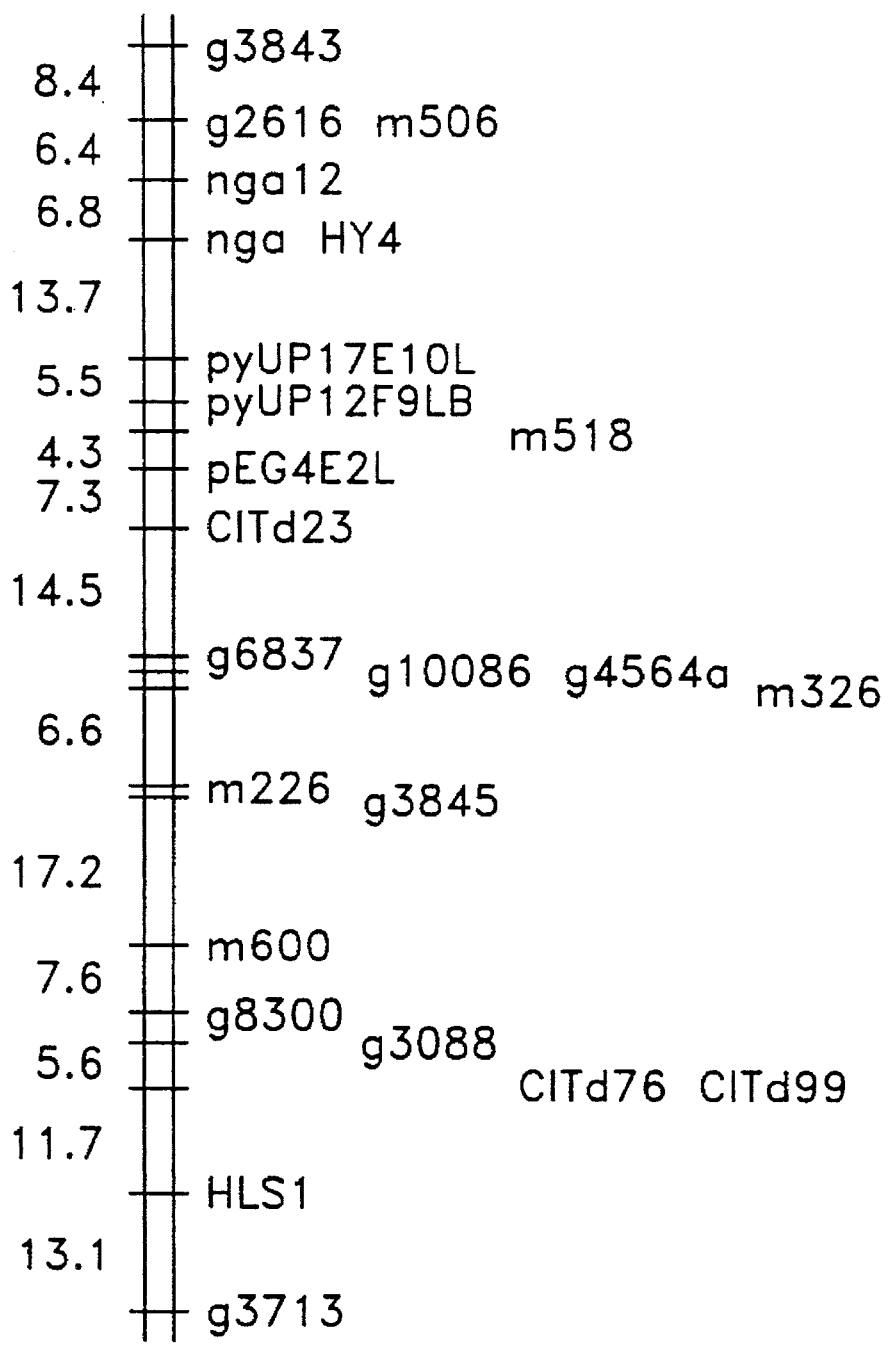
FIG. 13 exhibits a map of chromosome 4 and the position of HLS1 relative to other gene loci.
Figure 14:
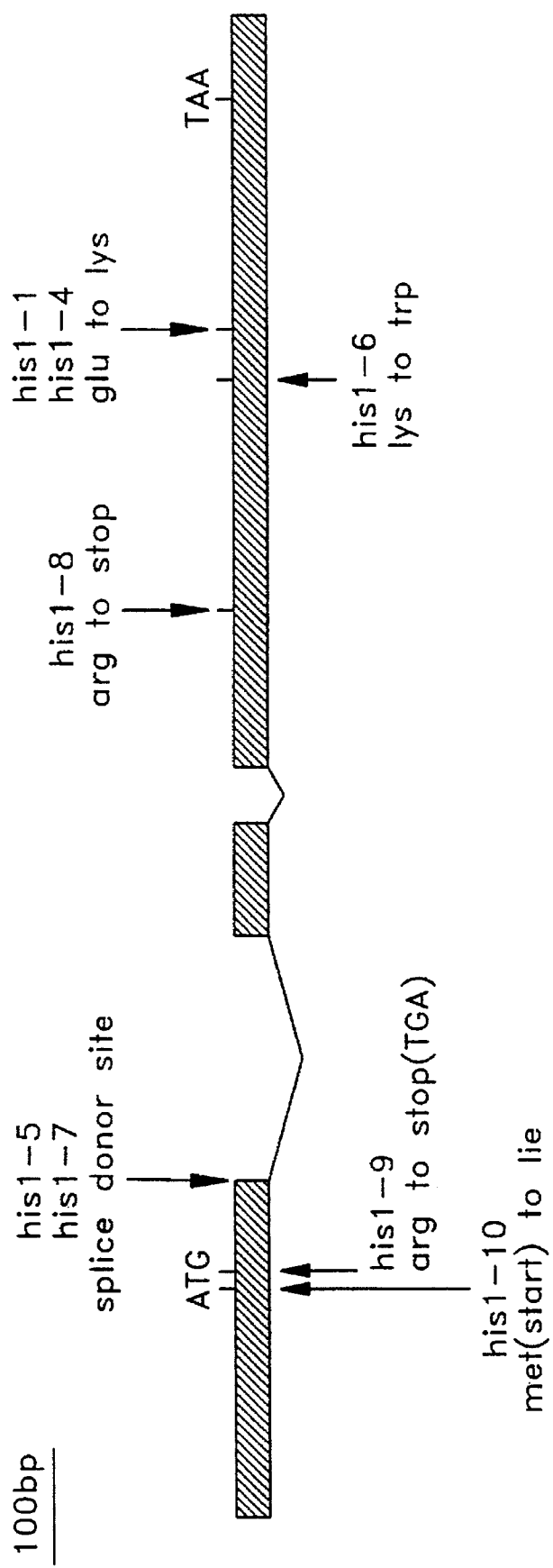
FIG. 14 is a representation of the arrangement of hls mutants on chromosome 4.
Figure 16:
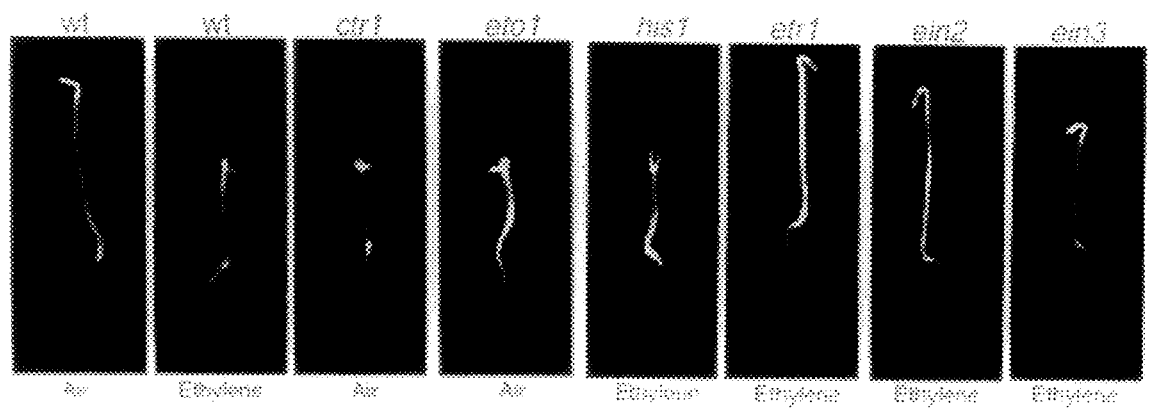
FIG. 16 displays ethylene responses in wild type and mutant: ctr1, eto1, hls1, etr1, ein2, ein3, Arabidopsis seedlings. Seeds of the indicated genotype were germinated and grown for three days in the dark in either air or air containing 10 ppm ethylene.
Figure 17:
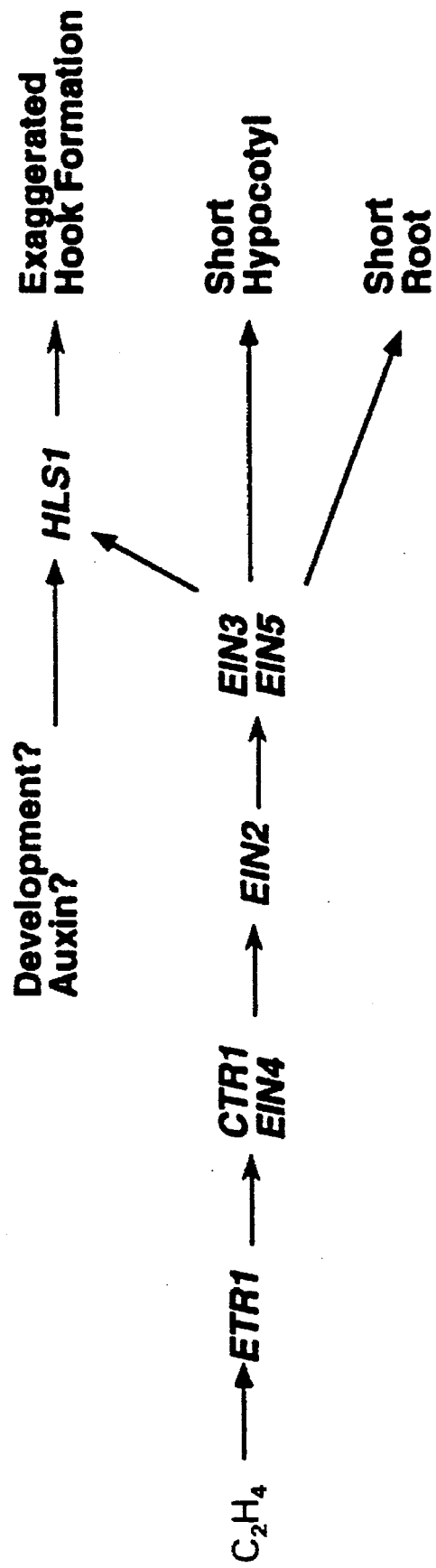
FIG. 17 is a genetic model of interactions among components of the ethylene signal transduction pathway. This model shows the predicted order in which the various gene products act which is based on the epistatic relationships among the mutants. The seedling ethylene responses are indicated on the right.

Screening includes screening for root or stem elongation and screening for increased ethylene production. Ethylene sensitive wild type plants experience an inhibition of root and stem elongation when an inhibitory amount of ethylene is administered. By inhibition of root and stem elongation, it is meant that the roots and stems grow less than the normal state (that is, growth without application of an inhibitory amount of ethylene). Typically, normal Arabidopsis (Col) grown without ethylene or ethylene precursor aminocyclopropane, ACC, root elongation is about $6.5\pm0.2$ mm/3 days; normal stem elongation is $8.7\pm0.3$ mm/3 days. Ein 2-1 plants grown without ethylene or ACC have root elongation of about $7.5\pm0.2$ mm/3 days and stem elongation of $11.35\pm0.3$ mm/3 days. In the presence of 100 µm ACC, Col root growth is $1.5\pm0.04$ mm/3 days; ein 2-1 is $4.11\pm0.1$ mm/3 days and stem growth of $3.2\pm0.1$ mm/3 days for Col and $8.0\pm0.2$ mm/3 days for ein 2-1. Alternatively, plants may be sprayed with ethaphon or ethrel. By roots, els used here, it is meant mature roots (that is, roots of any plant beyond the rudimentary root of the seedling), as well as roots and root radicles of seedlings. Stems include hypocotyls of immature plants of seedlings and stens, and plant axes of mature plants (that is, any stem beyond the hypocotyl of seedlings). See FIG. 7A and FIG. 7B.

Ethylene sensitive wild type plants experience a shut down or diminution of endogenous ethylene production, upon application of high concentrations of ethylene. In the ethylene insensitive plants of the present invention, the plants continue endogenous production of ethylene, despite administration of inhibitory amounts of ethylene. Ethylene production for wild type and ethylene insensitive mutants are shown in Table 1. An ethylene insensitive plant will produce an amount or have a rate of ethylene production greater than that of a wield type plant upon administration of an inhibitory amount of ethylene. As one skilled in the art will recognize, absolute levels of ethylene produced will change with growth conditions.

Ein1 and ein2 mutants are described for example in, Guzman et al., "Exploiting the Triple Response of Arabidopsis to Identify Ethylene-Related Mutants", *The Plant Cell* 1990, 2, 513, the disclosures of which are hereby incorporated herein by reference, in their entirety.

The present invention is further described in the following examples. These examples are not to be construed as limiting the scope of the appended claims.

EXAMPLE 1

PRODUCTION OF Arabidopsis MUTANTS

The production of plants which exhibit enhanced disease tolerance and ethylene insensitivity were investigated with the use of Arabidopsis mutants ein, which are insensitive to ethylene and are derived from Arabidopsis Col-0. The ein mutants were prepared according to the method of Guzman et al., *The Plant Cell*, 1990, 2, 513, the disclosures of which are hereby incorporated herein by reference, in their entirety. Specifically, twenty five independent ethylene-insensitive mutants were isolated; six mutants which showed at least three-fold difference in the length of the hypocotyl compared with ethylene-treated wild-type hypocotyl, were further characterized. In these mutants, the apical hook was either present, absent or showed some curvature in the apical region. The appearance of the apical curvature was dependent on the duration of the incubation. After more than 3 days of incubation in the dark with 10 μl/L ethylene, the apical curvature was absent. This phenotype was named "ein" for ethylene insensitive.

Mendelian analysis indicated that insensitivity to ethylene was inherited as either a dominant or recessive trait depending on the mutation studied. Complementation analysis was performed with five recessive mutants to determine whether more than one locus was involved in this phenotype. The results of these studies indicated that all five recessive mutations were allelic. The ein phenotype was tested for linkage to nine visible markers to determine whether the recessive and dominant ein mutations were allelic. The dominant ein mutation was mapped close to the mutation ap-1 locus on chromosome 1 and was named ein1-1. None of the nine markers showed linkage to the recessive ein mutation. Restriction fragment length polymorphism (RFLP) analysis was performed to map this mutation. Randomly selected RFLP probes were initially used to assess linkage. After testing probes from three different chromosomes, linkage was detected to one RFLP from chromosome 4 and named ein2-1. This observation was confirmed using additional RFLP probes from the same chromosome. Further experimentation confirmed ein2-2, ein2-3, ein2-4 and ein2-5 to be alleles of ein2-1.

Growth features of ethylene insensitive mutants were also observed. After seedlings were planted in soil and cold treated at 4° C. for 4 days, the seedlings were incubated in the dark at 23° C. for 66–72 hours. Plants were grown to maturity in a growth chamber at 22° C. to 25° C. under continuous illumination with fluorescent and incandescent light. The rosette of ein1-1 and ein2-1 plants was larger compared with the wild type, Col-0, rosette and a delay in bolting (1 cm to 2 cm growth in the length of the stem) was observed. These observations indicated that the ethylene insensitive mutations identified at the seedling stage exerted remarkable effects during adult stages of growth.

eto mutants, which constitutively produce ethylene, were initially screened by observing a constitutive triple response; seedlings with inhibition of hypocotyl and root elongation, swelling of the hypocotyl and exaggerated tightening of the apical hook. Mendelian segregation analysis determined the genetic basis of these mutations to be a single recessive mutation and identified as an ethylene overproducer or eto.

eto1, ein1 and ein2 mutants were analyzed to determine ethylene accumulation. The mutants were backcrossed to the wild type before physiological examination. Surface-sterilized seeds (about 500) were germinated and grown for 66 to 72 hours in the dark at 23° C. in 20 ml gas chromatograph vials containing 15 ml of growth medium.

To measure the conversion, Df exogenous 1-aminocyclopropane-1-carboxylic acid (ACC, an intermediate in ethylene production) to ethylene, seedlings were grown in 1% low-melting-point agarose buffered with 3 mM Mes at pH 5.8. In this solid support no chemical formation of ethylene from ACC was detected at any of the concentrations of ACC employed.

Ethylene accumulation from tissues of mature plants (100 mg) was measured after overnight incubation in 20 ml gas chromatograph vials. Leaves and inflorescence were taken from 24–28 day old plants, siliques from 32–36 day old plants. Accumulation of ethylene was determined by gas chromatography using a photo-ionization detector (HNU) and a Hewlett Packard HP5890A gas chromatograph equipped with an automated headspace sampler. A certified standard of 10 μl/L ethylene (Airco) was used to calculate ethylene concentrations. The concentration of the inhibitors of ethylene biosynthesis and ethylene action was determined empirically. For eto mutants, AVG, α-aminoisobutyric acid, and AgNO$_3$ supplemented the media at 5μM, 2mM and 0.1 mM, respectively and trans-cyclooctene (17 μl/L) was injected into the vial after the cold treatment. Ethylene production was increased significantly in the dominant ein1-1 mutant and the recessive ein2-1 mutant, see Table 1. Ethylene production was inhibited in eto1-1 seedlings that were grown in media supplemented with ethylene inhibitors aminoethoxyvinylglycine, AGV and α-aminoisobutyric acid, AIB, see Table 1.

The EIL sequences represent cDNA sequences similar to the EIN3 sequence. They were obtained by screening an Arabidopsis seedling cDNA library (Kieber et al., *Cell*, 1993, 72, 427–441, at low stringency in the following manner. The cDNA library was hybridized with the radiolabeled EIN3 cDNA insert at 42° C. for 48 hours in a hybridization solution consisting of 30% formamide, 5× Denhardt's solution, 0.5% SDS, 5× SSPE, 0.1 mg/ml sheared salmon sperm DNA, according to the methods of Feinberg and Vogelstein, *Anal. Biochem.* 1984, 177, 266–267, incorporated herein by reference in its entirety. The filters were washed at 42° C. with 30% formamide, 0.5% SDS, 5× SSPE; followed by 2× SSPE.

Mutageneized HLS1 plants were obtained as set forth above for EIN2, EIN3, and EIL.

TABLE 1

| Ethylene Production in Triple Response Mutants | |
|---|---|
| Strain | Ethylene Accumulation |
| Wild Type | |
| Etiolated Seedlings | 6.7 ± 0.68 nL |
| Light-grown Seedlings | 84.25 ± 13.95 nL |
| Leaves | 73.01 ± 17.64 nL/g |
| Siliques | 144.96 ± 28.99 nL/g |
| Inflorescence | 234.53 ± 18.04 nL/g |
| eto1-1 | |
| Etiolated Seedlings | 276.72 ± 53.70 nL |
| Light-Grown Seedlings | 182.01 ± 24.84 nL |
| Leaves | 174.39 ± 29.18 nL/g |
| Siliques | 322.16 ± 38.66 nL/g |
| Inflorescence | 1061.84 ± 72.16 nL/g |
| hls1-1 | |
| Etiolated seedlings | 5.81 ± 0.32 nL |
| Leaves | 31.56 ± 0.32 nL |
| ein1-1 | |
| Etiolated Seedlings | 12.73 ± 2.79 nL |
| Leaves | 222.95 ± 2.79 nL |
| ein2-1 | |
| Etiolated Seedlings | 20.69 ± 2.09 nL |
| Leaves | 135.59 ± 26.89 nL/g |

Another ethylene insensitive mutant of *Arabidopsis thaliana* was designated etr by Bleecker et al. in "Insensitivity to Ethylene Conferred by a Dominant Mutation in *Arabidopsis thaliana*", *Science* 1990, 241, 1086, the disclosures of which are hereby incorporated herein by reference, in their entirety. Etr was identified by the ethylene-mediated inhibition of hypocotyl elongation in dark-grown seedlings. Populations of M$_2$ generation from mutagenized seed of *Arabidopsis thaliana* were plated on a minimal medium solidified with 1% agar and placed in a chamber through which 5 μl/L ethylene in air was circulated. Seedlings that had grown more than 1 cm after days were selected as potential ethylene insensitive mutants. A screen of 75,000 seedlings yielded three mutant lines that showed heritable insensitivity to ethylene. Hypocotyl elongation of etr mutant line was unaffected by ethylene at concentrations of up to 100 μl/L, while elongation of the wild type was inhibited by 70% with ethylene at 1 μl/L.

EXAMPLE 2

CLONING AND SEQUENCING OF EIN2

The EIN2 locus was identified by a mapped based cloning strategy described as follows. The ein2-1 mutant was crossed onto the DP28 marker line (dis1, clv2, er, tt5) according to the methods of Koornneef and Stamm, *Methods in Arabidopsis Research*, eds. C. Koncz, N-H Chua, and J. Schell, 1992, World Scientific Publishing Co., Singapore, incorporated herein by reference in its entirety. The F2 progeny were mapped with Restriction Fragment Length Polymorphisms (RFLPs) according to the methods of Chang et al., *Proc. Natl Acad. Sci. USA* 1988, 85, 6856 and Nam et al., *Plant Cell* 1990, 1, 699, the disclosures of which are hereby incorporated by reference in their entirety.

The ein2-1 mutation was found to segregate with RFLPs on the top of chromosome five (Table 2). Two recombinant progeny found with λ217 (E15 and E54) were also recombinant with the more proximal g3837 and λ291 clones, indicating that ein2-1 is distal to λ217. Recombinant plants were identified by examining $F_3$ families from the ein2-1× DP28 cross for the genotype at the λ217 locus. Protocols are the same mapping with RFLPs. Recombinants were defined by having at least one recombinant chromosome in an ein2-1 homozygote. The Ubq6121 marker, however, identified a different F2 progeny (E46) as being recombinant. This positions ein2 within the interval of λ217 and Ubq6121. To further limit the position of ein2 on the top of chromosome 5, recombinants were sought with the PCR based marker ATHCTR1, Bell et al., *Methods in Plant Molecular Biology: A Laboratory Manual*, 1993, eds. Maliga, Klessig, and Cashmore, Cold Spring Harbor Laboratory Press, the disclosure of which is hereby incorporated by reference in its entirety.

A single recombinant progeny was identified in 102 F2 progeny scored. This F2 progeny was also recombinant at the proximal λ217 and ASA1 markers, demonstrating the position of ein2 as distal to ATHCTR1. Additional genetic information was generated by examining recombinant progeny from a cross between ein2-1 and hy5. Two additional recombination events between ein2-1 and ATHCTR1 were identified by this approach. There were no recombinant plants identified at the g3715 locus, a cosmid clone identified in Nam et al., supra.

TABLE 2

Characterization of Plants Having ein2 Mutation

| ALLELE | HYPOCOTYL | SE | ROOT | SE | TL | SE |
|---|---|---|---|---|---|---|
| Columbia | 3.6 | 0.2 | 1.6 | 0.1 | 5.2 | 0.2 |
| Landsberg | 3.2 | 0.1 | 1.7 | 0.1 | 4.9 | 0.2 |
| Wassilewskija | 2.7 | 0.1 | 0.9 | 0.1 | 3.6 | 0.1 |
| ein2-1 * | 6.0 | 0.3 | 7.1 | 0.1 | 13.1 | 0.4 |
| ein2-3 * | 8.2 | 0.2 | 5.9 | 0.3 | 14.1 | 0.4 |
| ein2-4 * | 7.5 | 0.2 | 6.3 | 0.4 | 13.8 | 0.5 |
| ein2-5 * | 8.4 | 0.2 | 7.2 | 0.5 | 15.6 | 0.5 |
| ein2-6 | 8.8 | 0.4 | 5.4 | 0.2 | 14.2 | 0.5 |
| ein2-7 | 5.9 | 0.1 | 3.8 | 0.1 | 9.7 | 0.2 |
| ein2-9 | 7.3 | 0.2 | 5.5 | 0.2 | 12.8 | 0.3 |
| ein2-10 | 6.4 | 0.1 | 4.7 | 0.4 | 11.1 | 0.5 |
| ein2-11 | 8.1 | 0.1 | 7.7 | 0.3 | 15.8 | 0.4 |
| ein2-12 | 6.5 | 0.3 | 4.4 | 0.3 | 10.9 | 0.4 |
| ein2-13 | 5.4 | 0.2 | 3.7 | 0.2 | 9.1 | 0.4 |
| ein2-15 | 6.9 | 0.5 | 5.3 | 0.4 | 12.2 | 0.9 |
| ein2-16 | 8.1 | 0.3 | 7.7 | 0.6 | 15.8 | 0.7 |
| ein2-18 + | 6.2 | 0.2 | 6.5 | 0.4 | 12.7 | 0.4 |
| ein2-19 + | 7.1 | 0.2 | 6.2 | 0.5 | 13.3 | 0.6 |
| ein2-20 + | 5.8 | 0.2 | 5.2 | 0.2 | 11.0 | 0.3 |

All units are in mm, TL = Total Length, SE = Standard Error
* Guzman and Ecker, Plant Cell 1990, 2, 513.
+ Gift of Caren Chang and Elliot Meyerowitz, Pasadena, CA.

The flanking genetic markers were used to build a Yeast Artificial Chromosome (YAC) physical contig spanning the ein2 locus (FIG. 1). The YAC positions were identified by colony hybridization pursuant to the technique of Matallana, et al., *Methods in Arabidopsis Research*, eds C. Koncz, N-H Chua, and J. Schell, 1992, World Scientific Publishing Co., Singapore, the disclosures of which are hereby incorporated by reference in their entirety.

YAC clones are replicated in the yeast cells as authentic chromosomes and so they are present as only one copy per cell. This is an important difference with bacterial colony hybridization and makes colony filter treatment a critical step for successful sequence detection. After growing colonies overnight on the filters, the cell walls were digested and the spheroplasts were lysed in order to prepare yeast DNA for hybridization.

Yeast cell wall digestion is stimulated by reducing agents, such as 2-mercaptoethanol or DTT, that modify the wall structure and make it more sensitive to enzymatic action. Colony filters were placed on filter paper soaked in 0.8% DTT in SOE buffer (1 M sorbitol, 20 mM EDTA, 10 mM Tris-acetate pH 8.0) for 2-3 min. before transferring them to filter paper soaked in SOE containing 1% 2-mercaptoethanol and 1 mg/ml Zymolyase 10-T in individual 150×15 mm petri dishes. Petri dishes were parafilmed and stacked in a sealed plastic bag and incubated at 37° C. overnight.

After spheroplasting, lysis was carried out by placing the filters on whole sheets of Whatman 3MM paper soaked in the appropriate solution. The 3MM sheets were placed on Saran wrap and soaked immediately before use. The filters were treated as follows:

1. 10% SDS for 10 min.;
2. 0.5 M NaOH for 10 min (1.5 NaCl should be included for Hybond N+); Repeat;
3. Air dry for 5 min.;
4. 1 M Tris-HCl (pH 7.6), 1.5 M NaCl for at least 5 min;
5. 0.1 M Tris-HCl (pH 7.6), 0.15 M NaCl for at least 5 min. Cell debris on the filters was eliminated by gently wiping the filters with Kimwipes soaked in the same solution.
6. 2×SSPE for at least 5 min. This step precedes hybridization. Following lysis, the filters are air dried for 30 min. and baked for 2 hours at 80° C.

The left ends of the identified YAC clones were isolated by plasmid rescue according to Bell et al., 1994. Right ends were isolated by either vectorette PCR according to the methods of Matallana, et al., 1992, supra, or inverse PCR as described by Bell, et al., 1994, supra, the disclosures of which are hereby incorporated by reference in their entirety. The yUP library appeared to be missing clones corresponding to ATHCTR1; three clones hybridizing to this locus were found within the EG library (Grill and Somerville, *Mol. Gan. Genet.* 1991, 226, 484, incorporated herein by reference in its entirety.) The pEG23GSL left end plasmid rescue hybridizes to useful EcoR I and Xba I polymorphisms and hybridizes to the same lambda clone as ATHCTR1 (λctg24; Kieber et al., *Cell* 1993, 72, 427, incorporated herein by reference in its entirety). The left end rescue pyUP2GlllL hybridizes to EG23G5, linking the Ubq6121/g3715 and ATHCTR1 clones into a contiguous array. pyUP2G11L also contains a Bgl II polymorphism that is informative in the ein2-1 X DP28 cross. The three plants that are recombinant at ATHCTR1 are also recombinant at pyUP2GlllL; this indicates the position of ein2 is distal to this YAC end (FIG. 1).

Figure 2:
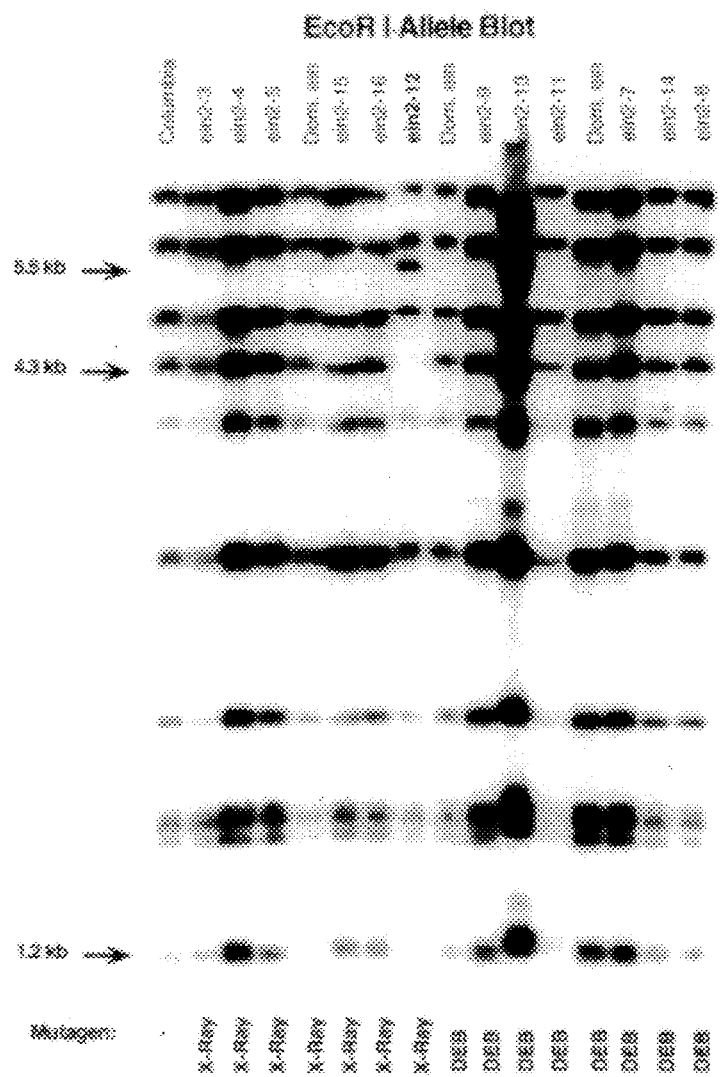
FIG. 2 is a genomic Southern blot. A polymorphism was detected in ein2-12 by hybridization with g3715. The g3715 cosmid was hybridized to a genomic Southern blot containing several alleles of ein2. In ein2-12 EcoR I digested genomic DNA, two bands were missing, 1.2 kb and 4.3 kb; and a new 5.5 kb fragment was detected. The DNA from the ein2 alleles was purified according to Chang et al. *Proc. Natl. Acad. Sci USA* 1988 85, 6857. 5 µg of EcoR I digested DNA was separated on a 0.8% agarose gel and blotted to hybond $N^+$ (Sambrook et al., *Molecular Cloning: A Laboratory Manual*, 2nd ed., 1989, Cold Spring Harbor Laboratory Press, Cold Spring Harbor, N.Y., Amersham, Arlington Heights, Ill.). All hybridizations were done using random hexamer labeled DNAs (Feinberg and Volgelstein, *Anal. Biochem* 1984 13Y, 266). Filters were prehybridized for at least 2 hours in 0.5 M sodium phosphate pH 7.2, 7% sodium dodecyl sulfate, and 1% BSA at 60° C. Hybridization of a minimum of 15 hours was in a solution of 0.5 M sodium phosphate pH 7.2, 7% sodium dodecyl sulfate, and 1% BSA at 60° C. Hybridization filters were washed and autoradiographed (Sambrook et al. 1989).

To facilitate the identification of the ein2 locus, 24 alleles were identified (Table 1; Guzman and Ecker, *Plant Cell* 1990, 2, 513, incorporated herein by reference in its entirety.) Many of these alleles were generated by X-ray or diepoxybutane mutagenesis; these mutagens are known to create polymorphisms that are detectable by hybridization to a genomic Southern blot (Clark, et al., *Genetics* 1986, 112, 755; Reardon et al., *Genetics* 1987, 115, 323, incorporated herein by reference in their entirety). EcoR I, Hind III, BamH I, Bgl II, and Sal I genomic Southern blots were made to find such a polymorphism in the mutant alleles of ein2. The following probes that mapped between Ubq6121 and yUP2GlllL were hybridized to the genomic allele blots: Ubq6121, EG19A10L, yUP2GllR, g3715, yUP19ElllL, EG23GSR, and yUP2GlllL. The cosmid clone g3715 hybridized to a restriction fragment length polymorphism in ein2-12 that corresponds to a lost EcoR I site (FIG. 2). Based on this missing EcoR I site, this region was examined further.

Figure 3:
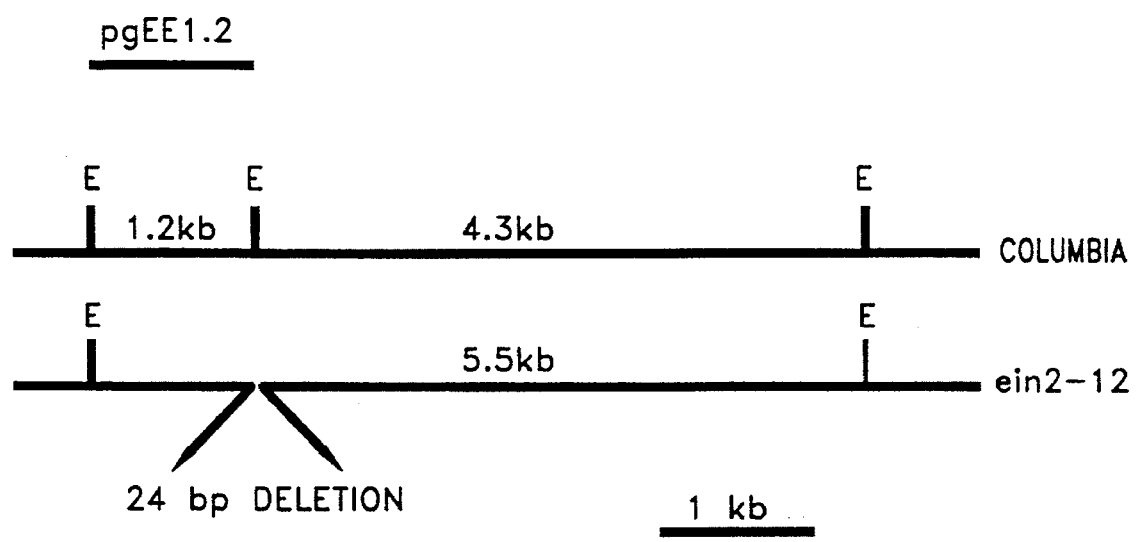
FIG. 3 is a diagram of the polymorphism in ein2-12 due to the loss of an EcoR I site. The pgEE1.2 subclone from g3715 is shown.
Figure 4:
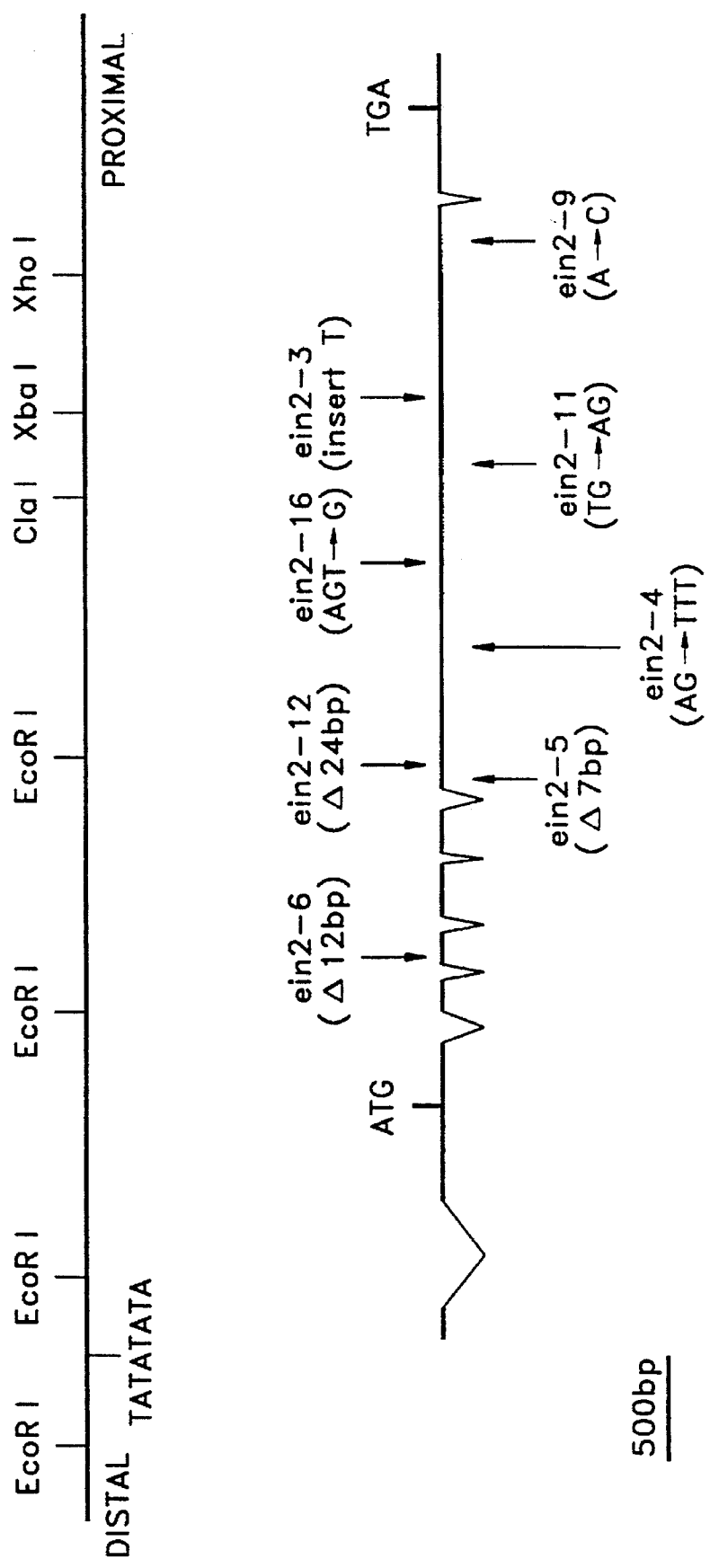
FIG. 4 is a description of the EIN2 locus, the cDNA (bottom) is shown relative to the genomic map (top). A putative TATA sequence is shown approximately 60 base pairs 5' to the start of the cDNA. The position of the translation start and stop sites are also shown.

The 1.2 kb EcoR I fragment that corresponds to one of the missing bands in ein2-12 was subcloned from g3715 into pKS (Stratagene, LaJolla, Calif.) this clone is named pgEE1.2 (FIG. 3). The pgEE1.2 insert was used to isolate 22 cDNA clones made from ethylene treated three-day old etiolated *Arabidopsis thaliana* seedlings (Kieber, et al. 1993, supra.) pgEE1.2 was also used to identify a single genomic lambda clone, λgE2, from a λDASH II library made from adult Columbia plants. The λgE2 clone spanned the 5' end of the locus and terminated within the 3' end of the cDNA. Initially the pcE2.5 clone was sequenced but since this clone was not full length, the 5' ends of pcE2.17, pcE2.20, and pcE2.22 (Kiebez, et al. 1993) were sequenced to determine the structure of the full length frame and ending within 60 bp from a putative "TATA" box (FIG. 4). Using 5 µg of poly(A+) RNA from 3-day old dark-grown, ethylene-treated Arabidopsis seedlings (hypocotyls and cotyledons) as template and oligo(dT) as primer, first-strand cDNA synthesis was catalyzed by Moloney murine leukemia virus reverse transcriptase (Pharmacia) for construction of the Arabidopsis cDNA expression library. Second-strand cDNA was made as described by Gubler and Hoffman, *Gene* 1983, 25, 263, which is hereby incorporated by reference in its entirety, except that *E. coli* DNA ligase was omitted. After the second-strand reaction, the ends of the cDNA were made blunt with Klenow fragment, and EcoR I-Not I adaptors (Pharmacia) were ligated to each end. The cDNA was purified from unligated adaptors by spun-column chromatography using Sephacryl S-300 and size fractionated on a 1% low melting point minigel. Size-selected cDNAs (0.5–1, 1–2, 2–3, and 3–6 kb) were removed from the gel using agarose (New England BioLabs), phenol-chloroform extracted, and precipitated using 0.3M NaOAc (pH 7)-ethanol. A portion of each cDNA size fraction (0.1 µg) was coprecipitated with 1 µg of λZAPII EcoRI-digested, dephosphorylated arms and then ligated overnight in a volume of 4 µl. Each ligation mix was packaged in vitro using Gigapack II Gold packaging extract (Stratagene). The structure of this locus was determined by Southern hybridization and restriction mapping of the λgE2 and g3715.

The sequence of the EIN2 genomic DNA was determined from PCR products and the λgE2 genomic lambda clone. Primers were selected from the sequence of the pcE2.5, pcE2.17, and genomic subclones of λgE2. The primers were then commercially synthesized (Research Genetics, Huntsville, Ala.).

TABLE 3

PRIMERS FOR THE EIN2 LOCUS

| SEQUENCE ID NO. | Primer Name | Sequence | position |
|---|---|---|---|
| 21 | PE2.7A | GGATCCTCTAGTCAAATTACCGC | |
| 22 | PE2.7B | AGATCTGGTATATTCCGTCTGCAC | |
| 23 | PE2.5' | CCGGATTCGGTTTGTAGC | PCR/ 3' end |
| 24 | PE1 | GACGTGCATGTTCTTGGG | |
| 25 | PE2 | GAAAGCCACATCACCTGC | |
| 26 | PE3 | GGGGTGGAGTTATCCAC | |
| 27 | PE4 | GACACCGGGAAGTATCG | |
| 28 | PE5 | CTGCTTTCATAGAAGAGGC | PCR/ middle |
| 29 | PE6 | GTCAGAACAAACCTGCTCC | PCR/ 5' end |
| 30 | PE7 | CACCCAGGTCTTGGTGG | |
| 31 | PE8 | GGCCGCCATGGATGCG | |
| 32 | PE9 | TCTCAATCAAGAGGAGGC | |
| 33 | PE10A | CTTGAAGGATCCGAGTGG | |
| 34 | PE11 | CAGGTTGGCGAGTTCCTCG | |
| 35 | PE12 | CTTGCTGTTATTCTCCATGC | |
| 36 | PE13 | CCCTGGACCAGCTCCTGG | |
| 37 | PE14 | TGGCGCAAGCATCGTCCC | PCR/ middle |
| 38 | PE15 | AAATGTTCAGGAATCTCTCG | |
| 39 | PE16 | CTGGCTGGCAGCCACGCC | PCR/ 3' end |
| 40 | PE17 | GCGTTCTCAAAGCTGCGG | |
| 41 | PE18 | ACTGATGGGTCTTCTGGG | |
| 42 | PE19 | GGATCAGGATGGACCCGG | |
| 43 | PE20 | TGGTTGCTGAAGCCAGGG | |
| 44 | PE21 | TCCATTCATAGAGAGTGGG | |
| 45 | PE22 | ATGCCCAAGAACATGCACG | |
| 46 | PE23 | CAACTGATCCTTTACCCTGC | |
| 47 | PE24 | GTTGTTAGGTCAACTTGCG | PCR/ 5' end |
| 48 | PE25 | CTCTGTTAGGGCTTCCTCC | |
| 49 | PE26A | GAATCAGATTTCGCGAGG | |
| 50 | PE27 | GTCCAAATGGAGGAAGCC | |
| 51 | PE28 | CCACGACTGTACAATTGACCTTG | engineered MunI site |
| 52 | PE29 | CATGATCGCAAGTTGACC | |
| 53 | PE30 | AGAAAACTCTTATCAAGCTACG | |
| 54 | PE31 | AAGCTTATGGGTGCTCGTGC | |
| 55 | PE32 | GGAAAGAGAGAAAGACTCAG | |
| 56 | PE33 | GCCACCAAGTCATACCCG | |

Primer sequences are set forth 5' to 3'.

Figure 5A:
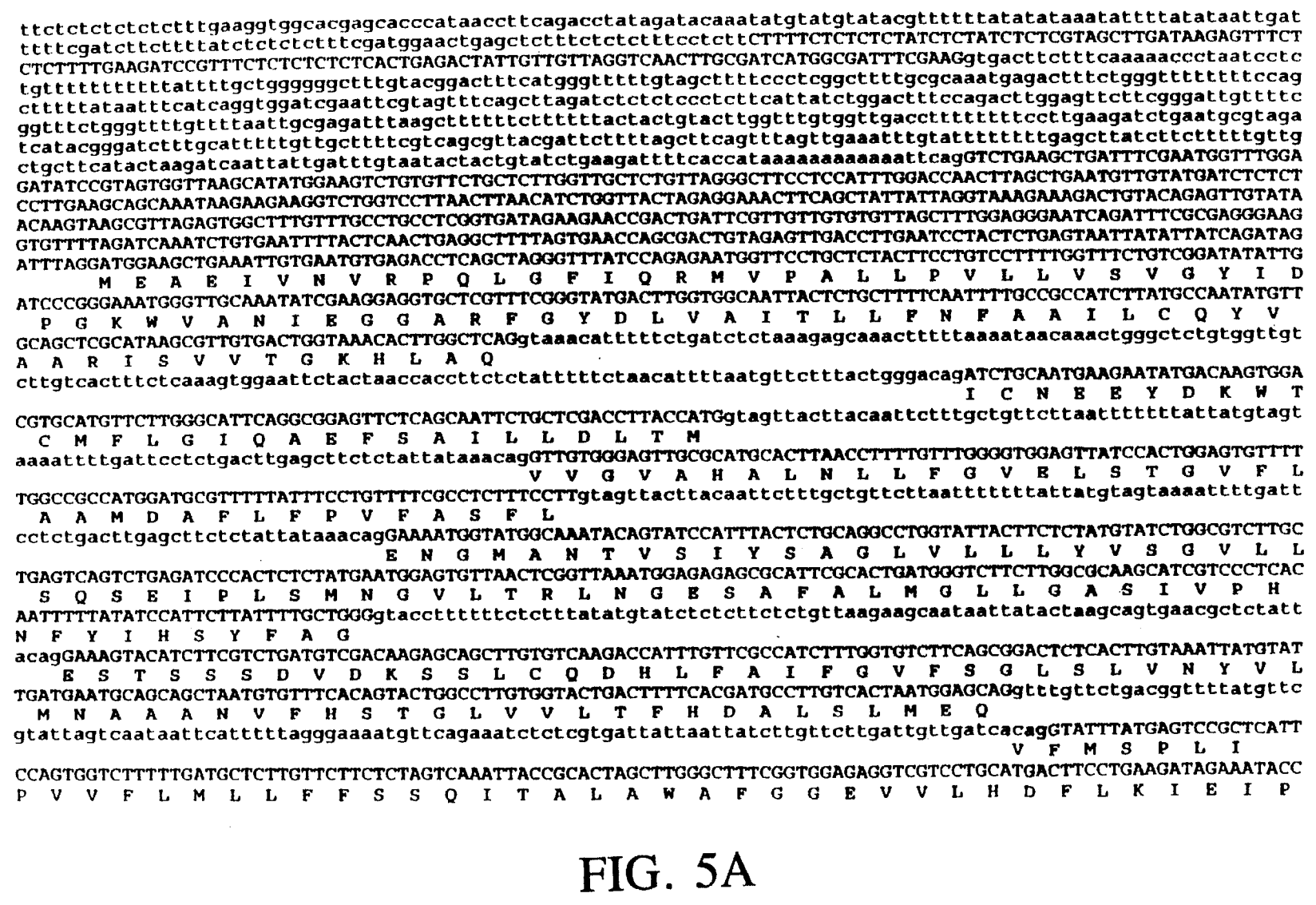
Figure 5B:
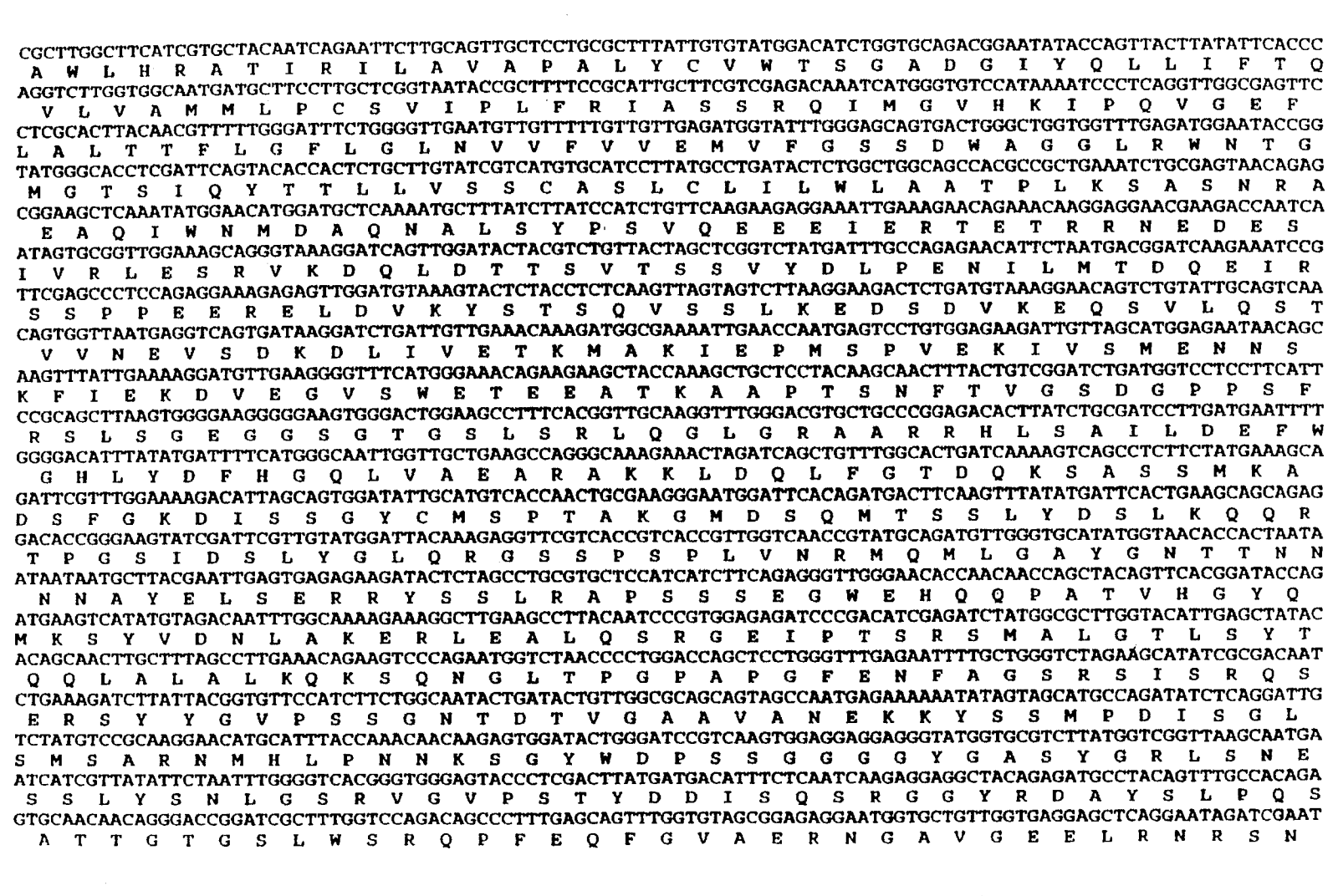

Four overlapping regions of the ein2 locus between 1.2 and 3.2 kb in length were rapidly amplified by polymerase chain reactions (Idaho Tecknologies, Idaho falls, Idaho). Conditions for the PCR reactions are as follows: 92° C., 2 seconds; 56° C., 2 seconds; 72° C., 1 minute; 50 cycles. Between 200 and 500 ng of these PCR products were directly sequenced on the ABI373A automated sequencer using Taq Dye-Terminator chemistry (Applied Biosystems Division, PEC). The genomic sequence of the wild type Columbia EIN2 locus is shown in FIGS. 5A–C. Eight mutant alleles of ein2 were also sequenced and the corresponding mutations identified (Table 4). The presence of these mutations in the mutant alleles of ein2 confirms the identity of this gene as EIN2.

TABLE 4

INDENTIFIED MUTATIONS OF EIN-2

| ALLELE | MUTAGEN | MUTATION | POSITION* | RESULT |
|---|---|---|---|---|
| ein2-3 | X-ray | Insert T | +3642 | Frameshift |
| ein2-4 | X-ray | AG to TT | +2103 | Frameshift |
| ein2-5 | X-ray | ΔCATGACT | +1570 | Frameshift |
| ein2-6 | Agro-bacterium | ΔGAGTTGCGC ATG (SEQ ID NO: 17) | +965 | ΔGVAH (115) (SEQ ID NO: 18) |
| ein2-9 | DEB | A to C | +4048 | H to P |
| ein2-11 | DEB | TG to AT | +3492 | Ochre |
| ein2-12 | X-ray | ΔTGCTACAAT CAGAATTCTT GCAGT (SEQ ID NO: 19) | +1611 | ΔAATIRILAV (SEQ ID NO: 20) |
| ein2-16 | X-ray | AGT to G | +2851 | Frameshift |

*Position relative to the start of pcE2.17; see FIGS. 5A–C, nucleic acid; position 1 corresponds to the beginning of the cDNA.

EXAMPLE 3

CLONING AND SEQUENCING OF EIN3

In order to clone the EIN3 gene a collection of 5000 T-DNA insertion lines (Feldmann and Marks, *Mol. Gen. Genet.* 1987, 208, 1–9, incorporated herein by reference in its entirety) was screened for ethylene-insensitive mutants. A mutant with a phenotype similar to that of ein3-1 (an EMS generated allele) was identified and genetic complementation tests revealed that ehn3-1 and the T-DNA insertion mutant (designated ein3-2) were allelic. Complete cosegregation of the mutant phenotype and the dominant kanamycin resistance marker on the T-DNA indicated that the T-DNA insertion was located within, or at least very close, to the EIN3 gene. Genomic DNA flanking the T-DNA insert was cloned using the left border rescue technique. Genomic Southern blots of wild-type and ein3-2 DNA hybridized with the rescued fragment indicated that the cloned segment of Arabidopsis DNA corresponded to sequences disrupted by the T-DNA insert and did not result from cloning an unlinked fragment of genomic DNA. In all restriction digests the mobility of the hybridizing fragments is shifted in the insertion mutant relative to wild-type.

cDNA and genomic libraries constructed from wild-type DNA were screened with the rescued DNA fragment. The cDNAs obtained indicated the the EIN3 gene encodes a 628 amino acid open reading frame. Structural features of the predicted poly peptide include: 1) a region rich in acidic amino acids at the amino terminus, 2) several basic domains in the central portion of the protein, and 3) several polyasparagine repeats near the carboxy terminus. Although database searches revealed no overall similarities to any characterized proteins, the three structural motifs described are found in transcriptional regulatory proteins. Stretches of acidic amino acids function in transcriptional activation presumably through binding to other proteins. Basic domains serve as nuclear localization signals and can bind DNA. Poly asparagine repeats are present in the SWI1 protein of yeast. This protein has been termed a transcriptional accessory protein because it is required for transcriptional activation of target genes but does not bind directly to DNA. It has been suggested that the poly asparagine repeats are involved in protein-protein interactions.

Sequencing genomic clones indicated that the EIN3 gene has a very simple structure. There are no introns within its open reading frame. Howewer there is a single intron located in the 5' transcribed region. In addition to sequencing the wild-type EIN3 gene, genes from three independently isolated ein3 mutants were sequenced. In each case an alteration was identified confirming the identification of the bona fide EIN3 gene. In the ein3-1 allele, a point mutation introduces a premature in frame stop codon. The ein3-2 allele contains a T-DNA insertion which interupts the coding region. A point mutation in the ein3-3 allele substitutes an acidic amino acid for a basic amino acid within one of the basic regions described above.

The expression pattern of the EIN3 gene in seedlings was examined by placing the GUS reporter gene under control of the EIN3 promoter. The construct employed was a translational fusion including 5' non-transcribed sequences, the 5' intron and 93 amino acids of the EIN3 coding region cloned upstream of the GUS gene in the pBI101 vector (Jefferson et al., *EMBO J*, 1987, 6, 3901–3907, incorporated herein by reference in its entirety) and named pHSEIN3GUS. Arabidopsis root explants were transformed and transgenic plants regenerated (Velvekins et al., PNAS 1988, 85, 5536–5540, incorporated herein by reference in its entirety). The GUS activity patterns observed suggest that the EIN3 promoter is most active in expanding or elongating cells. In three day old etiolated seedlings GUS activity staining is located predominantly in the apical hook and root tips. In younger seedlings in which the hypocotyl is not fully extended staining is also prevalent throughout this tissue. In 14 day old light grown seedlings abundant GUS activity is observed in the roots, upper portions of the hypocotyl, cotyledons and leaves. The EIN3 promoter is not induced by ethylene as the levels of GUS activity in air and ethylene treated seedlings appear equivalent. This observation is supported by the fact that steady state levels of the endogenous EIN3 transcript are similar in ethylene and air treated seedlings and adult plants as determined by Northern analysis.

Figure 18:
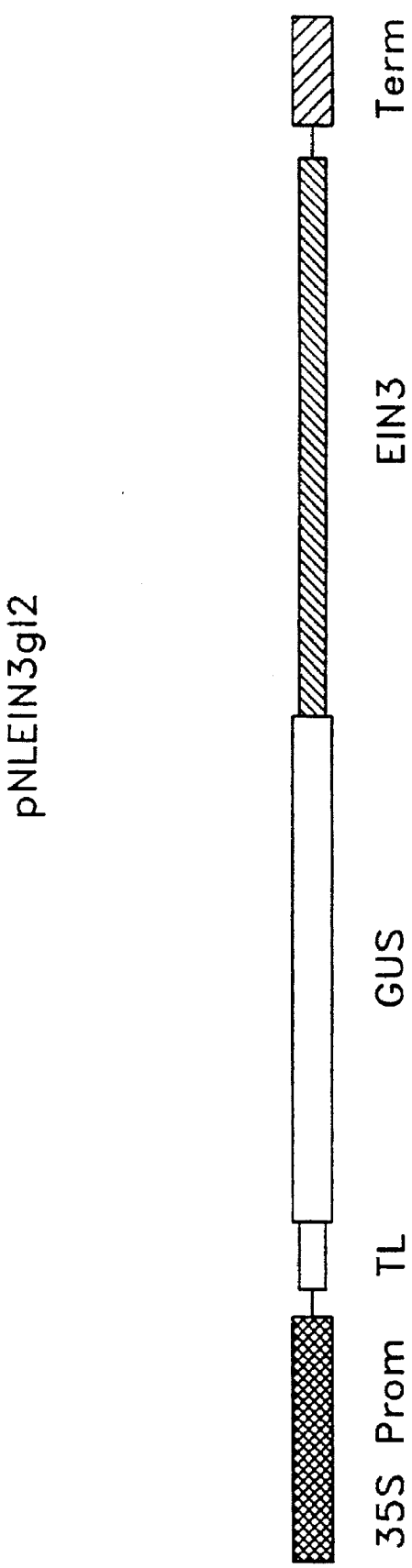
FIG. 18 is a representation of pNLEIN3Bgl2 indicating the relationship between the promoter, GUS, and EIN3 sequences.

The EIN3 coding region was cloned downstream of the bacterial reporter gene B glucuronidase (GUS) in the plasmid pRTL2-GUS according to the methods of Restrepo et al., *Plant Cell* 1990, 2, 987–998, incorporated herein by reference in its entirety, to create pNLEIN3Bg12 (see FIG. 18). The plasmid was transformed into Arabidopsis protoplasts and transiently expressed according to the methods of Abel and Theologis, *Plant J.* 1994, 5, 421–427, incorporated herein by reference in its entirety. All detectable GUS activity was targeted to the nuclei of the protoplasts indicating that the EIN3 protein functions in the nucleus. These results suggest that the EIN3 protein may function as a transcription factor which regulates ethylene-regulated gene expression.

The EIN3 gene is a member of a small gene family. Low stringency hybridization of genomic Southern blots indicates that there are at least two members in addition to EIN3. Three EIN3 homologue, designated as EIL1, EIL2, and EIL3, have been cloned and sequenced. The EIL and EIN3 predicted polypeptides structurally similar in that the amino termini of both proteins are rich in acidic amino acids and their central regions contain several basic domains. Their carboxyl termini are not as well conserved as EIL1 contains a polyglutamine repeat instead of poly asparagine repeats.

The EIL2 and EIL3 polypeptides do not contain polyglutamine repeats or poly asparagine repeats. It is interesting to note that the amino acid substitution in the ein3-3 allele occurs in one of the regions rich in basic amino acids that is completely conserved between the EIN3 and EIL polypeptides. Currently, it is not known whether the EIL gene product functions in the ethylene signal transduction pathway of Arabidopsis. However at this time, the EIL1 and EIL2 cDNAs do not map to the same location as any of the characterized ethylene response mutations. The location of the EIL3 cDNA has not yet been mapped. The EIL1 polypeptide is the most similar to EIN3.

The ein3 mutant alleles were sequenced on an Applied Biosystems 373A DNA Sequencing System (Foster City, Calif.) using Taq dideoxy terminator chemistry (Applied Biosystems). The PCR primers are set forth in Table 5.

TABLE 5

PRIMERS FOR EIN3 PCR

| SEQUENCE ID NO. | PRIMER NAME | SEQUENCE | POSITION in genomic |
|---|---|---|---|
| 57 | PR24 | CCTTCTATATTTGGTTCC | 680–698 |
| 58 | PR15 | CCATTCTCCGGAATAATCC | 1306–1324 |
| 59 | PR5 | CACGGAGCAGGATAAGGGTA | 1148–1166 |
| 60 | PR19 | CGGATTGGATTGTGTGTGC | 3312–3331 |

The primer sequences are set forth 5' to 3'.

Primer pairs PR24 - PR15 and PR5 - PR19 were used to amplify genomic DNA from the ein3 mutants. PCR amplification was performed with a Biosycler Oven (New Haven, Conn.). Conditions for amplification were as follows: 92° C. for 1 min; 55° C. for 1 min.; 72° C. for 3 min. The mutations discovered are listed in Table 6.

TABLE 6

IDENTIFIED MUTATIONS OF EIN3

| Allele | Mutagen | Sequence change | Consequences of sequence change |
|---|---|---|---|
| ein3-1 | EMS | G to A, position 1598 | amino acid 215, W to umber |
| ein3-2 | T-DNA | position 2001 | T-DNA insertion |
| ein3-3 | DEB | G to T, position 1688 | amino acid 245, K to N |

The EIL genes were obtained by screening an Arabidopsis seedling cDNA library (Kieber et al., *Cell*, 1993, 72, 427–441, at low stringency in the following manner. The cDNA library was hybridized with the radiolabeled EIN3 cDNA insert at 42° C. for 48 hours in a hybridization solution consisting of 30% formamide, 5× Denhardt's solution, 0.5% SDS, 5× SSPE, 0.1 mg/ml sheared salmon sperm DNA, according to the methods of Feinberg and Vogelstein, *Anal. Biochem.* 1984, 177, 266–267, incorporated herein by reference in its entirety. The filters were washed at 42° C. with 30% formamide, 0.5% SDS, 5× SSPE; followed by 2× SSPE.

EXAMPLE 4

HOOKLESS MUTATION OF THE APICAL HOOK

The "triple response" in *Arabidopsis thaliana* occurs in response to the plant hormone ethylene and is characterized by three distinct changes in the morphology of etiolated seedlings. These include, exaggeration of the apical hook, radial swelling of the hypocotyl, and inhibition of root and hypocotyl elongation. Observation of the apical hook was recorded by Charles Darwin as early as 1896.

The hook causes the apical portion of the seedling to become nearly parallel with the basal portion. Production of the bend in the hypocotyl requires either a larger number of cells, or increased elongation of cells on the adaxial side (outside) of the hook. A study of the characteristics of hook formation in bean seedlings demonstrated that the curvature is produced by differential growth rates on each half of the hypocotyl resulting in longer cells on the convex side of the hook, see Rubenstein, 1972 *Plant Physiology* 49:640–643.

Previous studies suggest that hormones may be involved in hook formation. The hormones involved are believed to be auxin and ethylene. Auxin is known to be a controlling factor in cell elongation in the hypocotyl, see Klee and Estelle, 1991 *Annual Review of Plant Physiology* 42:529–551, incorporated herein by reference in its entirety, and ethylene has been shown to exaggerate the bending of the hook in wild type etiolated seedlings (Guzman and Ecker, supra). One hypothesis to explain hook formation is that auxin promotes elongation of cells on the outside of the apical hook allowing differential growth rates and bending. Work performed by McClure and Guifoyle (1989) demonstrated that the initial uniform expression of small auxin up-RNA (SAUR) mRNA on both sides of the hypocotyl was altered when the tissue was transferred from an erect to horizontal position. An increase in SAUR mRNA accumulation was observed on the "outside" region and a concurrent rapid decrease in SAUR mRNA occurred on the "inside" region of an upward bending hypocotyl. Ethylene has been shown to alter transport of auxin in hypocotyl tissue (Mattoo and Suttle, supra), suggesting a possible role for ethylene in exaggeration of the hook. To exaggerate the hook, ethylene might affect auxin localization causing even more bending on the outside of the hook.

The triple response of Arabidopsis has been used to isolate mutants affected in the ethylene response. The hookless 1 (hls1) mutant exhibits a tissue specific defect in the triple response. Null mutants (hls1-1) completely lack the apical hook in the presence and absence of ethylene while weak alleles of hls1 (hls1-2) show some bending in the hook in the presence of ethylene. The complementation cross between hls1-1 end hls1-2 gave rise to F1 progeny which resembled hls1-2. In addition to hls1-1 and hls1-2, six EMS alleles, three FEB alleles, one X-ray allele, and two non-tagged T-DNA alleles have been isolated in accordance with the methods set forth in Guzman et al. *The Plant Cell* 1990 2:513–523, hereby incorporated by reference in its entirety (Table 7). Seven of these are strong alleles which are completely hookless in the presence of ethylene. Five of these ere weak alleles showing a partial bend in the presence of ethylene. The hls1 phenotype is epistatic in the hook with other ethylene mutants.

TABLE 7

IDENTIFIED PHENOTYPIC AND PROTEIN MUTATIONS OF HLS1

| ALLELE | MUTAGEN | HOOK ANGLE | CHANGE |
|---|---|---|---|
| hls1-1 | EMS | 2.2 ± 0.9 | aa345 E to K |
| hls1-2 | T-DNA | 26.2 ± 3.2 | T-DNA insertion |
| hls1-3 | X-RAY | 8.1 ± 1.8 | 4.8kb |

TABLE 7-continued

IDENTIFIED PHENOTYPIC AND PROTEIN MUTATIONS OF HLS1

| ALLELE | MUTAGEN | HOOK ANGLE | CHANGE |
|---|---|---|---|
| hls1-4 | DEB | ND (strong) | deletion of promoter aa345 E to K |
| hls1-5 | DEB | 1.3 ± 0.5 | splice donor site mutated |
| hls1-6 | EMS | 2.1 ± 1.0 | aa326 K to W |
| hls1-7 | DEB | 3.0 ± 1.3 | splice donor site mutated |
| hls1-8 | EMS | 2.1 ± 1.2 | aa180 R to stop |
| hls1-9 | EMS | 6.3 ± 1.5 | aa11 R to stop |
| hls1-10 | EMS | 23.2 ± 3.0 | aa1 M to I |
| hls1-11 | T-DNA | 3.0 ± 1.2 | ND |
| hls1-12 | EMS | ND (weak) | NC |
| hls1-13 | EMS | ND (weak) | NC |
| hls1-14 | T-DNA | ND (strong) | ND |

ND = not determined;
NC = no change in coding region or introns

Gene Structure and Analysis

The HLS1 gene was cloned by left border rescue of a T-DNA inserted in the promoter of h3sl-2. The rescued fragment was used to isolate a 12 kb genomic clone which was then used to isolate three cDNA clones. The T-DNA was found to have inserted 710 bp upstream from the 5' end of a 1.7 kb cDNA clone. Deletions of the 1.7 kb cDNA clone were generated in both directions using Exonuclease III. These clones were sequenced using Sequenase 2.0. Deletions of the genomic clone were also generated using Exonuclease III. These clones were also sequenced. The sequence of the genomic clone covered the entire 1.7 kb cDNA as well as 1712 bp upstream of the start of the cDNA and 313 bp at the 3' end of the cDNA. This gene has two introns of 342 bp and 81 bp in size. The cDNA encoded a 403 amino acid protein of about 43 kDa.

Sequence Analysis of the Alleles

The hls1 gene from ten of the fourteen alleles was sequenced. The transcribed region as well as both introns were sequenced. The hls1 gene from each allele was isolated by PCR amplification. The sequences of the primers is set forth in Table 8.

TABLE 8

PRIMERS FOR HLS1 PCR

| SEQUENCE ID NO. | PRIMER NAME | SEQUENCE | POSITION in genomic |
|---|---|---|---|
| 61 | II.1 | cgccactgcatgtaagaac | 1303–1321 |
| 62 | II.2 | tccacacgcttaatacggc | 3229–3211 |
| 63 | II.6 | ggtacggagaagaaggag | 2546–1563 |
| 64 | III.1 | cgcgggatattgattcggt | 3071–3090 |
| 65 | III.2 | gtgttgaacacgcccacaa | ND |
| 66 | III.3 | acgacaccacaaccacct | 3479–3462 |
| 67 | III.5 | gacaagaagacacaaacc | 3880–3863 |
| 68 | pr1 | gaatcggaggagaaggtc | 3386–3403 |

Primer sequences are set forth 5' to 3'.

PCR was performed on a Biosycler (New Haven, Conn.). Conditions were 92° C., 1 min.; 55° C., 1 min.; 72° C., 3 min. for 35 cycles. Some of the PCR products were subcloned and sequenced using Sequenase. Additional PCR products were sequenced directly using sequence specific primers and Taq sequencing on an ABI automated sequencer (Foster City, Calif.). Alleles found to contain a sequence change from wild type were confirmed by direct sequencing of the PCR product along with a wild type control. The changes found in these alleles are listed below in Table 9.

TABLE 9

IDENTIFIED GENOTYPIC AND PROTEIN MUTATIONS OF HLS1

| ALLELE | MUTAGEN | SEQUENCE CHANGE | CONSEQUENCES OF SEQUENCE CHANGE |
|---|---|---|---|
| hls1-1 | EMS | G to A position 3487 | aa345 E to K |
| hls1-5 | DEB | T to A position 2194 | splice donor site mutated |
| hls1-7 | DEB | T to A position 2194 | splice donor site mutated |
| hls1-6 | EMS | T to G position 3431 | aa326 K to W |
| hls1-4 | DEB | G to A position 3487 | aa345 E to K |
| hls1-9 | EMS | C to T position 2060 | aa11 R to stop (CGA—TGA) |
| hls1-8 | EMS | C to T position 2992 | aa180 R to stop (CGA—TGA) |
| hls1-10 | EMS | G to A position 2033 | aa1 M (start) to I |

Two alleles which showed no changes in the transcribed region or in the introns, hls1-12 and hls1-13, were both weak alleles. hls1-12 was found to have reduced levels of transcript compared with wild type. It is possible that there are sequence changes in the promoter region of hls1-12 and hls1-13.

Spatial and Temporal Detection and Expression

Northern analysis of the alleles revealed weak alleles hls1-2, hls1-3, hls1-12 all show a reduction in the amount of transcript. The HLS1 transcript was found to be up regulated by ethylene.

HLS1 Homology

Sequence comparison was done at the DNA as well as the amino acid level using Blast and TFASTA (GCG). Some homology to one class of acetyl transferases was found. There are several classes of acetyl transferases with little homology between classes. The homology in one class of acetyl transferases is comprised of only a loose consensus. HLS1 is similar to a class of acetyl transferases found in bacteria and yeast and not similar to the class found in mammalian systems. Tercero, J. C., JBC 1992, 267, 20270, published a minimum consensus for one class of acetyl transferases. Other members of this class include yeast MAK3 gene, which acetylases a viral coat protein and perhaps some mitochondrial proteins. The rimL and rimJ proteins are also in this class of acetyl transferases. These are E. coli proteins which acetylate ribosomal proteins L12 and L5. Also included in this class is the ARD1 protein of yeast. Mutants in this gene show a specific mating defect, an inability to sporulate, and loss of viability in stationary phase. There are several other bacterial members of this class. The other 150 amino acids of the HLS1 gene show no significant homology to any proteins in the database.

Various modifications of the invention in addition to those shown and described herein will be apparent to those skilled in the art from the foregoing description. Such modifications are also intended to fall within the scope of the appended claims.

What is claimed is:

1. An isolated nucleic acid sequence comprising a sequence selected from the group consisting of SEQUENCE ID NOS: 1 and 2.

2. An isolated protein sequence comprising the amino acid sequence set forth in SEQUENCE ID NO: 3.

3. An isolated nucleic acid sequence comprising the sequence set forth in SEQUENCE ID NO: 4.

4. An isolated nucleic acid sequence comprising the sequence set forth in SEQUENCE ID NO: 5.

5. An isolated protein sequence comprising the amino acid sequence set forth in SEQUENCE ID NO: 6.

6. An isolated nucleic acid sequence comprising the sequence set forth in SEQUENCE ID NO: 7.

7. An isolated protein sequence comprising the amino acid sequence set forth in SEQUENCE ID NO: 8.

8. An isolated nucleic acid sequence comprising the sequence set forth in SEQUENCE ID NO: 9.

9. An isolated protein sequence comprising the amino acid sequence set forth in SEQUENCE ID NO: 10.

10. An isolated nucleic acid sequence comprising the sequence set forth in SEQUENCE ID NO: 11.

11. An isolated protein sequence comprising the amino acid sequence set forth in SEQUENCE ID NO: 12.

12. An isolated nucleic acid sequence comprising a sequence selected from the group consisting of SEQUENCE ID NO: 14 and 15.

13. An isolated protein sequence comprising the amino acid sequence set forth in SEQUENCE ID NO: 16.

14. A DNA sequence comprising a sequence complementary to an isolated nucleic acid sequence of claim 1.

15. A plant cell transformed to comprise a nucleic acid sequence selected from the group consisting of SEQUENCE ID NOS: 1, 2, 4, 5, 7, 9, 11, 14, and 15.

16. A plant transformed to comprise a heterologous nucleic acid sequence selected from the group consisting of SEQ ID NOS: 1, 2, 4, 5, 7, 9, 11, 14, and 15.

17. A DNA sequence comprising a sequence complementary to an isolated nucleic acid sequence selected from the group consisting of SEQ ID NOS: 1, 2, 4, 5, 7, 9, 11, 14, and 15.

* * * * *